(12) United States Patent
Zhang et al.

(10) Patent No.: US 12,365,740 B2
(45) Date of Patent: Jul. 22, 2025

(54) ANTI-CD40 ANTIBODIES AND USES THEREOF

(71) Applicant: NANKAI UNIVERSITY, Tianjin (CN)

(72) Inventors: Hongkai Zhang, Tianjin (CN); Yuan Wang, Tianjin (CN)

(73) Assignee: Nankai University, Tianjin (CN)

( * ) Notice: Subject to any disclaimer, the term of this patent is extended or adjusted under 35 U.S.C. 154(b) by 954 days.

(21) Appl. No.: 17/594,255

(22) PCT Filed: Apr. 10, 2020

(86) PCT No.: PCT/CN2020/084186
§ 371 (c)(1),
(2) Date: Oct. 8, 2021

(87) PCT Pub. No.: WO2020/207470
PCT Pub. Date: Oct. 15, 2020

(65) Prior Publication Data
US 2022/0324988 A1    Oct. 13, 2022

(30) Foreign Application Priority Data

Apr. 10, 2019  (CN) .......................... 201910284441.1
Apr. 3, 2020   (CN) .......................... 202010262466.4

(51) Int. Cl.
| | | |
|---|---|---|
| C07K 16/28 | (2006.01) | |
| A61K 39/395 | (2006.01) | |
| A61K 45/06 | (2006.01) | |
| A61P 35/00 | (2006.01) | |
| A61K 39/00 | (2006.01) | |

(52) U.S. Cl.
CPC ...... *C07K 16/2878* (2013.01); *A61K 39/3955* (2013.01); *A61K 45/06* (2013.01); *A61P 35/00* (2018.01); *A61K 2039/505* (2013.01); *C07K 2317/21* (2013.01); *C07K 2317/24* (2013.01); *C07K 2317/33* (2013.01); *C07K 2317/565* (2013.01); *C07K 2317/732* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen ..................... | A61P 19/02 435/69.6 |
| 8,591,900 B2 * | 11/2013 | Barrett .................... | A61P 43/00 424/152.1 |
| 2012/0301488 A1 | 11/2012 | Zhang et al. | |
| 2014/0120103 A1 | 5/2014 | Zhang et al. | |
| 2018/0078640 A1 | 3/2018 | Yu et al. | |

FOREIGN PATENT DOCUMENTS

| | | |
|---|---|---|
| CN | 103635488 A | 3/2014 |
| CN | 109069621 A | 12/2018 |
| CN | 109265552 A | 1/2019 |
| WO | 2017059196 A2 | 4/2017 |
| WO | 2017205742 A1 | 11/2017 |

OTHER PUBLICATIONS

Slastnikova, Tatiana A., et al. "Targeted intracellular delivery of antibodies: the state of the art." Frontiers in pharmacology 9 (2018): 1208 (Year: 2018).*
Kim, Jisun, et al. "Computational and artificial intelligence-based methods for antibody development." Trends in pharmacological sciences 44.3 (2023): 175-189 (Year: 2023).*
Bates, Adam, and Christine A. Power. "David vs. Goliath: the structure, function, and clinical prospects of antibody fragments." Antibodies 8.2 (2019): 28 (Year: 2019).*
Stryer, Biochemistry 4th, WH Freeman, New York. 1995 (Year: 1995).*
Colman, Research in Immunology 145.1 (1994): 33-36) (Year: 1994).*
Peters, Anna L et al. "CD40 and autoimmunity: the dark side of a great activator." Seminars in immunology vol. 21,5 (2009): 293-300. doi:10.1016/j.smim.2009.05.012 (Year: 2009).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Liu, Yaohui, et al., "High-throughput reformatting of phage-displayed antibody fragments to IgGs by one-step emulsion PCR," Protein Engineering, Design & Selection, vol. 31, issue No. 11 (Apr. 9, 2019), pp. 427-436.
International Search Report (Form PCT/ISA/210) for International Patent Application No. PCT/CN2020/084186, issued from the International Searching Authority, date of mailing Jul. 9, 2020, with English-language translation, 14 pages.
Written Opinion of the International Searching Authority (Form PCT/ISA/237) for International Patent Application No. PCT/CN2020/084186, issued from the International Searching Authority, dated Jul. 9, 2020, with English-language translation, 9 pages.

* cited by examiner

*Primary Examiner* — Zachariah Lucas
*Assistant Examiner* — Lia E Taylor
(74) *Attorney, Agent, or Firm* — Ice Miller LLP

(57) ABSTRACT

The present invention relates to novel antibodies and antibody fragments that specifically bind to CD40, and compositions, medicaments, combination products and kits comprising the antibodies or antibody fragments. Furthermore, the invention relates to nucleic acids encoding said antibodies or antibody fragments thereof and host cells comprising the same, as well as related uses. Furthermore, the invention relates to therapeutic and diagnostic uses of these antibodies and antibody fragments.

17 Claims, 20 Drawing Sheets

Specification includes a Sequence Listing.

ANTI-CD40 ANTIBODIES AND USES THEREOF

CROSS-REFERENCE TO RELATED APPLICATIONS

This application is a Section 371 of International Application No. PCT/CN2020/084186, filed on Apr. 10, 2020, which published in the Chinese language on Oct. 15, 2020 under International Publication No. WO 2020/207470 A1, which claims priority to Chinese Application No. 201910284441.1, filed on Apr. 10, 2019, and Chinese Application No. 202010262466.4, filed on Apr. 3, 2020. Each disclosure is incorporated herein by reference in its entirety.

REFERENCE TO SEQUENCE LISTING SUBMITTED ELECTRONICALLY

This application contains a sequence listing, which is submitted electronically via EFS-Web as an ASCII formatted sequence listing with a file name "PF200148PCT_Sequencelisting-EN" and a creation date of Oct. 6, 2021 and having a size of 75.9 kb. The sequence listing submitted via EFS-Web is part of the specification and is herein incorporated by reference in its entirety.

The present invention relates to novel antibodies and antibody fragments that specifically bind to CD40 and compositions, and medicaments, combination products or kits comprising the same. Furthermore, the invention relates to nucleic acids encoding said antibodies or antibody fragments thereof and host cells comprising the same, as well as related uses. Furthermore, the invention relates to therapeutic and diagnostic uses of these antibodies and antibody fragments.

BACKGROUND

Full activation of T cells requires two signals: the tumor antigen is taken up and processed by Antigen Presenting Cells (APC) to form MHC-antigen complexes, which are presented to T cells and bound to TCR on the surface of the T cells. This is the first signal for T cell activation; the second or co-stimulatory signal is transmitted by the interaction of CD28 with B7-1(CD 80)/B7-2 (CD86), as well as co-stimulatory factors CD40, OX40, GITR, etc., with their ligands (Smith-Garvin, J. E., G. A. Koretzky, and M. S. Jordan, T cell activation. Annu Rev Immunol, 2009.27: p. 591-Ack. 619). In the absence of the co-stimulatory signal, T cells may undergo unresponsiveness (anergy) or programmed cell death (apoptosis) upon antigen stimulation.

CD40 is a member of the TNF receptor (TNFR) superfamily, expressed predominantly on a variety of antigen presenting cells such as B cell, dendritic cells (DC cells), monocytes and macrophages (Grewal, i. s. and r. a. Flavell, CD40 and CD154 in cell-mediated immunity, Annu Rev Immunol, 1998.16: p. 111-35). CD40 forms a trimer on the cell surface, with the cognate ligand CD40L (i.e., CD154) expressed predominantly on the activated T cell surface. The interaction of CD40 with CD40L is a co-stimulatory signal for T cell activation. CD40 involvement leads to a particular gene expression pattern, depending on the particular cell type. Binding of CD40 to CD40L on T cells can activate a variety of pathways, including NF-κB (nuclear factor κB), MAPK (mitogen-activated protein kinase) and STAT3 (signal transducer and transcriptional activator 3), among others (Rothe, M., et al, TRAF2-mediated activation of NF-kappa B by TNF receptor 2 and CD40. Science, 1995.269 (5229): p. 1424-7).

CD40 is not only expressed by normal immune cells, but also by many malignant cells. In particular, CD40 is overexpressed in: B-linage NHL, Chronic Lymphocytic Leukemia (CLL), Hairy Cell Leukemia (HCL), Hodgkin's disease, multiple myeloma, and bladder cancer, kidney cancer, ovary cancer, cervix cancer, breast cancer, lung cancer, nasopharynx cancer, and malignant melanoma, among others (Hassan, S. B., et al, Anti-CD40-mediated cancer immunology: an update of recovery and on clinical trials. immunopharmacological immunology, 2014.36 (2): p. 96-104).

CD40 agonist antibodies can act against tumor cells by a variety of mechanisms: firstly, CD40 agonist antibodies mediate a stronger anti-tumor effect by activating the immune system. Specifically, CD40 agonist antibodies can activate DC cells to increase their antigen presentation capacity as evidenced by increased expression of co-stimulatory molecules, such as the B7 family (CD80, CD86), and to promote cytokine secretion, such as interleukin 12, which would result in a significant T cell response (Fong, L. and E. G. Engleman, Dendritic cells in cancer immunology, Annu Rev Immunol, 2000.18: p. 245-73); the CD40 agonist antibody can promote the proliferation of resting B cells, immunoglobulin class switch, antibody secretion, and has an effect on the development of the germinal center and the survival of memory B cells, all of which are essential for humoral immune responses (Beatty, G. L., Y. Li, and K. B. Long, Cancer immunization: activating in and adaptive immunity through CD40 agonists. Ext Rev Anticancer Ther, 2017.17 (2): p 175-. Secondly, binding of CD40 agonist antibodies to CD40 expressed on the surface of tumor cells mediates antibody-dependent cellular cytotoxicity (ADCC) and direct clearance of tumor cells that highly express CD40 by killer cells (Von Derheide, R. H. and M. J. Glennie, inflammatory CD40 antibiotics and Cancer therapy, Clin Cancer Res, 2013.19 (5): p. 1035-43). Thirdly, CD40 agonist antibodies directly inhibit tumor growth and promote apoptosis upon binding to CD40 expressed on the surface of tumor cells, for example, the CD40/CD40L signaling pathway blocks the cell cycle of tumor cells, arresting the cell in G2-M phase, and the interaction of CD40/CD40L also promotes an elevation of Fas expression on the surface of tumor cells and inhibits growth and promotes apoptosis of tumor cells that highly express CD40 via the Fas/FasL signaling pathway (Eliopouls, A. G., et al, CD40 induces apoptosis in cancer cells through cancer activation of cytotoxicity ligands of the tumor necrosis factor superfamily Cell Biol, 2000.20 (15): p. 5503-15).

The agonist antibodies of CD40 can be divided into two classes according to their agonistic mode, the first class of CD40 agonistic activity is independent of Fc receptor crosslinking (such as CP-870893 and CDX-1140), although the former shows encouraging anti-cancer efficacy. However, there is dose-limiting toxicity, which causes the occurrence of systemic immune dysfunction, venous thromboembolism and Cytokine Release Syndrome (CRS). The other class will have CD40 agonistic activity relying on Fc receptor crosslinking. There are more tumor-associated inflammatory cells in tumor tissue and peripheral draining lymph nodes. FcγR2b receptor is more aggregated around tumor cells. Therefore, such "cross-linked antibody" agonists have higher tissue selectivity. And, thus, in tumor microenvironment antibodies can produce significant agonistic effect, while in normal tissue sites of the body, the capacity would be kept at low level and this may improve the therapeutic safety window.

Therefore, although there are some CD40 antibodies in the art already, such as CP870893 of Pfizer, there is still a need for new CD40 antibodies with comparable or better properties compared to existing antibodies, in particular CD40 antibodies relying on Fc receptor cross-linking, especially antibodies with better anti-cancer properties and greater safety.

DISCLOSURE OF INVENTION

The invention thus provides a novel antibody that binds to CD40 (particularly human CD40 or Rhesus CD40), and antigen-binding fragments thereof.

In some embodiments, the anti-CD40 antibodies or antigen-binding fragments thereof of the invention comprise a heavy chain variable region (VH), wherein the VH comprises
  (i) three Complementarity Determining Regions (CDRs) HCDR1, HCDR2 and HCDR3 contained in the VH shown in SEQ ID NOs:13, 58, 60, 62 or 14; or
  (ii) a sequence comprising at least one and no more than 5, 4, 3, 2 or 1 amino acid alteration (preferably amino acid substitutions, preferably conservative substitutions) in total on the three CDR regions relative to the sequence of (i), or
  (iii) a sequence comprising at least one and no more than 3, 2 or 1 amino acid alteration (preferably an amino acid substitution, preferably a conservative substitution) on HCDR3 relative to the sequence of (i).

In some embodiments, an anti-CD40 antibody or antigen-binding fragment thereof of the invention comprises a light chain variable region (VL), wherein the VL comprises:
  (i) three complementarity Determining Regions (CDRs) LCDR1, LCDR2 and LCDR3 contained in a VL as set forth in SEQ ID NOs:15, 64, 66 or 16; or
  (ii) a sequence comprising at least one and no more than 5, 4, 3, 2 or 1 amino acid alteration (preferably amino acid substitutions, preferably conservative substitutions) in total on the three CDR regions relative to the sequence of (i), or
  (iii) a sequence comprising at least one and no more than 3, 2 or 1 amino acid alteration (preferably an amino acid substitution, preferably a conservative substitution) on LCDR3 relative to the sequence of (i).

In some embodiments, the anti-CD40 antibodies or antigen-binding fragments thereof of the invention comprise a heavy chain variable region VH and a light chain variable region VL, wherein
  (a) the VH comprises
  (i) three Complementarity Determining Regions (CDRs) HCDR1, HCDR2 and HCDR3 contained in the VH shown in SEQ ID NOs:13, 58, 60, 62 or 14, or
  (ii) a sequence comprising at least one and no more than 5, 4, 3, 2 or 1 amino acid alteration (preferably amino acid substitution, preferably conservative substitution) in total on the three CDR regions relative to the sequence of (i);
  (iii) a sequence comprising at least one and no more than 3, 2 or 1 amino acid alteration (preferably an amino acid substitution, preferably a conservative substitution) on HCDR3 relative to the sequence of (i); and/or
  (b) the VL comprises:
  (i) three complementarity determining regions (CDRs) LCDR1, LCDR2 and LCDR3 contained in a VL as set forth in SEQ ID NOs:15, 64, 66 or 16; or
  (ii) a sequence comprising at least one and no more than 5, 4, 3, 2 or 1 amino acid alteration (preferably amino acid substitution, preferably conservative substitution) in total on the three CDR regions relative to the sequence of (i); or
  (iii) a sequence comprising at least one and no more than 3, 2 or 1 amino acid alteration (preferably an amino acid substitution, preferably a conservative substitution) on LCDR3 relative to the sequence of (i).

In some embodiments, the anti-CD40 antibodies or antigen-binding fragments thereof of the invention comprise a heavy chain variable region VH and/or a light chain variable region VL, wherein
  (a) the VH comprises
  (i) three complementarity determining regions (CDRs) HCDR1, HCDR2 and HCDR3 contained in the VH shown in SEQ ID NO:13, 58, 60 or 62, or
  (ii) a sequence comprising at least one and no more than 5, 4, 3, 2 or 1 amino acid alteration (preferably amino acid substitution, preferably conservative substitution) in total on the three CDR regions relative to the sequence of (i);
  (iii) a sequence comprising at least one and no more than 3, 2 or 1 amino acid alteration (preferably an amino acid substitution, preferably a conservative substitution) on HCDR3 relative to the sequence of (i); and/or
  (b) the VL comprises:
  (i) three complementarity determining regions (CDRs) LCDR1, LCDR2 and LCDR3 contained in a VL as shown in SEQ ID NOs:15, 64 or 66; or
  (ii) a sequence comprising at least one and no more than 5, 4, 3, 2 or 1 amino acid alteration (preferably amino acid substitution, preferably conservative substitution) in total on the three CDR regions relative to the sequence of (i); or
  (iii) a sequence comprising at least one and no more than 3, 2 or 1 amino acid alteration (preferably an amino acid substitution, preferably a conservative substitution) on LCDR3 relative to the sequence of (i).

In some embodiments, the anti-CD40 antibodies or antigen-binding fragments thereof of the invention comprise a heavy chain variable region VH and a light chain variable region VL, wherein
  (a) the VH comprises
  (i) three complementarity determining regions (CDRs) HCDR1, HCDR2 and HCDR3 contained in the VH shown in SEQ ID NO:14, or
  (ii) a sequence comprising at least one and no more than 5, 4, 3, 2 or 1 amino acid alteration (preferably amino acid substitution, preferably conservative substitution) in total on the three CDR regions relative to the sequence of (i);
  (iii) a sequence comprising at least one and no more than 3, 2 or 1 amino acid alteration (preferably an amino acid substitution, preferably a conservative substitution) on HCDR3 relative to the sequence of (i); and/or
  (b) the VL comprises:
  (i) three complementarity determining Regions (CDRs) LCDR1, LCDR2 and LCDR3 contained in the VL shown in SEQ ID NO:16; or
  (ii) a sequence comprising at least one and no more than 5, 4, 3, 2 or 1 amino acid alteration (preferably amino acid substitution, preferably conservative substitution) in total on the three CDR regions relative to the sequence of (i); or
  (iii) a sequence comprising at least one and no more than 3, 2 or 1 amino acid alteration (preferably an amino acid substitution, preferably a conservative substitution) on LCDR3 relative to the sequence of (i).

In a preferred embodiment, the VH comprises or consists of an amino acid sequence selected from the group consisting of those shown as SEQ ID NOs:13, 58, 60, 62 or 14.

In a preferred embodiment, the VL comprises or consists of an amino acid sequence selected from the group consisting of those shown in SEQ ID NOs:15, 64, 66 or 16.

In a preferred embodiment, the anti-CD40 antibodies or antigen-binding fragments thereof of the invention comprise 3 complementarity determining region HCDRs of the heavy chain variable region as set forth in SEQ ID NO:13, 58, 60, 62 or 14, and the 3 complementarity determining region LCDRs of the light chain variable region as set forth in SEQ ID NO:15, 64, 66 or 16.

In a preferred embodiment, the anti-CD40 antibodies or antigen-binding fragments thereof of the invention comprise 3 complementarity determining region HCDRs of the heavy chain variable region as set forth in SEQ ID NO:13, 58, 60 or 62 and the 3 complementarity determining region LCDRs of the light chain variable region as set forth in SEQ ID NO:15, 64 or 66.

In a preferred embodiment, the anti-CD40 antibodies or antigen-binding fragments thereof of the invention comprise 3 complementarity determining region HCDRs of the heavy chain variable region shown as SEQ ID NOs. 14 and 3 complementarity determining region LCDRs of the light chain variable region shown as SEQ ID NO: 16.

In a preferred embodiment, the anti-CD40 antibody or antigen-binding fragment thereof of the invention comprises:
(i) 3 CDRs HCDR1, HCDR2 and HCDR3 of the heavy chain variable region shown in SEQ ID NO: 13 and the 3 CDRs LCDR1, LCDR2 and LCDR3 of the light chain variable region shown in SEQ ID NO: 15;
(ii) 3 CDRs HCDR1, HCDR2 and HCDR3 of the heavy chain variable region shown as SEQ ID NO: 58 and 3 CDRs LCDR1, LCDR2 and LCDR3 of the light chain variable region shown as SEQ ID NO: 64;
(iii) 3 CDRs HCDR1, HCDR2 and HCDR3 of the heavy chain variable region shown as SEQ ID NO:60 or 62 and the 3 CDRs LCDR1, LCDR2 and LCDR3 of the light chain variable region shown as SEQ ID NO:66;
(iv) 3 CDRs HCDR1, HCDR2 and HCDR3 of the heavy chain variable region shown in SEQ ID NO: 14 and 3 CDRs LCDR1, LCDR2 and LCDR3 of the light chain variable region shown in SEQ ID NO: 16;
(v) a CDR combination of any one of (i)-(iv) wherein at least one and not more than 3, 2 or 1 amino acid alteration (preferably amino acid substitution, preferably conservative substitution) is comprised in the sequence compared to HCDR3 and/or LCDR 3.

In some embodiments, the anti-CD40 antibodies or antigen-binding fragments thereof of the invention comprise a heavy chain variable region (VH) and/or a light chain variable region (VL), wherein
(i) Said VH comprises Complementarity Determining Regions (CDRs) HCDR1, HCDR2 and HCDR3, wherein HCDR1 comprises or consists of the amino acid sequence of SEQ ID NO:1 or 2, or HCDR1 comprises an amino acid sequence having one, two or three alterations (preferably amino acid substitutions, preferably conservative substitutions) as compared to the amino acid sequence of SEQ ID NO:1 or 2; the HCDR2 comprises or consists of the amino acid sequence of SEQ ID NO: 3 or 4 or the HCDR2 comprises an amino acid sequence having one, two or three changes (preferably amino acid substitutions, preferably conservative substitutions) as compared to the amino acid sequence selected from SEQ ID NO: 3 or 4; the HCDR3 comprises or consists of the amino acid sequence of SEQ ID NO: 5, 51, 52, 55 or 6 or the HCDR3 comprises an amino acid sequence having one, two or three changes (preferably amino acid substitutions, preferably conservative substitutions) compared to the amino acid sequence of SEQ ID NO: 5, 51, 52, 55 or 6;

and/or
(ii) wherein said VL comprises Complementarity Determining Regions (CDRs) LCDR1, LCDR2 and LCDR3, wherein LCDR1 comprises or consists of the amino acid sequence of SEQ ID NO: 7 or 8, or LCDR1 comprises an amino acid sequence having one, two or three alterations (preferably amino acid substitutions, preferably conservative substitutions) as compared to the amino acid sequence of SEQ ID NO: 7 or 8; LCDR2 comprises or consists of the amino acid sequence of SEQ ID NO: 9 or 10 or LCDR2 comprises an amino acid sequence having one, two or three changes (preferably amino acid substitutions, preferably conservative substitutions) compared to the amino acid sequence of SEQ ID NO: 9 or 10; the LCDR3 comprises or consists of an amino acid sequence selected from SEQ ID NO: 11, 53, 54, 56 or 12, or the LCDR3 comprises an amino acid sequence having one, two or three changes (preferably amino acid substitutions, preferably conservative substitutions) compared to the amino acid sequence of SEQ ID NO: 11, 53, 54, 56 or 12.

In a preferred embodiment, the present invention provides an anti-CD40 antibody or antigen binding fragment thereof comprising a heavy chain variable region (VH) and a light chain variable region (VL), wherein
(a) the VH comprises
(i) HCDR1, HCDR2 and HCDR3 comprising or consisting of the following sequence: SEQ ID NO:1, SEQ ID NO:3 and SEQ ID NO:5; or
(ii) HCDR1, HCDR2 and HCDR3 comprising or consisting of the following sequence: SEQ ID NO:1, SEQ ID NO:3 and SEQ ID NO:51; or
(iii) HCDR1, HCDR2 and HCDR3 comprising or consisting of the following sequence: SEQ ID NO:1, SEQ ID NO:3 and SEQ ID NO:52; or
(iv) HCDR1, HCDR2 and HCDR3 comprising or consisting of the following sequence: SEQ ID NO:2, SEQ ID NO:4 and SEQ ID NO:6; or
(v) the HCDR combination of any one of (i) to (iv) wherein there is at least one and no more than 5, 4, 3, 2 or 1 amino acid alteration (preferably an amino acid substitution, preferably a conservative substitution) in total on the three CDR regions; or
(vi) the HCDR combination of any one of (i) to (iv), wherein at least one and not more than 3, 2 or 1 amino acid alteration (preferably an amino acid substitution, preferably a conservative substitution) is comprised in HCDR 3;
And/or
(b) said VL comprising
(i) LCDR1, LCDR2 and LCDR3 comprising or consisting of the following sequence: SEQ ID NO:7, SEQ ID NO:9 and SEQ ID NO:11 or
(ii) LCDR1, LCDR2 and LCDR3 comprising or consisting of the following sequence: SEQ ID NO:7, SEQ ID NO:9 and SEQ ID NO:53; or
(iii) LCDR1, LCDR2 and LCDR3 comprising or consisting of the following sequence: SEQ ID NO:7, SEQ ID NO:9 and SEQ ID NO:54; or
(iv) LCDR1, LCDR2 and LCDR3 comprising or consisting of the following sequence: SEQ ID NO:8, SEQ ID NO:10 and SEQ ID NO:12 or
(v) the LCDR combination of any one of (i)-(iv) wherein there is at least one and no more than 5, 4, 3, 2 or 1 amino acid alteration (preferably an amino acid substitution, preferably a conservative substitution) in total on the three CDR regions; or
(vi) the LCDR combination of any one of (i)-(iv), wherein at least one and not more than 3, 2 or 1 amino acid alteration (preferably an amino acid substitution, preferably a conservative substitution) is comprised in HCDR 3.

In a preferred embodiment, the present invention provides an anti-CD40 antibody or antigen binding fragment thereof comprising a heavy chain variable region (VH) and a light chain variable region (VL), wherein
(a) The VH comprises
(i) HCDR1, HCDR2 and HCDR3 comprising or consisting of the following sequence: SEQ ID NO:1, SEQ ID NO:3 and SEQ ID NO:5; or
(ii) HCDR1, HCDR2 and HCDR3 comprising or consisting of the following sequence: SEQ ID NO:1, SEQ ID NO:3 and SEQ ID NO:51; or
(iii) HCDR1, HCDR2 and HCDR3 comprising or consisting of the following sequence: SEQ ID NO:1, SEQ ID NO:3 and SEQ ID NO:52; or
(iv) the HCDR combination of any one of (i)-(iii) wherein there is at least one and no more than 5, 4, 3, 2 or 1 amino acid alteration (preferably an amino acid substitution, preferably a conservative substitution) in total on the three CDR regions; or
(v) the HCDR combination of any one of (i)-(iii), wherein at least one and not more than 3, 2 or 1 amino acid alteration (preferably an amino acid substitution, preferably a conservative substitution) is comprised in HCDR 3;
and/or
(b) said VL comprising
(i) LCDR1, LCDR2 and LCDR3 comprising or consisting of the following sequence: SEQ ID NO:7, SEQ ID NO:9 and SEQ ID NO:11 or
(ii) LCDR1, LCDR2 and LCDR3 comprising or consisting of the following sequence: SEQ ID NO:7, SEQ ID NO:9 and SEQ ID NO:53; or
(iii) LCDR1, LCDR2 and LCDR3 comprising or consisting of the following sequence: SEQ ID NO:7, SEQ ID NO:9 and SEQ ID NO:54; or
(iv) the LCDR combination of any one of (i)-(iii) wherein there is at least one and no more than 5, 4, 3, 2 or 1 amino acid alteration (preferably an amino acid substitution, preferably a conservative substitution) in total on the three CDR regions; or
(v) the LCDR combination of any one of (i)-(iii), wherein at least one and not more than 3, 2 or 1 amino acid alteration (preferably an amino acid substitution, preferably a conservative substitution) is comprised in said LCDR 3.

In a preferred embodiment, the present invention provides an anti-CD40 antibody or antigen binding fragment thereof comprising a heavy chain variable region (VH) and a light chain variable region (VL), wherein
(a) the VH comprises
(i) HCDR1, HCDR2 and HCDR3 comprising or consisting of the following sequence: SEQ ID NO:2, 4 and 6; or
(ii) the HCDR combination of (i) wherein there is at least one and no more than 5, 4, 3, 2 or 1 amino acid alteration (preferably an amino acid substitution, preferably a conservative substitution) in total on the three CDR regions; or
(iii) the combination of HCDR of (i), wherein at least one and not more than 3, 2 or 1 amino acid alteration (preferably an amino acid substitution, preferably a conservative substitution) is comprised in said HCDR 3;
and/or
(b) said VL comprising
(i) LCDR1, LCDR2 and LCDR3 comprising or consisting of the following sequence: SEQ ID NO:8, 10 and 12; or
(ii) the LCDR combination of (i) wherein there is at least one and no more than 5, 4, 3, 2 or 1 amino acid alteration (preferably an amino acid substitution, preferably a conservative substitution) in total on the three CDR regions; or
(iii) the LCDR combination of (i), wherein at least one and no more than 3, 2 or 1 amino acid alteration (preferably an amino acid substitution, preferably a conservative substitution) is comprised in said LCDR 3.

In a preferred embodiment, the present invention provides an anti-CD40 antibody or antigen binding fragment thereof comprising
(i) HCDR1, HCDR2 and HCDR3 comprising or consisting of the following sequence: SEQ ID NO:1, SEQ ID NO:3 and SEQ ID NO:5, and LCDR1, LCDR2 and LCDR3 comprising or consisting of the following sequence: SEQ ID NO:7, SEQ ID NO:9 and SEQ ID NO:11; or
(ii) HCDR1, HCDR2 and HCDR3 comprising or consisting of the following sequence: SEQ ID NO:1, SEQ ID NO:3 and SEQ ID NO:51, and LCDR1, LCDR2 and LCDR3 comprising or consisting of the following sequence: SEQ ID NO:7, SEQ ID NO:9 and SEQ ID NO:53; or
(iii) HCDR1, HCDR2 and HCDR3 comprising or consisting of the following sequence: SEQ ID NO:1, SEQ ID NO:3 and SEQ ID NO:52, and/or LCDR1, LCDR2 and LCDR3 comprising or consisting of the following sequence: SEQ ID NO:7, SEQ ID NO:9 and SEQ ID NO:54; or
(iv) HCDR1, HCDR2 and HCDR3 comprising or consisting of the following sequence: SEQ ID NO:2, SEQ ID NO:4 and SEQ ID NO:6, and LCDR1, LCDR2 and LCDR3 comprising or consisting of the following sequence: SEQ ID NO:8, SEQ ID NO:10 and SEQ ID NO:12 SEQ ID NO;
(v) the HCDR and LCDR combination of any one of (i)-(iv) wherein there is at least one and not more than 5, 4, 3, 2 or 1 amino acid alteration (preferably an amino acid substitution, preferably a conservative substitution) in total on said three HCDR regions and/or on said three LCDR regions; or
(vi) the HCDR and LCDR combination of any one of (i) to (iv), wherein at least one and no more than 3, 2 or 1 amino acid alteration (preferably an amino acid substitution, preferably a conservative substitution) is comprised in said HCDR3 and/or LCDR 3.

In a preferred embodiment, the present invention provides an anti-CD40 antibody or antigen binding fragment thereof comprising a heavy chain variable region (VH) and a light chain variable region (VL), wherein
(a) the VH comprises
(i) HCDR1, HCDR2 and HCDR3 comprising or consisting of the following sequence: SEQ ID NO:1, 3 and 55; or
(ii) the HCDR combination of (i), wherein at least one and no more than 5, 4, 3, 2 or 1 amino acid alteration (preferably an amino acid substitution, preferably a conservative substitution) is included in total on the three HCDR regions;
and/or
(b) said VL comprising
(iii) LCDR1, LCDR2 and LCDR3 comprising or consisting of the following sequence: SEQ ID NO:7, 9 and 56; or
(iv) the LCDR combination of (i), wherein at least one and no more than 5, 4, 3, 2, or 1 amino acid alteration (preferably an amino acid substitution, preferably a conservative substitution) is included in total on the three LCDR regions.

In some embodiments, the amino acid sequence set forth in SEQ ID NO:55 is as follows:
A-R-E-R-V-G-A-X1-P-T-Y-Y-Y-X2-X3-DV, wherein X1, X2 or X3 may be any amino acid, preferably wherein X1 may be T, N, W, K, A or Y, more preferably T or N; wherein X2 is preferably W or Y; wherein X3 can be W, Y, M, F, T, more preferably M, W or Y In some embodiments, the amino acid sequence set forth in SEQ ID NO:56 is as follows:

M-X1-X2-L-X3-X4-P-Y-T, wherein X1, X2, X3 and X4 can be any amino acid, preferably wherein X1 can be Q, N or P, more preferably Q or N; x2 can be G, Q, F, S, Y or M; more preferably G or Q; x3 can be E, N, T, S or K; more preferably E or N; x4 can be T, Q, V, L, P or E; more preferably T, Q or V.

In a preferred embodiment, the invention provides an anti-CD40 antibody or antigen-binding fragment thereof comprising a heavy chain variable region (VH) and a light chain variable region (VL), wherein the VH comprises Complementarily Determining Regions (CDRs) HCDR1, HCDR2 and HCDR3 and the VL Comprises (CDRs) LCDR1, LCDR2 and LCDR3, wherein the antibody or antigen-binding fragment thereof comprises a combination of HCDR1, HCDR2, HCDR3, LCDR1, LCDR2 and LCDR3 as set forth in the following table (table A):

TABLE A

Exemplary combinations of HCDR1, HCDR2, HCDR3, LCDR1, LCDR2, and LCDR3 in antibodies or antigen-binding fragments thereof of the invention

| Combination | HCDR1 comprising or consisting of the amino acid sequence shown in SEQ ID NO | HCDR2 comprising or consisting of the amino acid sequence shown in SEQ ID NO | HCDR3 comprising or consisting of the amino acid sequence shown in SEQ ID NO | LCDR1 comprising or consisting of the amino acid sequence set forth in SEQ ID NO | LCDR2 comprising or consisting of the amino acid sequence set forth in SEQ ID NO | LCDR3 comprising or consisting of the amino acid sequence set forth in SEQ ID NO |
|---|---|---|---|---|---|---|
| (1) | SEQ ID NO: 1 | SEQ ID NO: 3 | SEQ ID NO: 5 | SEQ ID NO: 7 | SEQ ID NO: 9 | SEQ ID NO: 11 |
| (2) | SEQ ID NO: 1 | SEQ ID NO: 3 | SEQ ID NO: 51 | SEQ ID NO: 7 | SEQ ID NO: 9 | SEQ ID NO: 53 |
| (3) | SEQ ID NO: 1 | SEQ ID NO: 3 | SEQ ID NO: 52 | SEQ ID NO: 7 | SEQ ID NO: 9 | SEQ ID NO: 54 |
| (4) | SEQ ID NO: 1 | SEQ ID NO: 3 | SEQ ID NO: 55 | SEQ ID NO: 7 | SEQ ID NO: 9 | SEQ ID NO: 56 |
| (5) | SEQ ID NO: 2 | SEQ ID NO: 4 | SEQ ID NO: 6 | SEQ ID NO: 8 | SEQ ID NO: 10 | SEQ ID NO: 12 |

In some embodiments, the anti-CD40 antibodies or antigen-binding fragments thereof of the invention comprise a heavy chain variable region VH and/or a light chain variable region VL, wherein, (a) The heavy chain variable region VH (i) Comprises or consists of an amino acid sequence having at least 90%, 91%, 92%, 93%, 94%, 95%, 96%, 97%, 98% or 99% identity with an amino acid sequence selected from SEQ ID NO:13, 58, 60, 62 or 14, or (ii) Comprises or consists of an amino acid sequence selected from SEQ ID NO:13, 58, 60, 62 or 14; or (iii) Comprises an amino acid sequence having 1 or more (preferably no more than 10, more preferably no more than 5, 4, 3, 2, 1) amino acid alterations (preferably amino acid substitutions, more preferably amino acid conservative substitutions) as compared to an amino acid sequence selected from the group consisting of SEQ ID NOs:13, 58, 60, 62 and 14, preferably the amino acid alterations do not occur in the CDR regions, preferably the amino acid alterations occur in the FR regions;

And/or (b) The light chain variable region VL (i) comprises or consists of an amino acid sequence having at least 90%, 91%, 92%, 93%, 94%, 95%, 96%, 97%, 98% or 99% identity with an amino acid sequence selected from the group consisting of SEQ ID NO:15, 64, 66 and 16;

(ii) comprises or consists of an amino acid sequence selected from SEQ ID NO:15, 64, 66 or 16; or (iii) comprises an amino acid sequence having 1 or more (preferably no more than 10, more preferably no more than 5, 4, 3, 2, 1) amino acid alterations (preferably amino acid substitutions, more preferably amino acid conservative substitutions) as compared to an amino acid sequence selected from the group consisting of SEQ ID NO:15, 64, 66 and 16, preferably the amino acid alterations do not occur in the CDR regions, preferably the amino acid alterations occur in the FR regions.

In some embodiments, the heavy chain variable region VH of the anti-CD40 antibodies or antigen-binding fragments thereof of the invention (i) comprises or consists of an amino acid sequence having at least 90%, 91%, 92%, 93%, 94%, 95%, 96%, 97%, 98% or 99% identity with an amino acid sequence selected from SEQ ID NO:13, 58, 60 or 62, or (ii) comprises or consists of an amino acid sequence selected from the group consisting of SEQ ID NO:13, 58, 60 and 62; or (iii) comprises an amino acid sequence having 1 or more (preferably not more than 10, more preferably not more than 5, 4, 3, 2, 1) amino acid alterations (preferably amino acid substitutions, more preferably amino acid conservative substitutions) as compared to an amino acid sequence selected from the group consisting of SEQ ID NO:13, 58, 60 or 62, preferably the amino acid alterations do not occur in the CDR regions, preferably the amino acid alterations occur in the FR regions.

In some embodiments, the light chain variable region VL of the anti-CD40 antibodies or antigen binding fragments thereof of the invention (i) comprises or consists of an amino acid sequence having at least 90%, 91%, 92%, 93%, 94%, 95%, 96%, 97%, 98% or 99% identity with an amino acid sequence selected from SEQ ID NO:15, 64 or 66;

(ii) comprises or consists of an amino acid sequence selected from SEQ ID NO:15, 64 or 66; or (iii) comprises an amino acid sequence having 1 or more (preferably no more than 10, more preferably no more than 5, 4, 3, 2, 1) amino acid alterations (preferably amino acid substitutions, more preferably amino acid conservative substitutions) as compared to an amino acid sequence selected from the group consisting of SEQ ID NO:15, 64 or 66, preferably said amino acid alterations do not occur in the CDR regions, preferably said amino acid alterations occur in the FR regions.

In some embodiments, the heavy chain variable region VH of the anti-CD40 antibodies or antigen-binding fragments thereof of the invention
(i) comprising or consisting of an amino acid sequence having at least 90%, 91%, 92%, 93%, 94%, 95%, 96%, 97%, 98% or 99% identity with an amino acid sequence selected from SEQ ID NO:14, or
(ii) comprises or consists of an amino acid sequence selected from SEQ ID NO:14; or
(iii) comprising an amino acid sequence having 1 or more (preferably not more than 10, more preferably not more than 5, 4, 3, 2, 1) amino acid alterations (preferably amino acid substitutions, more preferably amino acid conservative substitutions) as compared to an amino acid sequence selected from the group consisting of SEQ ID NO:14, preferably said amino acid alterations do not occur in the CDR regions, preferably said amino acid alterations occur in the FR regions.

In some embodiments, the light chain variable region VL of the anti-CD40 antibodies or antigen binding fragments thereof of the invention
(i) comprises or consists of an amino acid sequence having at least 90%, 91%, 92%, 93%, 94%, 95%, 96%, 97%, 98% or 99% identity with an amino acid sequence selected from SEQ ID NO: 16;
(ii) comprises or consists of an amino acid sequence selected from the group consisting of SEQ ID NO:16; or
(iii) comprising an amino acid sequence having 1 or more (preferably no more than 10, more preferably no more than 5, 4, 3, 2, 1) amino acid alterations (preferably amino acid substitutions, more preferably amino acid conservative substitutions) compared to an amino acid sequence selected from the group consisting of SEQ ID NO:16, preferably said amino acid alterations do not occur in the CDR regions, preferably said amino acid alterations occur in the FR regions.

In some embodiments, the anti-CD40 antibodies or antigen-binding fragments thereof of the invention comprise a heavy chain variable region VH and/or a light chain variable region VL, wherein,
(i) the heavy chain variable region VH comprises or consists of the amino acid sequence of SEQ ID NO: 13 and the light chain variable region VL comprises or consists of the amino acid sequence of SEQ ID NO: 15;
(ii) the heavy chain variable region VH comprises or consists of the amino acid sequence of SEQ ID NO:58 and the light chain variable region VL comprises or consists of the amino acid sequence of SEQ ID NO:64;
(iii) the heavy chain variable region VH comprises or consists of the amino acid sequence of SEQ ID NO: 60 and the light chain variable region VL comprises or consists of the amino acid sequence of SEQ ID NO: 66;
(iv) the heavy chain variable region VH comprises or consists of the amino acid sequence of SEQ ID NO:62 and the light chain variable region VL comprises or consists of the amino acid sequence of SEQ ID NO:66;
(v) the heavy chain variable region VH comprises or consists of the amino acid sequence of SEQ ID NO: 14 and the light chain variable region VL comprises or consists of the amino acid sequence of SEQ ID NO: 16.

In some embodiments, the amino acid sequence of the heavy chain variable region of the antibody of the invention is at least 90%, 91%, 92%, 93%, 94%, 95%, 96%, 97%, 98% or 99% identical to, or comprises 1 or more (preferably no more than 10, more preferably no more than 5, 4, 3, 2, 1) amino acid alterations (preferably amino acid substitutions, more preferably amino acid conservative substitutions) as compared to the amino acid sequence of the heavy chain variable region of (i)-(v) described above, preferably the amino acid alterations do not occur in the CDR regions, preferably the amino acid alterations occur in the FR regions.

In some embodiments, the amino acid sequence of the light chain variable region of the antibody of the invention is at least 90%, 91%, 92%, 93%, 94%, 95%, 96%, 97%, 98% or 99% identical to, or comprises 1 or more (preferably no more than 10, more preferably no more than 5, 4, 3, 2, 1) amino acid alterations (preferably amino acid substitutions, more preferably amino acid conservative substitutions) as compared to the amino acid sequence of the light chain variable region of (i)-(v) described above, preferably the amino acid alterations do not occur in the CDR regions, preferably the amino acid alterations occur in the FR regions.

In a preferred embodiment, the invention provides an anti-CD40 antibody or antigen-binding fragment thereof comprising a heavy chain variable region (VH) and a light chain variable region (VL), wherein the antibody or antigen-binding fragment thereof comprises a combination of a heavy chain variable region VH and a light chain variable region VL as shown in the following table (table B):

TABLE B exemplary combinations of heavy chain variable region VH and light chain variable region VL in an antibody or antigen binding fragment thereof of the invention

| Combination | VH comprising or consisting of the amino acid sequence shown in the following SEQ ID NO | VL comprising or consisting of the amino acid sequence shown in the following SEQ ID NO |
| --- | --- | --- |
| (1) | SEQ ID NO: 13 | SEQ ID NO: 15 |
| (2) | SEQ ID NO: 58 | SEQ ID NO: 64 |
| (3) | SEQ ID NO: 60 | SEQ ID NO: 66 |
| (4) | SEQ ID NO: 62 | SEQ ID NO: 66 |
| (5) | SEQ ID NO: 14 | SEQ ID NO: 16 |

In some embodiments, the anti-CD40 antibodies or antigen-binding fragments thereof of the invention comprise a heavy chain and/or a light chain, wherein
(a) the heavy chain
(i) comprises or consists of an amino acid sequence having at least 85%, 90%, 91%, 92%, 93%, 94%, 95%, 96%, 97%, 98% or 99% identity with an amino acid sequence selected from the group consisting of SEQ ID NO:17, 18, 19, 67, 69, 70 and 20;
(ii) comprises or consists of an amino acid sequence selected from the group consisting of SEQ ID NO:17, 18, 19, 67, 69, 70 and 20; or
(iii) comprises an amino acid sequence having 1 or more (preferably no more than 20 or 10, more preferably no more than 5, 4, 3, 2, 1) amino acid alterations (preferably an amino acid substitution, more preferably an amino acid conservative substitution) as compared to an amino acid sequence selected from the group consisting of SEQ ID NOs:17, 18, 19, 67, 69, 70 and 20, preferably the amino acid alterations do not occur in the CDR region of the heavy chain, more preferably the amino acid alterations do not occur in the heavy chain variable region, most preferably the amino acid alterations occur in the constant region of the heavy chain; and/or (b) the light chains (i) comprises or consists of an amino acid sequence having at least 85%, 90%, 91%, 92%, 93%, 94%, 95%, 96%, 97%, 98% or 99% identity with an amino acid sequence selected from the group consisting of SEQ ID NO:21, 68, 71 and 22;

(ii) comprises or consists of an amino acid sequence selected from SEQ ID NO:21, 68, 71 or 22; or (iii) comprises an amino acid sequence having 1 or more (preferably no more than 20 or 10, more preferably no more than 5, 4, 3, 2, 1) amino acid alterations (preferably an amino acid substitution, more preferably an amino acid conservative substitution) as compared to an amino acid sequence selected from the group consisting of SEQ ID NOs: 21, 68, 71 and 22, preferably the amino acid alterations do not occur in the CDR region of the light chain, more preferably the amino acid alterations do not occur in the light chain variable region, most preferably the heavy chain amino acid alterations occur in the light chain constant region.

In some embodiments, the heavy chain of the anti-CD40 antibodies or antigen-binding fragments thereof of the invention\

(i) comprises or consists of an amino acid sequence having at least 85%, 90%, 91%, 92%, 93%, 94%, 95%, 96%, 97%, 98% or 99% identity with an amino acid sequence selected from the group consisting of SEQ ID NO:17, 18, 19, 67, 69 and 70;

(ii) comprises or consists of an amino acid sequence selected from the group consisting of SEQ ID NO:17, 18, 19, 67, 69 and 70; or (iii) comprises an amino acid sequence having 1 or more (preferably no more than 20 or 10, more preferably no more than 5, 4, 3, 2, 1) amino acid alterations (preferably an amino acid substitution, more preferably an amino acid conservative substitution) as compared to an amino acid sequence selected from the group consisting of SEQ ID NOs: 17, 18, 19, 67, 69 and 70, preferably the amino acid alterations do not occur in the CDR region of the heavy chain, more preferably the amino acid alterations do not occur in the heavy chain variable region, most preferably the heavy chain amino acid alterations occur in the heavy chain constant region.

In some embodiments, the anti-CD40 antibodies or antigen-binding fragments thereof of the invention comprise a light chain (i) comprises or consists of an amino acid sequence having at least 85%, 90%, 91%, 92%, 93%, 94%, 95%, 96%, 97%, 98% or 99% identity with an amino acid sequence selected from the group consisting of SEQ ID NO:21, 68 and 71;

(ii) comprises or consists of an amino acid sequence selected from SEQ ID NO:21, 68 or 71; or (iii) comprises an amino acid sequence having 1 or more (preferably no more than 20 or 10, more preferably no more than 5, 4, 3, 2, 1) amino acid alterations (preferably an amino acid substitution, more preferably an amino acid conservative substitution) as compared to an amino acid sequence selected from the group consisting of SEQ ID NO:21, 68 and 71, preferably the amino acid alterations do not occur in the CDR region of the light chain, more preferably the amino acid alterations do not occur in the light chain variable region, most preferably the heavy chain amino acid alterations occur in the light chain constant region.

In some embodiments, the heavy chain of the anti-CD40 antibodies or antigen-binding fragments thereof of the invention (i) comprises or consists of an amino acid sequence having at least 85%, 90%, 91%, 92%, 93%, 94%, 95%, 96%, 97%, 98% or 99% identity with an amino acid sequence selected from SEQ ID NO:20;

(ii) comprises or consists of an amino acid sequence selected from SEQ ID NO:20; or (iii) an amino acid sequence comprising 1 or more (preferably no more than 20 or 10, more preferably no more than 5, 4, 3, 2, 1) amino acid alterations (preferably amino acid substitutions, more preferably amino acid conservative substitutions) as compared to an amino acid sequence selected from SEQ ID NO: 20, preferably the amino acid alterations do not occur in the CDR regions of the heavy chain, more preferably the amino acid alterations do not occur in the heavy chain variable region, most preferably the heavy chain amino acid alterations occur in the heavy chain constant region.

In some embodiments, the anti-CD40 antibodies or antigen-binding fragments thereof of the invention comprise a light chain (i) comprises or consists of an amino acid sequence having at least 85%, 90%, 91%, 92%, 93%, 94%, 95%, 96%, 97%, 98% or 99% identity with an amino acid sequence selected from SEQ ID NO:22;

(ii) comprises or consists of an amino acid sequence selected from SEQ ID NO:22; or (iii) an amino acid sequence comprising 1 or more (preferably no more than 20 or 10, more preferably no more than 5, 4, 3, 2, 1) amino acid alterations (preferably an amino acid substitution, more preferably an amino acid conservative substitution) as compared to the amino acid sequence selected from the group consisting of SEQ ID NO: 22, preferably the amino acid alteration does not occur in the CDR region of the light chain, more preferably the amino acid alteration does not occur in the light chain variable region, most preferably the heavy chain amino acid alteration occurs in the light chain constant region.

In some embodiments, the anti-CD40 antibodies or antigen-binding fragments thereof of the invention comprise a heavy chain and/or a light chain, wherein, (i) the heavy chain comprises or consists of the amino acid sequence of SEQ ID NO:17, 18, 19, 67, 69 or 70 and the light chain comprises or consists of the amino acid sequence of SEQ ID NO:21, 68 or 71, (ii) the heavy chain comprises or consists of the amino acid sequence of SEQ ID NO:17, 18 or 19 and the light chain comprises or consists of the amino acid sequence of SEQ ID NO:21;

(iii) the heavy chain comprises or consists of the amino acid sequence of SEQ ID NO:67 and the light chain comprises or consists of the amino acid sequence of SEQ ID NO:68;

(iv) the heavy chain comprises or consists of the amino acid sequence of SEQ ID NO:69 or 70 and the light chain comprises or consists of the amino acid sequence of SEQ ID NO:71;

(v) the heavy chain comprises or consists of the amino acid sequence of SEQ ID NO: 20 and the light chain comprises or consists of the amino acid sequence of SEQ ID NO: 22.

In some embodiments, the amino acid sequence of the heavy chain of the antibody of the invention has at least 85%, 90%, 91%, 92%, 93%, 94%, 95%, 96%, 97%, 98% or 99% identity with the amino acid sequence of a heavy chain in the above (i)-(v), or its amino acid sequence comprises 1 or more (preferably no more than 20 or 10, more preferably no more than 5, 4, 3, 2, 1) amino acid alterations (preferably amino acid substitutions, more preferably amino acid conservative substitutions) as compared to the amino acid sequence of a heavy chain in the above (i)-(v), preferably the amino acid alterations do not occur in the CDR regions of the heavy chain, more preferably the amino acid alterations do not occur in the variable region of the heavy chain, most preferably the amino acid alterations occur in the constant region of the heavy chain.

In some embodiments, the amino acid sequence of the light chain of the antibody of the invention has at least 85%, 90%, 91%, 92%, 93%, 94%, 95%, 96%, 97%, 98% or 99% identity with the amino acid sequence of a heavy chain in the above (i)-(v), or its amino acid sequence comprises 1 or more (preferably no more than 20 or 10, more preferably no more than 5, 4, 3, 2, 1) amino acid alterations (preferably amino acid substitutions, more preferably amino acid conservative substitutions) as compared to the amino acid sequence of a light chain in the above (i)-(v), preferably the amino acid alterations do not occur in the CDR regions of the light chain, more preferably the amino acid alterations do not occur in the light chain variable region, most preferably the amino acid alterations occur in the constant region of the light chain.

In a preferred embodiment, the present invention provides an anti-CD40 antibody or antigen-binding fragment thereof comprising a heavy chain and a light chain, wherein the antibody or antigen-binding fragment thereof comprises a combination of heavy and light chains as set forth in the following table (table C):

TABLE C

Exemplary combinations of heavy and light chains in an antibody or antigen-binding fragment thereof of the invention

| Combination | Heavy chain comprising or consisting of the amino acid sequence shown in the following SEQ ID NO | A light chain comprising or consisting of the amino acid sequence set forth in the following SEQ ID NO |
|---|---|---|
| (1) | SEQ ID NO: 17 | SEQ ID NO: 21 |
| (2) | SEQ ID NO: 18 | SEQ ID NO: 21 |
| (3) | SEQ ID NO: 19 | SEQ ID NO: 21 |
| (4) | SEQ ID NO: 67 | SEQ ID NO: 68 |
| (5) | SEQ ID NO: 69 | SEQ ID NO: 71 |
| (6) | SEQ ID NO: 70 | SEQ ID NO: 71 |
| (4) | SEQ ID NO: 20 | SEQ ID NO: 22 |

In some embodiments, the heavy and/or light chain of the anti-CD40 antibody or fragment thereof of the invention further comprises a signal peptide sequence, e.g., the signal peptide sequence comprises or consists of the amino acid sequence set forth in SEQ ID NO: 43.

In one embodiment of the invention, the amino acid alterations described herein comprise amino acid substitutions, insertions or deletions. Preferably, the amino acid alterations described herein are amino acid substitutions, preferably conservative substitutions.

In some embodiments, the alteration occurs in a CDR region (particularly a CDR3 region) of the heavy and/or light chain of the antibody. In some embodiments, there may be 1, 2, or 3 alterations in a CDR region, for example, the CDR3 region.

In a preferred embodiment, the amino acid alterations described herein occur in regions outside the CDRs (e.g., in the FRs). In certain embodiments, the alteration occurs in an FR region of an antibody, e.g., an FR region of a heavy and/or light chain variable region of an antibody, e.g., an FR1, FR2, FR2, or F4 region. In some embodiments, the alteration occurs in the FR2 region. In some embodiments, there may be 1, 2, or 3 alterations in the FR region.

More preferably, the amino acid alterations according to the invention occur in regions outside the heavy chain variable region and/or outside the light chain variable region, for example in the constant region of the heavy and/or light chain.

In some embodiments, the substitution is a conservative substitution. Conservative substitutions are those substitutions of one amino acid by another within the same class, for example, one acidic amino acid is substituted by another acidic amino acid, one basic amino acid is substituted by another basic amino acid, or one neutral amino acid is substituted by another neutral amino acid. Exemplary substitutions are shown in table D below:

TABLE D

| Original residue | Exemplary substitutions | Preferred conservative amino acid substitutions |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu, |
| Cys (C) | Ser, Ala | Ser |
| Gln (Q) | Asn, Glu | Asn, |
| Glu (E) | Asp, Gln | Asp, |
| Gly (G) | Ala | Ala |
| His (H) | Asn, Gln, Lys, Arg | Arg, |
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (Met) ((M)) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, norleucine | Leu |

In certain embodiments, the substitutions occur in the CDR regions of the antibody. Typically, the obtained variant will have a modification (e.g., improvement) on some biological property (e.g., increased affinity) relative to the parent antibody and/or will have some biological property of the parent antibody that is substantially retained. Exemplary substitutional variants are affinity matured antibodies. In some embodiments, the substitutions occur in the CDR3 region of the heavy and/or light chain of the antibody. In some embodiments, there may be 1, 2, or 3 substitutions in the CDR3 region.

In certain embodiments, the substitution occurs in an FR region of the antibody, e.g., an FR region of a heavy and/or light chain variable region of the antibody, e.g., an FR1, FR2, FR2, or F4 region. In some embodiments, the substitution occurs in the FR2 region. In some embodiments, there may be 1, 2, or 3 substitutions in the FR region.

In certain embodiments, the invention provides antibodies comprising the variable region sequences disclosed herein or having the CDRs disclosed herein, and a constant domain having a modified Fc region with enhanced affinity for FcγRIIb as compared to its affinity for other Fc receptors (i.e., activation receptors). Such agonistic anti-CD40 antibodies with enhanced FcγRIIb specificity are expected to exhibit excellent efficacy in cancer therapy and chronic infection (Li and Ravatch (2011) Science 333: 1030; White et al (2011) j. immunol. 187: 1754). It is intended, without being limited by theory, that such FcγRIIb-specific agonistic anti-CD40 antibodies may exhibit enhanced adjuvant effects by increasing the maturation of dendritic cells that promote proliferation and activation of cytotoxic CD8+ T cells, leading to enhanced anti-tumor responses. It is intended, without being limited by theory, that the FcR-mediated signal enhancement of agonist CD40 antibodies due to cross-linking of the present invention may be a major contributor to therapeutic efficacy. Cross-linking of the FcR conjugated CD40 agonist antibody via the Fc part of the antibody may increase signal strength and thereby enhance cell activation.

Mutations in Fc sequences that can result in enhanced affinity for FcγRIIb are known in the art, and are described, for example, in Yu et al (2013) J. Am. chem. soc. 135:9723 and WO 2014/184545, Chu et al (2008) *Mol. Immunol.* 45:3926, and Mimoto et al (2013) *Protein Engineering Design & Selection* 26: 589. Nomenclature for the position (numbering) of mutations in the Fc region is according to the EU index, as in Kabat et al. (1981) *Sequences of Proteins of Immunological Interest*, 5th Edition Public Health Service, National Institutes of Health, Bethesda, Md.), which facilitates comparison of Fc Sequences at equivalent positions in antibodies having different variable domain lengths.

Exemplary mutations in the Fc sequence include, for example, E233D, G237D, H268D, P271G, A330R, S267E, and/or L328F. In a preferred embodiment, the antibodies of the invention comprise mutated human IgG1 constant domains with enhanced FcγRIIb specificity, said mutations including E233D, G237D, H268D, P271G and A330R, or S267E and L328F. See, e.g., SEQ ID NO:18 or 19 for sequences of exemplary antibody heavy chains comprising a mutated human IgG1 constant domain with enhanced FcγRIIb specificity.

In certain embodiments, the antibodies provided herein can be further modified to contain other non-protein moieties known and readily available in the art. Moieties suitable for antibody-deriving include, but are not limited to, water-soluble polymers. Non-limiting examples of water-soluble polymers include, but are not limited to, polyethylene glycol (PEG), ethylene glycol/propylene glycol copolymers, carboxymethylcellulose, dextran, polyvinyl alcohol, polyvinylpyrrolidone, poly-1,3-dioxane, poly-1,3,6-trioxane, ethylene/maleic anhydride copolymers, polyaminoacids (homopolymers or random copolymers), and dextran or poly (n-vinyl pyrrolidone) polyethylene glycol, propylene glycol homopolymers, polypropylene oxide/ethylene oxide copolymers, polyoxyethylated polyols (e.g., glycerol), polyvinyl alcohol, and mixtures thereof.

In certain embodiments, the antibodies provided herein are altered to increase or decrease the degree to which the antibody is glycosylated. Addition or deletion of glycosylation sites of an antibody can be conveniently achieved by altering the amino acid sequence so as to create or remove one or more glycosylation sites. When the antibody comprises an Fc region, the carbohydrate attached thereto may be altered. In some applications, modifications that remove unwanted glycosylation sites may be useful, for example, to remove the fucose moiety to improve antibody-dependent cellular cytotoxicity (ADCC) function (see Shield et al (2002) JBC277: 26733). In other applications, galactosylation modifications may be made to modify Complement Dependent Cytotoxicity (CDC).

In certain embodiments, it may be desirable to produce cysteine engineered antibodies, such as "thio MAbs," in which one or more residues of the antibody are replaced with a cysteine residue. Cysteine engineered antibodies can be produced as described, for example, in U.S. Pat. No. 7,521,541.

In some embodiments, the anti-CD40 antibodies or antigen-binding fragments thereof of the invention exhibit the same or similar binding affinity and/or specificity as the antibodies of the invention for CD40; and/or inhibit (e.g., competitively inhibit) the binding of an antibody of the invention to CD40 and/or bind to the same or overlapping epitope as an antibody of the invention; and/or competes with the antibodies of the invention for binding to CD40; and/or have one or more biological properties of an antibody of the invention.

In some embodiments, the anti-CD40 antibodies of the invention are an antibody in the form of IgG1 or an antibody in the form of IgG2 or an antibody in the form of IgG3 or an antibody in the form of IgG 4.

In some embodiments, the anti-CD40 antibody is a monoclonal antibody.

In some embodiments, the anti-CD40 antibody is humanized. Different methods for humanizing antibodies are known to a person skilled in the art, as reviewed by Almagro & Fransson, the contents of which are incorporated herein in their entirety by reference (Almagro J C and Fransson J (2008) Frontiers in Bioscience 13: 1619-1633).

In some embodiments, the anti-CD40 antibody is a human antibody. Human antibodies can be made using a variety of techniques known in the art. Human antibodies are generally described in van Dijk and van de Winkel, Curr. Opin. Pharmacol 5: 368-74(2001) and Lonberg, Curr. Opin. Immunol 20: 450-459(2008).

In some embodiments, the anti-CD40 antibody is a chimeric antibody.

In one embodiment, the anti-CD40 antibodies of the invention also encompass antibody fragments thereof, preferably antibody fragments selected from the group consisting of: Fab, Fab', Fab'-SH, Fv, single chain antibody (e.g. scFv) or (Fab')$_2$, single domain antibody, diabody (dAb), or linear antibody.

In certain embodiments, the anti-CD40 antibody molecule is in the form of a bispecific or multispecific antibody molecule. In one embodiment, the bispecific antibody molecule has a first binding specificity for CD40 and a second binding specificity for PD-1 or PD-L1 or PD-L2 or OX40 or 4-1BB or GITR, or the like. In one embodiment, the bispecific antibody molecule binds to CD40 and TNF or IL-17. Multispecific antibody molecules may have any combination of binding specificities for the foregoing molecules.

In some embodiments, the antibodies of the invention have one or more of the following properties:

(1) selectively binding to CD40 with a binding capacity higher than that to other TNFR family proteins, or not binding to other TNFR family proteins; in some embodiments, the binding is detected using ELISA.

(2) blocking the binding of CD40 to CD40 ligand (CD40L).

(3) activating cells expressing CD40, e.g. activating the NFkappa-B signaling pathway, in a cross-linked or constitutive form, preferably in a cross-linked form; in some embodiments, the detection is performed using flow cytometry; in some embodiments, the reporter cells used are cells expressing NF-κB-GFP and hCD40;

(4) binding to CD40, e.g., human CD40, with an equilibrium dissociation constant of less than or equal to about $5\times10^{-7}$ M, $4.5\times10^{-7}$ M, $4.4\times10^{-7}$ M, $4.3\times10^{-7}$ M, $4.2\times10^{-7}$ M, $4.1\times10^{-7}$ M, $4\times10^{-7}$ M, $3.9\times10^{-7}$ M, $3.8\times10^{-7}$ M, $3.7\times10^{-7}$ M, $3.6\times10^{-7}$ M, $3.5\times10^{-7}$ M, or $3.4\times10^{-7}$ M; in some embodiments, the measurement is a surface plasmon resonance technique.

(5) specifically binding to CD40 on cells expressing CD40 (e.g., human CD40 or Rhesus CD40); in some embodiments, the EC50 for binding to CD40 (e.g., human CD40 and/or Rhesus CD40) is less than or equal to about 50 nM, 40 nM, 30 nM, 20 nM, 15 nM, 14 nM, 13 nM, 12 nM, 10 nM, 9 nM, 8 nM. In some embodiments, the binding is detected using flow cytometry; in some embodiments, the cells expressing CD40 are 293 cells, e.g., 293FT cells.

(6) Inducing apoptosis of tumor cells. In some embodiments, EC50 is less than or equal to about 4 nM, 3.5 nM, 3 nM, 2.9 nM, 2.8 nM, 2.7 nM, or 2.6 nM; in some embodiments, the measurement is performed using flow cytometry. In some embodiments, the tumor cells are Raji cells or Ramos cells.

(7) having agonist activity, e.g., significant activation of (e.g., human) B cells or T cells or dendritic cells.

(8) promoting proliferation of (e.g. human) B cells or T cells.

(9) enhancing the immune response.

(10) inhibiting tumor growth, preferably while maintaining the individual's body weight.

In some embodiments, the CD40 antibody, when cross-linked, has one or more of the properties described above.

In some embodiments, the invention also encompasses antibodies conjugated to other substances ("immunoconjugates").

In some embodiments, the other substance is, for example, a therapeutic agent or label, such as a cytotoxic agent or an immunosuppressant or chemotherapeutic agent. Cytotoxic agents include any agent that is harmful to cells. Examples of cytotoxic agents (e.g., chemotherapeutic agents) or other substances suitable for forming immunoconjugates are known in the art, see, e.g., WO2017/004006 or WO2017/059243, among others.

In some embodiments, the label is, e.g., a tag sequence, e.g., a peptide. In a preferred embodiment, the tag amino acid sequence is a 6-His peptide, such as the tags provided in the pQE vector (QIAGEN, Inc., 9259 Eton Avenue, Chatsworth, CA, 91311) and the like, many of which are commercially available. As described in Gentz et al, 1989, Proc. Natl. Acad. Sci. USA 86:821-824, for example, 6-His provides for convenient purification of the fusion protein. Other peptide tags for purification include, but are not limited to, the hemagglutinin ("HA") tag, which corresponds to an epitope derived from the influenza hemagglutinin protein (Wilson et al, 1984, Cell 37:767) and the "flag" tag.

In other embodiments, the label may be a diagnostic agent or a detectable agent. The obtained antibody conjugates can be used as part of a clinical testing procedure (e.g., to determine the efficacy of a particular therapy) to monitor or predict the onset, formation, progression, and/or severity of a disease or disorder. Detectable or diagnostic agents include, but are not limited to, various enzymes such as horseradish peroxidase, alkaline phosphatase, beta-galactosidase, or acetylcholinesterase; prosthetic groups such as streptavidin/biotin and avidin/biotin; fluorescent substances such as, but not limited to, umbelliferone, fluorescein isothiocyanate, rhodamine, dichlorotriazinylamine fluorescein, dansyl chloride, or phycoerythrin; luminescent materials such as, but not limited to, luminol; bioluminescent materials such as, but not limited to, luciferase, luciferin, and aequorin; radioactive substances such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, and $^{67}$Ga), palladium ($^{103}$Pd), molybdenum ($^{99}$Mo), xenon ($^{133}$Xe) fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, 47Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; and positron emitting metal and nonradioactive paramagnetic metal ions for use in various positron emission tomography.

In some embodiments, the therapeutic agent comprises a chemotherapeutic agent, cytokine, cytotoxic agent, other antibody, small molecule drug, or an immunomodulatory agent.

In addition, the antibody molecules of the invention may be conjugated to a therapeutic moiety (therapeutic agent) such as a radioactive metal ion, such as an alpha-emitter such as $^{213}$Bi or a macrocyclic chelator that can be used to conjugate radioactive metal ions (including but not limited to $^{131}$In, $^{131}$LU, $^{131}$Y, $^{131}$Ho, $^{131}$Sm) to polypeptides. In certain embodiments, the macrocyclic chelator is 1,4,7,10-tetraazacyclododecane-N,N',N'',N'''-tetraacetic acid (DOTA), which can be attached to the antibody via a linker molecule. Such linker molecules are well known in the art and are described in Denardo et al, 1998, Clin Cancer Res. 4(10):2483-90, each of which is incorporated by reference in its entirety.

Techniques for conjugating therapeutic moieties to antibodies are well known, see, e.g., Arnon et al, "Monoclonal Antibodies For Immunotargeting Of Drugs In Cancer Therapy," cited from Monoclonal Antibodies And Cancer Therapy, Reisfeld et al (eds.), p. 243-256 (Alan R. Liss, Inc. 1985).

In some embodiments, the invention provides a nucleic acid encoding any of the antibodies or fragments thereof described herein or any chain thereof. In one embodiment, a vector comprising said nucleic acid is provided. In one embodiment, the vector is an expression vector, such as a pFuse vector. In one embodiment, a host cell comprising said nucleic acid or said vector is provided. In one embodiment, the host cell is eukaryotic. In another embodiment, the host cell is selected from a yeast cell, a mammalian cell (e.g., a CHO cell or 293 cell), or other cell suitable for the production of an antibody or antigen-binding fragment thereof. In another embodiment, the host cell is prokaryotic.

For example, the nucleic acid of the present invention comprises:

nucleic acid encoding an amino acid sequence selected from any one of SEQ ID NO:13-22, or an amino acid sequence having at least 85%, 90%, 91%, 92%, 93%, 94%, 95%, 96%, 97%, 98% or 99% identity with an amino acid sequence selected from any one of SEQ ID NO:13-22; or nucleic acid selected from the group consisting of the nucleic acids set forth in SEQ ID NOS:39-42, or a nucleic acid having at least 85%, 90%, 91%, 92%, 93%, 94%, 95%, 96%, 97%, 98%, or 99% identity with a nucleic acid selected from the group consisting of SEQ ID NOs:39-42.

The invention also encompasses nucleic acids that hybridize under stringent conditions to, or have one or more substitutions (e.g., conservative substitutions), deletions, or insertions on the following: a nucleic acid comprising a nucleic acid sequence encoding an amino acid sequence selected from the group consisting of those set forth in any one of SEQ ID NOs: 1-9; or a nucleic acid comprising a nucleic acid sequence encoding an amino acid sequence having at least 85%, 90%, 91%, 92%, 93%, 94%, 95%, 96%, 97%, 98% or 99% identity with an amino acid sequence selected from the group consisting of those set forth in any one of SEQ ID NOs:13-22; or a nucleic acid comprising a nucleic acid sequence selected from the group consisting of the nucleic acid sequences shown as SEQ ID NOs:39-42, or a nucleic acid comprising a nucleic acid sequence having at least 85%, 90%, 91%, 92%, 93%, 94%, 95%, 96%, 97%, 98%, or 99% identity with a nucleic acid sequence selected from the group consisting of the nucleic acid sequences shown as SEQ ID NOs:39-42.

In one embodiment, one or more vectors comprising the nucleic acid are provided. In one embodiment, the vector is an expression vector, such as a eukaryotic expression vector. Vectors include, but are not limited to, viruses, plasmids, cosmids, lambda phages, or Yeast Artificial Chromosomes (YACs). For example, the pFuse vector. Once an expression vector or DNA sequence has been prepared for expression, the expression vector can be transfected or introduced into a suitable host cell. Various techniques can be used to achieve this, for example, protoplast fusion, calcium phosphate precipitation, electroporation, retroviral transduction, viral transfection, biolistics, lipid-based transfection, or other conventional techniques. In the case of protoplast fusion, cells are grown in culture and screened for appropriate activity. Methods and conditions for culturing the resulting transfected cells and for recovering the resulting antibody molecules are known to those skilled in the art and may be varied or optimized depending on the particular expression vector and mammalian host cell used based on the present specification and methods known in the art. Alternatively, cells that have stably incorporated DNA into their chromosomes can be selected by introducing one or more markers that allow selection of transfected host cells. The marker may, for example, provide prototrophy to the auxotrophic host, biocidal resistance (e.g., antibiotics), or heavy metal (e.g., copper) resistance, etc. The selectable marker gene may be linked directly to the DNA sequence to be expressed or introduced into the same cell by co-transformation. Additional elements may also be required for optimal synthesis of mRNA. These elements may include splicing signals, as well as transcriptional promoters, enhancers, and termination signals.

In one embodiment, a host cell comprising one or more polynucleotides of the invention is provided. In some embodiments, host cells comprising the expression vectors of the invention are provided. In some embodiments, the host cell is selected from a yeast cell, a mammalian cell, or other cell suitable for the production of an antibody or antigen-binding fragment thereof.

In one embodiment, the invention provides a method of preparing an antibody molecule or fragment thereof (preferably an antigen-binding fragment) of the invention, wherein the method comprises culturing the host cell under conditions suitable for expression of a nucleic acid encoding the antibody molecule or fragment thereof (preferably an antigen-binding fragment) of the invention, and optionally isolating the antibody or fragment thereof (preferably an antigen-binding fragment). In a certain embodiment, the method further comprises recovering the antibody molecule of the invention or a fragment thereof (preferably an antigen-binding fragment) from the host cell.

In one embodiment, a method of preparing an antibody molecule of the invention is provided, wherein the method comprises culturing a host cell comprising a nucleic acid encoding the antibody (e.g., any one and/or more polypeptide chains) or an expression vector comprising the nucleic acid, as provided above, under conditions suitable for expression of the antibody, and optionally recovering the antibody from the host cell (or host cell culture medium).

For recombinantly producing of the antibody molecules of the invention, nucleic acids encoding the antibody (e.g., an antibody as described above, e.g., any one polypeptide chain and/or multiple polypeptide chains) are isolated and inserted into one or more vectors for further cloning and/or expression in a host cell. Such nucleic acids are readily isolated and sequenced using conventional procedures (e.g., by using oligonucleotide probes that are capable of binding specifically to genes encoding the heavy and light chains of an antibody).

Antibody molecules prepared as described herein can be purified by known prior art techniques such as high performance liquid chromatography, ion exchange chromatography, gel electrophoresis, affinity chromatography, size exclusion chromatography, and the like. The actual conditions used to purify a particular protein also depend on net charge, hydrophobicity, hydrophilicity, etc., and these will be apparent to those skilled in the art. The purity of the antibody molecules of the invention can be determined by any of a variety of well-known analytical methods, including size exclusion chromatography, gel electrophoresis, high performance liquid chromatography, and the like.

In some embodiments, the invention also provides methods of identifying, screening or characterizing the physical/chemical properties and/or biological activities of the antibody molecules of the invention.

In one aspect, antibodies of the invention are tested for antigen binding activity, e.g., by known methods such as ELISA, Western blot, and the like. Binding to CD40 can be determined using methods known in the art, exemplary methods being disclosed herein. In some embodiments, a surface plasmon resonance assay (e.g., affinity measurement) or ELISA assay is used.

The invention also provides assays for identifying anti-CD40 antibodies that are biologically active. Biological activities may include, for example, binding to CD40 (e.g., binding to human and/or Rhesus CD40), increasing CD40-mediated signal transduction (e.g., increasing NFkappa-B signaling pathway), depleting cells expressing CD40 (e.g., Raji or Ramos cells) by directly inducing tumor cell apoptosis, activating dendritic cells or B cells or T cells (e.g., by increasing cytokine production by T cells), promoting T cells (e.g., CD8+ T cells, e.g., activated CD8+ T cells), or B cell to proliferate or to inhibit tumor growth.

In certain embodiments, antibodies of the invention are tested for such biological activity.

Activation of T cells ((e.g., CD8+ T cells)) or dendritic cells or B cells can be determined using methods known in the art. For example, by the level (e.g., expression) of the cell activation markers CD8 (T cells) or CD86 (dendritic cells or B cells). T cell activation can also be measured using methods known in the art to measure CD40 signaling (e.g., NF-κB signaling pathway). In one embodiment, transgenic cells are generated that express human CD40 and a reporter gene comprising the NF-kappaB promoter fused to a reporter gene (e.g., β-luciferase, GFP). Addition of anti-CD40 antibody to the cells resulted in increased NF-kappaB transcription, which was detected using an assay for a reporter gene (e.g., luciferase reporter assay).

The ADCC effect of an antibody can be determined using methods known in the art. For example, by detecting its induction of apoptosis in the tumour cell (for example by an apoptosis marker molecule such as CD 95), inhibition of tumour cell growth or inhibition of tumour growth in vivo.

Proliferation of T cells (e.g., CD8+ T cells, such as activated CD8+ T cells) or B cells can be determined using methods known in the art. The proliferation of B cells is measured, for example, by luminescence, such as CellTiter-Glo luminescence. Proliferation of CD8+ T cells is also detected, for example, by OVA-specific OT-I cell method.

Cells for use in any of the above in vitro assays include cell lines that naturally express CD40 or that have been engineered to express CD40. Such cells include T cells that naturally express CD40L ((e.g., CD8+ T cells, e.g., activated CD8+ T cells)), B cells or dendritic cells that naturally express CD40. Such cells also include cell lines transfected with CD40-expressing and not normally expressing CD40-encoding CD40 DNA.

It will be appreciated that any of the above assays can be performed using the immunoconjugates of the invention in place of or in addition to an anti-CD40 antibody.

It will be appreciated that any of the above assays can be performed using anti-CD40 antibodies and other active agents.

In some embodiments, the invention provides pharmaceutical compositions and combinations comprising the antibodies of the invention.

In some embodiments, the invention provides a composition comprising any of the antibody molecules described herein or fragments thereof (preferably antigen-binding fragments thereof) or immunoconjugates thereof, preferably the composition is a pharmaceutical composition. In one embodiment, the composition further comprises a pharmaceutical excipient.

The invention also includes compositions (including pharmaceutical compositions or pharmaceutical formulations) comprising an antibody of the invention or an immunoconjugate thereof and/or compositions (including pharmaceutical compositions or pharmaceutical formulations) comprising a polynucleotide encoding an antibody of the invention. In certain embodiments, the composition comprises one or more antibodies or fragments thereof of the invention or one or more polynucleotides encoding one or more antibodies or fragments thereof of the invention.

These compositions may also contain suitable pharmaceutical excipients such as pharmaceutical carriers, pharmaceutical excipients, including buffers, as are known in the art.

As used herein, "pharmaceutically acceptable carrier" includes any and all solvents, dispersion media, isotonic and absorption delaying agents, and the like that are physiologically compatible. Pharmaceutical carriers suitable for use in the present invention can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. For the utilization of excipients and their use, see also "Handbook of Pharmaceutical Excipients", fifth edition, R. C. Rowe, P. J. Seskey and S. C. Owen, PharmaceuticalPress, London, Chicago.

The composition may also contain minor amounts of wetting or emulsifying agents, or pH buffering agents, if desired.

The compositions of the present invention may be in a variety of forms. Such forms include, for example, liquid, semi-solid, and solid dosage forms, such as liquid solutions (e.g., injectable and infusible solutions), dispersions or suspensions, liposomal formulations, and suppositories. The preferred form depends on the intended mode of administration and therapeutic use. The generally preferred compositions are in the form of injectable or infusion solutions. Preferred modes of administration are parenteral (e.g., intravenous, subcutaneous, intraperitoneal (i.p.), intramuscular) injection. In a preferred embodiment, the antibody molecule is administered by intravenous infusion or injection. In another preferred embodiment, the antibody molecule is administered by intramuscular, intraperitoneal or subcutaneous injection.

Agonist antibodies of the invention that specifically bind to human CD40 can be lyophilized for storage and reconstituted in a suitable carrier prior to use. Such technique has been proven effective for conventional protein formulations and well known lyophilization and reconstitution techniques can be employed.

The pharmaceutical compositions or formulations of the invention may also contain other therapeutic agents that are required for the particular indication being treated, preferably those having complementary activities that do not adversely affect each other. For example, chemotherapeutic agents, cytotoxic agents, vaccines, other antibodies, anti-infective agents, small molecule drugs or immunomodulators and the like.

In some embodiments, the invention also provides a combination product comprising an antibody or antigen-binding fragment thereof of the invention, or an immunoconjugate thereof, and one or more additional therapeutic agents (e.g., chemotherapeutic agents, additional antibodies, cytotoxic agents, vaccines, anti-infective active agents, small molecule drugs, or immunomodulators, and the like).

In some embodiments, two or more of the ingredients of the combination product may be administered to a subject in combination, sequentially, separately or simultaneously.

In some embodiments, the invention also provides a kit comprising an antibody, pharmaceutical composition, immunoconjugate or combination product of the invention, and optionally a package insert directing administration.

In some embodiments, the invention also provides a pharmaceutical product comprising an antibody, pharmaceutical composition, immunoconjugate, combination product of the invention, optionally further comprising a package insert directing administration.

In some embodiments, the additional therapeutic agent includes, for example, one or more of: anti-CTLA-4 antibodies, anti-PD-1 antibodies, anti-PD-L1 antibodies, anti-TIGIT antibodies, anti-OX40 (also referred to as CD134, TNFRSF4, ACT35, and/or TXGP1L) antibodies, anti-LAG-3 antibodies, anti-CD73 antibodies, anti-CD137 antibodies, anti-CD27 antibodies, anti-CSF-1R antibodies, TLR agonists, or small molecule antagonists of IDO or TGFβ. Examples of therapeutic agents that can be combined with the antibodies of the invention are also found in WO2017/059243 or WO 2017/004006.

In some embodiments, the present invention also provides a method of enhancing an immune response (e.g., an antigen-specific T cell response) in a subject, comprising administering to the subject an effective amount of an anti-CD40 antibody, or antigen-binding fragment thereof, of the invention such that the immune response in the individual is enhanced. In some embodiments, the individual has a tumor.

In another embodiment, the subject has a viral infection, such as a chronic viral infection.

In some embodiments, the invention provides methods of activating T cells (e.g., CD8+ T cells) and/or dendritic cells and/or B cells in a subject using an antibody of the invention comprising administering to the subject an effective amount of an anti-CD40 antibody or antigen-binding fragment thereof of the invention. The invention also provides methods of promoting T cell (e.g., activated CD8+ T cell) or B cell proliferation using the methods of the invention, comprising administering to a subject an effective amount of an anti-CD40 antibody or antigen-binding fragment thereof of the invention. Thus, in some embodiments, in view of the ability of the anti-CD40 antibodies described herein to enhance co-stimulation of T cell responses, e.g., antigen-specific T cell responses, provided herein are in vitro and in vivo methods of stimulating, enhancing, or up-regulating antigen-specific T cell responses, e.g., anti-tumor T cell responses, using the antibodies described herein. CD4+ and CD8+ T cell responses can be enhanced using anti-CD40 antibodies. The T cells may be $T_{eff}$ cells, such as CD4+ $T_{eff}$ cells, CD8+ $T_{eff}$ cells, T helper ($T_h$) cells, and T toxic ($T_c$) cells.

In some embodiments, the invention provides methods of using the antibody molecules of the invention to treat or prevent a disease, such as a tumor or an infection, such as a chronic infection, in which modulation (e.g., enhancement) of an immune response in a subject is desired. Accordingly, the present invention also provides a method of inhibiting tumor growth in a subject, comprising administering to the subject an anti-CD40 antibody or antigen-binding fragment thereof of the invention, such that tumor growth is inhibited.

In some embodiments, the disease is a CD40-associated disease, e.g., the disease is a disease with reduced expression or activity of CD40 (e.g., as compared to a healthy control), or the disease is a disease with reduced levels of CD40 gene and/or protein (e.g., as compared to a healthy control); or the disease benefits from activation of CD40 activity, for example activation of the CD40 signalling pathway, and/or activation of T cells or B cells or dendritic cells. In some embodiments, the invention relates to a method of activating an antigenic activity or activating an antigen-mediated signaling pathway in an individual, the method comprising administering to a subject an effective amount of an antibody or antigen-binding fragment thereof disclosed herein. In some embodiments, activating CD40 activity or activating a CD40-mediated signaling pathway refers to activating a CD40 signaling pathway.

In some embodiments, the antibodies or antigen-binding fragments thereof of the invention are capable of eliciting antibody-dependent cell-mediated cytotoxicity (ADCC), thereby killing tumor cells. Accordingly, the present invention also relates to a method of treating a tumor comprising administering to an individual an effective amount of an antibody or antigen-binding fragment thereof of the present invention.

In another aspect, the invention relates to a method of preventing or treating a tumor (e.g. cancer) in a subject, said method comprising administering to said subject an effective amount of an antibody molecule or a pharmaceutical composition or an immunoconjugate or a combination product or kit as disclosed herein. In some embodiments, the tumor is a cancer. The tumor may be a solid tumor or a liquid tumor, such as a hematological malignancy. In certain embodiments, the tumor is an immunogenic tumor. In certain embodiments, the tumor is non-immunogenic. In certain embodiments, the tumor is positive for PD-L1. In certain embodiments, the tumor is PD-L1 negative.

In some embodiments, tumors treated and/or prevented with the antibody molecules include, but are not limited to, solid tumors, hematological cancers (e.g., leukemia, lymphoma, myeloma, e.g., multiple myeloma), and metastatic lesions. In one embodiment, the cancer is a solid tumor. Examples of solid tumors include malignancies, e.g., sarcomas and carcinomas of the various organ systems, such as those that affect the lung, breast, ovary, lymphoid, gastrointestinal (e.g., colon), anal, genital, and genitourinary tracts (e.g., kidney, urothelium, bladder cells, prostate), pharynx, CNS (e.g., brain, neural, or glial cells), head and neck, skin (e.g., melanoma), nasopharynx (e.g., differentiated or undifferentiated metastatic or locally recurrent nasopharyngeal carcinoma), and pancreas, and adenocarcinomas, including malignancies, such as colon, rectal, renal cell, liver, non-small cell lung, small intestine, and esophageal cancers. The cancer may be in an early, intermediate or advanced stage or metastatic cancer.

In some embodiments, the cancer is selected from colorectal cancer (e.g., CRC), melanoma, e.g., advanced stage melanoma (e.g., stage II-IV melanoma), or HLA-A2 positive-melanoma; pancreatic cancer, e.g., advanced pancreatic cancer; breast cancer, e.g., metastatic breast cancer or triple negative breast cancer; head and neck cancer (e.g., HNSCC); esophageal cancer; Renal Cell Carcinoma (RCC), e.g., renal clear cell carcinoma (ccRCC) or Metastatic Renal Cell Carcinoma (MRCC); lung cancer (e.g., NSCLC); cervical cancer; bladder cancer; or a hematological malignancy, e.g., leukemia (e.g., lymphocytic leukemia) or lymphoma (e.g., Hodgkin's Lymphoma (HL), non-hodgkin's lymphoma (NHL), diffuse large B-cell lymphoma (DLBCL), Mantle Cell Lymphoma (MCL), or CLL, e.g., relapsed or refractory chronic lymphocytic leukemia).

In some embodiments, examples of cancer further include, but are not limited to, B cell proliferative disorders, which further include, but are not limited to, lymphomas (e.g., B cell non-hodgkin's lymphoma (NHL)) and lymphocytic leukemias.

In some embodiments, the tumor is a tumor, e.g., a cancer, e.g., a tumor or cancer with T cell dysfunction, in which activation of T cells or B cells or dendritic cells is desired. In some embodiments, the tumor is a tumor in which expression or activity of OX40 is reduced. In some embodiments, the tumor is a tumor that benefits from activation of the OX40 signaling pathway, e.g., a cancer.

In some embodiments, the cancer described herein is lymphoma, colon cancer, colorectal cancer, rectal cancer, lung cancer (e.g., non-small cell lung cancer), liver cancer, gastric cancer, and metastatic cancers thereof.

In some embodiments, the antibodies or antigen-binding fragments thereof of the invention are not suitable for treating hematologic cancers that have expression of CD40, which may be exacerbated by treatment with a CD40 agonist. Certain cancers may be known to express CD40 and thus would experience such exacerbations, and therefore may be excluded from the category. In specific embodiments, specific tumor samples are tested for CD40 expression and excluded from therapy with the CD40 antibodies of the invention based on the test results.

The methods and compositions disclosed herein may be used to treat metastatic lesions associated with the aforementioned cancers.

Antibodies or antigen-binding fragments thereof of the present invention that specifically bind to human CD40 can also be administered prophylactically to reduce the risk of developing cancer, delay the onset of events in cancer progression, and/or reduce the risk of relapse after remission of the cancer. This may be particularly useful for patients whose tumors are difficult to locate but are known to have one due to other biological factors.

In another aspect, the invention relates to a method of preventing or treating an infectious disease in a subject, said method comprising administering to said subject an effective amount of an antibody molecule or a pharmaceutical composition or an immunoconjugate or a combination product or kit as disclosed herein. In one embodiment, the infectious disease is a chronic infection. In some embodiments, the infection is a viral infection.

In some embodiments, the infection is acute or chronic. In some embodiments, the chronic infection is a persistent infection, a latent infection, or a slow infection. In some embodiments, the chronic infection is caused by a pathogen selected from the group consisting of bacteria, viruses, fungi, and protozoa.

In some embodiments, some examples of viruses include HIV, hepatitis (hepatitis A, B, and C), herpes viruses (e.g., VZV, HSV-1, HAV-6, HSV-II, and CMV, EB viruses), adenovirus, influenza virus, flavivirus, echovirus, rhinovirus, coxsackievirus, coronavirus, respiratory syncytial virus, mumps virus, rotavirus, measles virus, rubella virus, parvovirus, vaccinia virus, HTLV virus, dengue virus, papilloma virus, molluscum virus, polio virus, rabies virus, JC virus, and arbo encephalitis virus; some examples of bacteria include chlamydia, *Rickettsia*, mycobacteria, staphylococci, streptococci, pneumococcus, meningococci and gonococci, *Klebsiella, Proteus, Serratia, Pseudomonas, Legionella,* diphtheria, *Salmonella, Bacillus,* cholera, tetanus, botulism, anthrax, plague, leptospirosis, and lyme disease germs; some examples of fungi include Candida (*Candida albicans, Candida krusei, Candida glabrata, Candida tropicalis,* etc.), Cryptococcus neoformans, *Aspergillus (Aspergillus fumigatus, Aspergillus niger,* etc.), mucorales (mucor, Absidia, Rhizopus), Sporothrix schenkii, Blastomyces dermatitiditis, Paracoccidioides brasiliensis, Coccidioides immitis and Histoplasma capsulatum; some examples of parasites include Entamoeba histolytica Balantidium coli, Naegleriafowleri, *Acanthamoeba* sp., Giardia lambia, *Cryptosporidium* sp., Pneumocystis carinii, Plasmod ium viva x, Ba besia microti, Try pa nosomabrucei, Trypanosoma cruzi, Leishmania donovani, Toxoplasma gondii, and Nippostrongylus brasiliensis.

In some embodiments, infectious diseases treated and/or prevented with antibody molecules include pathogens for which no effective vaccine currently exists or for which conventional vaccines are not as effective as a complete pathogen. These include, but are not limited to, HIV, hepatitis (A, B and C), influenza, herpes, Giardia, malaria, Leishmania, *Staphylococcus aureus, Pseudomonas aeruginosa*.

Diseases that can be treated with the presently disclosed methods and compositions are also described in WO2017/059243 or WO 2017/004006.

In some embodiments, the antibodies or pharmaceutical compositions or immunoconjugates or combination products or kits of the invention can also be administered in combination with one or more other therapies, such as therapeutic modalities and/or other therapeutic agents, for prophylaxis and/or treatment as described herein.

In some embodiments, the treatment modality includes surgery (e.g., tumor resection); radiation therapy (e.g., external particle beam therapy, which involves three-dimensional conformal radiation therapy in which the irradiation region is designed), localized irradiation (e.g., irradiation directed at a preselected target or organ), or focused irradiation), and the like. The focused irradiation may be selected from stereotactic radiosurgery, fractionated stereotactic radiosurgery, and intensity-modulated radiation therapy. The focused irradiation may have a radiation source selected from the group consisting of particle beams (protons), cobalt-60 (photons), and linear accelerators (X-rays). Radiation therapy can be administered by one of several methods or a combination of methods including, without limitation, external particle beam therapy, internal radiation therapy, implant irradiation, stereotactic radiosurgery, whole-body radiotherapy, and permanent or transient interstitial brachytherapy.

In some embodiments, the therapeutic agent is selected from a chemotherapeutic agent, a cytotoxic agent, a vaccine, another antibody, an anti-infective active agent, or an immunomodulatory agent (e.g., an activator of a co-stimulatory molecule or an inhibitor of an immune checkpoint molecule).

Exemplary other antibodies include, but are not limited to, immune checkpoint inhibitors (e.g., anti-CTLA-4, anti-TIM-3, anti-CEACAM); antibodies that stimulate immune cells (e.g., agonistic GITR antibodies or CD137 antibodies); anti-cancer antibodies (e.g., rituximab (Rituxan® or MabThera®), trastuzumab (Herceptin®), Toxicolizumab (Bexxar®), ibritumomab nit (Zevalin®) A. group of monoclonal antibodies (Campath®), Epagbizumab (Lymphocide®), Bevacizumab (Avastin®), erlotinib (Tarceva®), Cetuximab (Erbitux®) and the like. For example, other antibodies may be anti-PD-L1 antibody, anti-LAG-3 antibody, anti-PD-1 antibody or anti-CLA-4 antibody.

Exemplary vaccines include, but are not limited to, cancer vaccines. The vaccine may be a DNA-based vaccine, an RNA-based vaccine, or a viral-transduction-based vaccine. Cancer vaccines can be prophylactic or therapeutic, such as cancer cells, purified tumor antigens (including recombinant proteins, peptides, and carbohydrate molecules), cells, and cells transfected with genes encoding immunostimulatory cytokines (He et al (2004) J. Immunol. 173: 4919-28). Non-limiting examples of tumor vaccines that can be used include peptides of melanoma antigens, such as gp100, MAGE antigen, Trp-2, MART1, and/or tyrosinase, or tumor cells transfected to express the cytokine GM-CSF. In some embodiments, the cancer vaccine is a peptide cancer vaccine, which in some embodiments is a personalized peptide vaccine. In some embodiments, the peptide cancer vaccine is a multivalent long peptide, a multiple peptide, a mixture of peptides, a hybrid peptide, or a peptide-pulsed dendritic cell vaccine (see, e.g., Yamada et al, Cancer Sci, 104:14-21, 2013). In some embodiments of any of the methods of the invention, administration of the antibody or fragment thereof of the invention is combined with administration of a tumor antigen. The antigen may be, for example, a tumor antigen, a viral antigen, a bacterial antigen or an antigen from a pathogen. In some embodiments, the tumor antigen comprises a protein. In some embodiments, the tumor antigen comprises a nucleic acid. In some embodiments, the tumor antigen is a tumor cell.

Exemplary anti-infective actives include, but are not limited to, antiviral agents, antifungal agents, antiprotozoal agents, antibacterial agents, such as the nucleoside analogs zidovudine (AST), ganciclovir, foscarnet, or cidovir, and the like.

Immune modulators include immune checkpoint molecule inhibitors and co-stimulatory molecule activators.

In some embodiments, the inhibitor of an immune checkpoint molecule is an inhibitor of CTLA-4, TIM-3, VISTA, BTLA, TIGIT, LAIR1, CD160, 2B4, CEACAM (e.g., CEACAM-1 and/or CEACAM-5), and/or TGFR. Inhibition of the molecule may be performed at the DNA, RNA or protein level. In some embodiments, inhibitory nucleic acids (e.g., dsRNA, siRNA or shRNA) can be used to inhibit expression of an immune checkpoint molecule. In other embodiments, the inhibitor of an immune checkpoint molecule is a polypeptide that binds to the immune checkpoint molecule, e.g., a soluble ligand or an antibody or antibody fragment.

In some embodiments, the immunomodulatory agent is an activator or agonist of a co-stimulatory molecule. In one embodiment, the agonist of the co-stimulatory molecule is selected from an agonist (e.g., an agonistic antibody or antigen-binding fragment thereof, or a soluble fusion) of a molecule selected from OX40, CD2, CD27, CDS, ICAM-1, LFA-1 (CD11a/CD18), ICOS (CD278), 4-1BB (CD137), GITR, CD30, CD40, BAFFR, HVEM, CD7, LIGHT, NKG2C, SLAMF7, NKp80, CD160, B7-H3, or CD83 ligand.

In some embodiments, the antibodies or fragments thereof of the invention can be administered in combination with a therapy comprising adoptive transfer of T cells (e.g., cytotoxic T cells or CTLs) expressing a Chimeric Antigen Receptor (CAR).

In some embodiments, the antibodies or fragments thereof of the invention may be administered in combination with an anti-tumor agent or an oncolytic virus.

In all of the above methods, CD40 agonism may be combined with other forms of immunotherapy, such as cytokine therapy (e.g., interferon, GM-CSF, G-CSF, IL-2) or bispecific antibody therapy, which provides enhanced tumor antigen presentation. See, e.g., Holliger (1993) Proc. Natl. Acad. Sci. USA 90: 6444-; Poljak (1994) Structure 2: 1121-.

In some embodiments, the antibodies or fragments thereof of the present invention may be combined with conventional methods of enhancing host immune function including, but not limited to: (i) APC augmentation, such as (a) injection of DNA encoding allogeneic MHC alloantigens into the tumor, or (B) transfection of biopsied tumor cells with genes that increase the likelihood of recognition of the immune antigens (e.g., immunostimulatory cytokines, GM-CSF, costimulatory molecules B7.1, B7.2), (iii) adoptive cellular immunotherapy, or treatment with activated tumor-specific T cells. Adoptive cellular immunotherapy involves isolation of tumor-infiltrating host T lymphocytes, such as by stimulating expansion of the population in vitro by IL-2 or tumor or both; in addition, dysfunctional isolated T cells may also be activated by in vitro application of an antibody of the invention, and the so-activated T cells may then be re-administered to the host.

The various combination therapies described above may be further combined for treatment.

Further examples of combinations of the antibodies of the invention with other therapeutic modalities or agents can be found in WO2017/059243 or WO2017/004006, among others.

Such combination therapies encompass both combined administration (where two or more therapeutic agents are contained in the same formulation or separate formulations), and separate administration, in which case administration of the antibody of the invention can occur prior to, concurrently with, and/or after the administration of the other therapy, e.g., the treatment modality and/or therapeutic agent. Antibody molecules and/or other therapies, e.g., therapeutics or treatment modalities, can be administered during active disease or during periods of remission or less active disease. The antibody molecule may be administered prior to other therapy, concurrently with other therapy, after therapy, or during remission of the disease.

It will be appreciated that any treatment can be carried out using an immunoconjugate or composition or combination product or kit of the invention in replacement of or in addition to an antibody of the invention.

The mode of administration of the antibodies of the invention (and pharmaceutical compositions or immunoconjugates comprising the same, and any additional therapeutic agent) can be any suitable route, such as parenteral administration, e.g., intradermal, intramuscular, intraperitoneal, intravenous or subcutaneous, mucosal (oral, intranasal, intravaginal, rectal), or other means as will be appreciated by those skilled in the art. Agonistic antibodies that specifically bind CD40 may be administered intratumorally to lymph node drainage sites using known methods for local delivery into tumors. Agonistic antibodies of the present invention that specifically bind human CD40 may be administered to a patient by any suitable route, for example, parenterally by intravenous (i.v.) infusion or bolus injection, intramuscularly or subcutaneously or intraperitoneally.

Various dosing schedules are contemplated herein, including, but not limited to, a single administration or multiple administrations at multiple time points, bolus administration, and pulsed infusion.

For the prevention or treatment of disease, the appropriate dosage of an antibody of the invention (when used alone or in combination with one or more other therapeutic agents) will depend on the type of disease to be treated, the type of antibody, the severity and course of the disease, whether the antibody is administered for prophylactic or therapeutic purposes, previous therapy, the patient's clinical history and response to the antibody, and the discretion of the attending physician. The antibody is suitably administered to the patient as a single treatment or over a series of treatments. Typically, the clinician administers the composition until a dosage is reached that achieves the desired effect. The antibodies of the invention may thus be administered in a single dose, or in two or more doses (which may contain the same or different amounts of the molecule of interest) over a period of time, or by continuous infusion through an implanted device or catheter. Appropriate dosages can be determined by using appropriate dose response data. In certain embodiments, the antibody can be administered to the patient over an extended period of time. In certain embodiments, the antibody is administered weekly, biweekly, monthly, every two months, every three months, every four months, every five months, or every six months.

In certain embodiments, the anti-CD40 antibodies or antigen-binding fragments thereof provided herein can be used to detect the presence of CD40 in a biological sample. The term "detection" as used herein includes quantitative or qualitative detection, exemplary detection methods may involve immunohistochemistry, immunocytochemistry, flow cytometry (e.g., FACS), magnetic beads complexed with antibody molecules, ELISA assays, PCR-techniques (e.g., RT-PCR). In certain embodiments, the biological sample is blood, serum, or other liquid sample of biological origin. In certain embodiments, the biological sample comprises a cell or tissue. In some embodiments, the biological sample is from a lesion associated with a disease (e.g., tumor or infection) described herein In some embodiments, CD40 is human CD40 or cynomolgus monkey CD40. In some embodiments, the methods comprise contacting the biological sample with an anti-CD40 antibody or antigen-binding fragment thereof as described herein under conditions that allow binding of the anti-CD40 antibody to CD40, and detecting whether a complex is formed between the anti-CD40 antibody and CD40. The formation of the complex indicates the presence of CD40. The method may be an in vitro or in vivo method. In one embodiment, the anti-CD40 antibody is used to select a subject suitable for treatment with an anti-CD40 antibody, e.g., wherein CD40 is the biomarker used to select the subject.

In one embodiment, an antibody of the invention can be used to diagnose a disease described herein, e.g., to assess (e.g., monitor) the treatment or progression of, diagnosis of, and/or stage of a disease described herein in a subject. In certain embodiments, labeled anti-CD40 antibodies are provided. Labels include, but are not limited to, labels or moieties that are detected directly (e.g., fluorescent labels, chromophore labels, electron-dense labels, chemiluminescent labels, and radioactive labels), as well as moieties that are detected indirectly, such as enzymes or ligands, for example, by enzymatic reactions or molecular interactions. Exemplary labels include, but are not limited to, the radio-isotope $^{32}P$, $^{14}C$, $^{125}I$, $^{3}H$, $^{131}I$, fluorophores such as rare earth chelates and derivatives thereof, rhodamine and derivatives thereof, dansyl, umbelliferone, luceriferase, e.g., firefly luciferase and bacterial luciferase (U.S. Pat. No. 4,737,456), luciferin, 2, 3-dihydrophthalazinedione, horseradish peroxidase (HR), alkaline phosphatase, beta-galactosidase, glucoamylase, lytic enzymes, carbohydrate oxidases, e.g., glucose oxidase, galactose oxidase, and glucose-6-phosphate dehydrogenase, heterocyclic oxidases such as uricase and xanthine oxidase, and dye enzymes utilizing hydrogen peroxide precursors such as HR, lactoperoxidase, or microperoxidase, biotin/avidin, spin labels, phage markers, stable free radicals, and the like.

In some embodiments of any of the inventions provided herein, the sample is obtained prior to treatment with an anti-CD40 antibody. In some embodiments, the sample is obtained prior to treatment with a disease drug described herein. In some embodiments, the sample is formalin fixed, paraffin coated (FFPE). In some embodiments, the sample is a biopsy (e.g., core biopsy), a surgical specimen (e.g., a specimen from a surgical resection), or a fine needle aspirate.

In some embodiments, CD40 is detected prior to treatment, e.g., prior to initiation of treatment or prior to some treatment after a treatment interval.

In some embodiments, a detection kit comprising an antibody or antigen-binding fragment thereof of the invention is provided for diagnosing a disease described herein, such as a tumor or an infection.

In some embodiments, there is provided a method of treating a disease described herein, such as a tumor or infection, the method comprising: the subject (e.g., sample) (e.g., subject sample) is tested for the presence of CD40, thereby determining a CD40 value, the CD40 value is compared to a control value, and if the CD40 value is less than the control value, a therapeutically effective amount of an anti-CD40 antibody (e.g., an anti-CD40 antibody described herein), optionally in combination with one or more other therapies, would be administered to the subject, thereby treating a disease, e.g., a tumor or an infection, described herein.

The invention therefore also relates to the use of an antibody or antigen-binding fragment thereof of the invention for the above-described method, and to the use of an antibody or antigen-binding fragment thereof of the invention in the manufacture of a medicament or composition or combination product or kit for the above-described method, and/or the use of an antibody or antigen-binding fragment thereof of the invention in the manufacture of a kit for the diagnosis of a disease described herein.

Methods and uses applicable to the antibodies or antigen-binding fragments thereof of the invention are equally applicable to immunoconjugates, compositions, combinations or kits comprising the antibodies or antigen-binding fragments thereof of the invention.

The invention is further illustrated in the following figures. However, these drawings and the specific embodiments of the invention should not be considered as limiting the scope of the invention, and modifications readily apparent to those skilled in the art will be included within the spirit of the invention and the scope of protection of the appended claims.

DRAWINGS

Figure 10A:
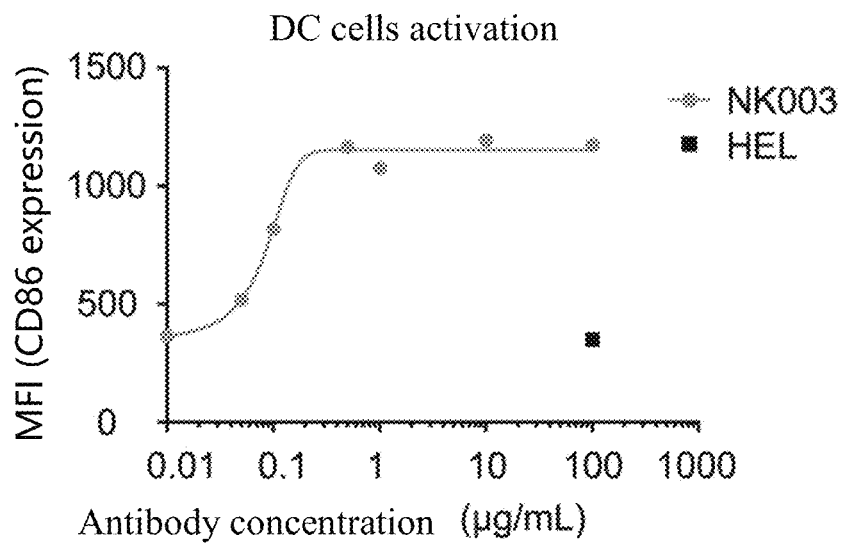
Figure 10B:
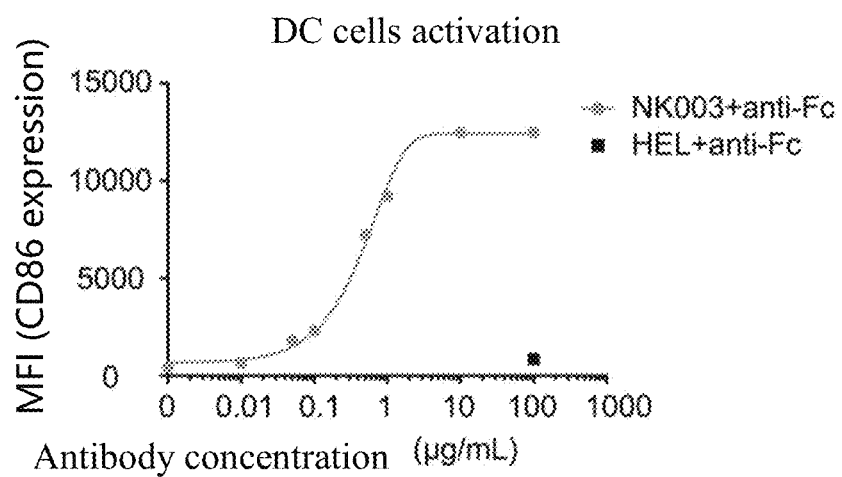

FIGS. 10A-10B show the activation of dendritic cells in PBMCs by the antibody NK003 of the present invention produced by 293F cells as determined by flow cytometry without addition of any cross-linking agent (FIG. 10A) and with addition of the cross-linking agent anti-Fc (FIG. 10B), respectively. The index for dendritic cell activation is the expression of CD86. MFI was defined as the product of the geometric mean of CD86-positive cells and the percentage of CD86-positive cells.

Figure 11:
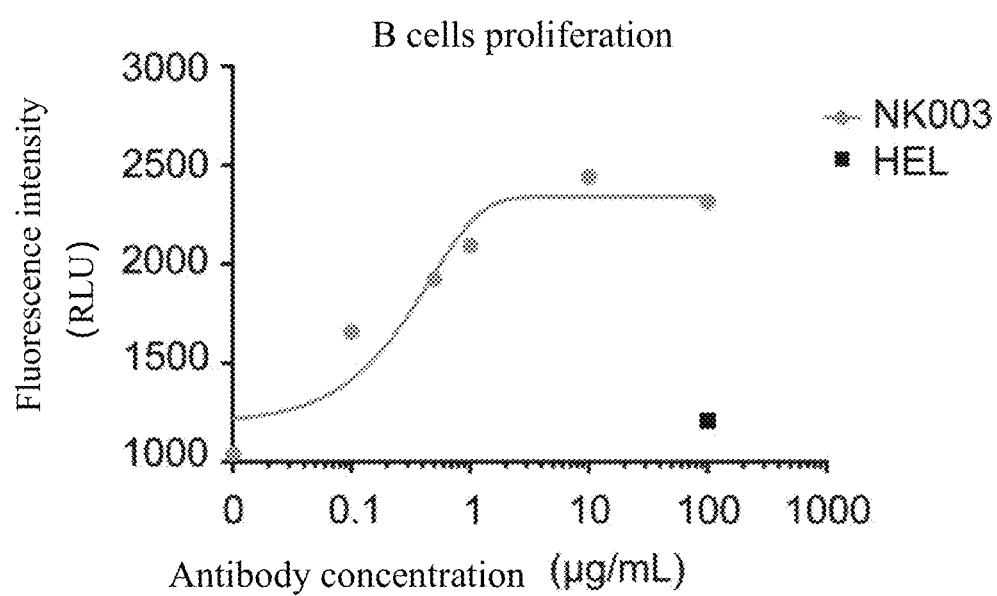

FIG. 11 shows the proliferation of B cells in PBMCs by the antibody NK003 of the present invention produced by 293F cells as measured using CellTiter-Glo method, and the index for cell proliferation is fluorescence intensity (RLU), with larger values of RLU indicating more cells.

Figure 12A:
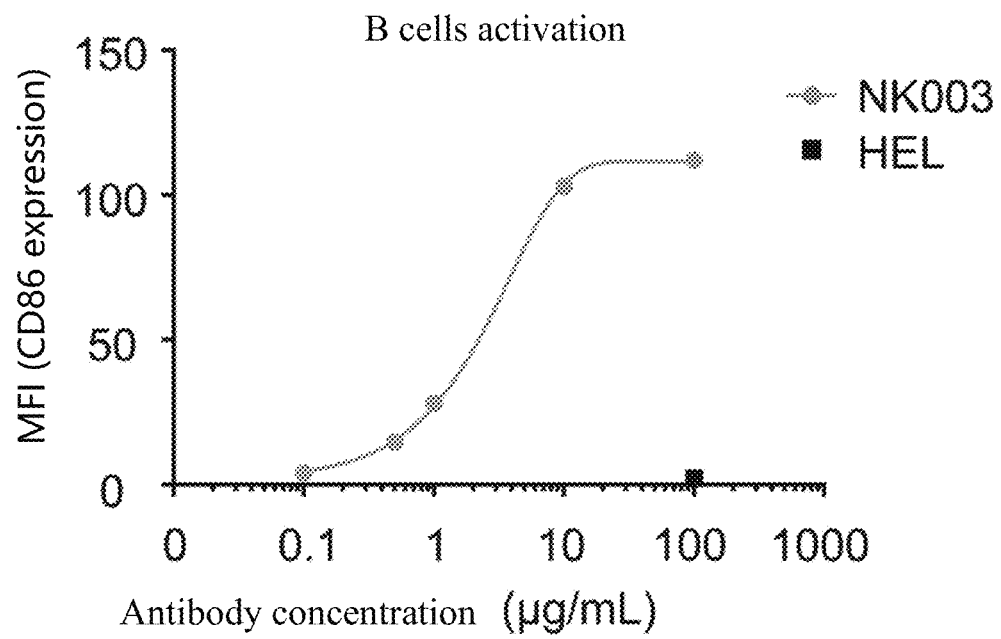
Figure 12B:
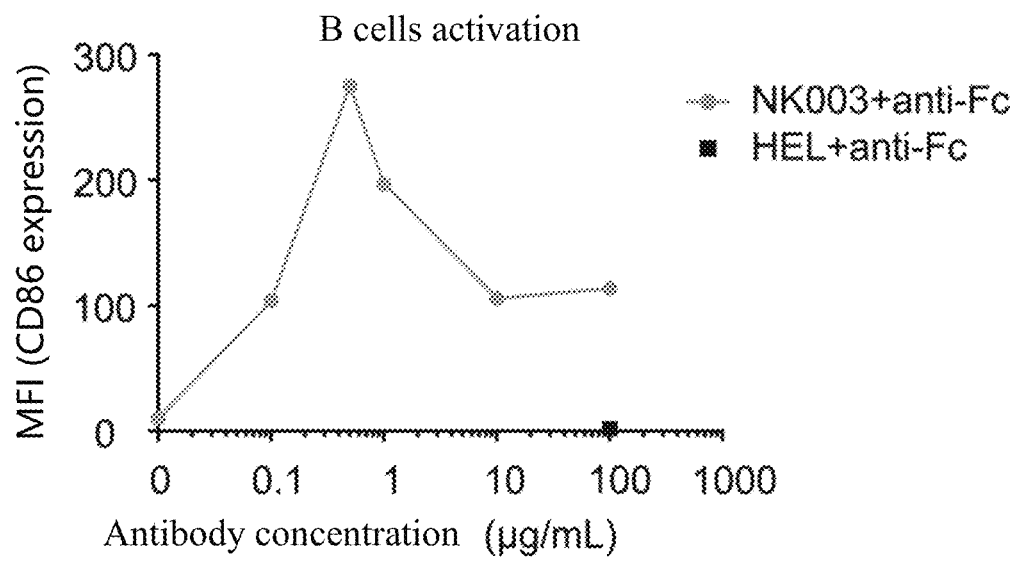

FIGS. 12A-12B show the activation of B cells in PBMCs by the antibody NK003 of the present invention produced by 293F cells as determined by flow cytometry without addition of any crosslinking agent (FIG. 12A) and with addition of the cross-linking agent anti-Fc (FIG. 12B), respectively. The index for B cell activation is the expression of CD86. MFI was defined as the product of the geometric mean of CD86-positive cells and the percentage of CD 86-positive cells.

Figure 13A:
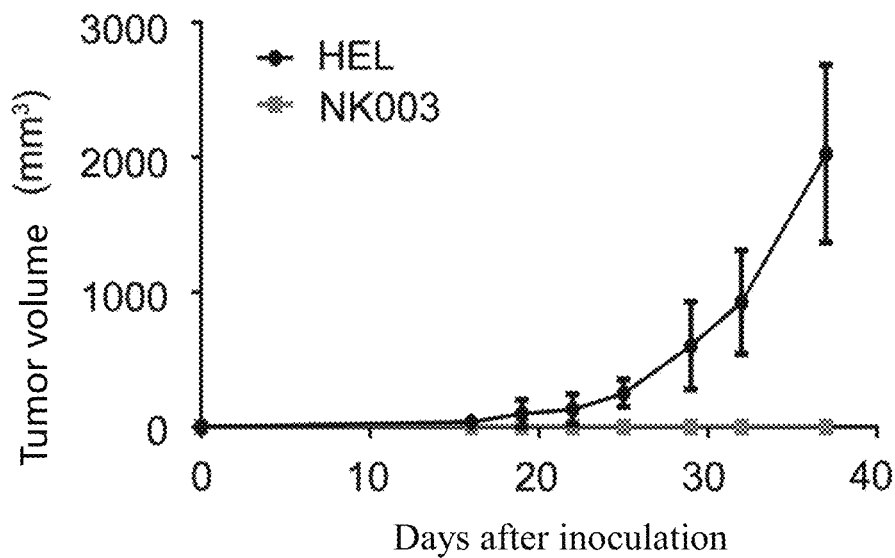
Figure 13B:
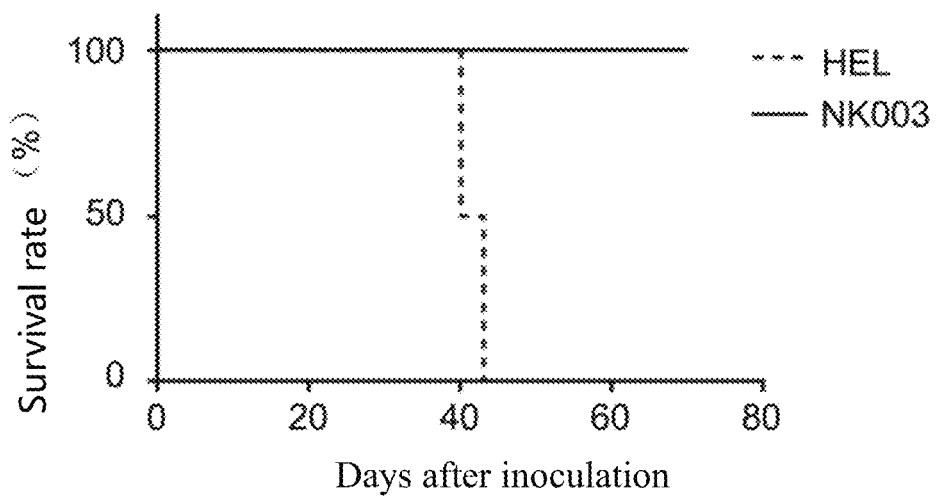

FIGS. 13A-13B show the individual mouse tumor growth curves (FIG. 13A) and statistics of the mouse survival rate (FIG. 13B) of the SCID mice in which the antibody NK003 of the invention and the negative control HEL produced in 293F cells were administered concurrently while Raji cells were inoculated.

Figure 14:
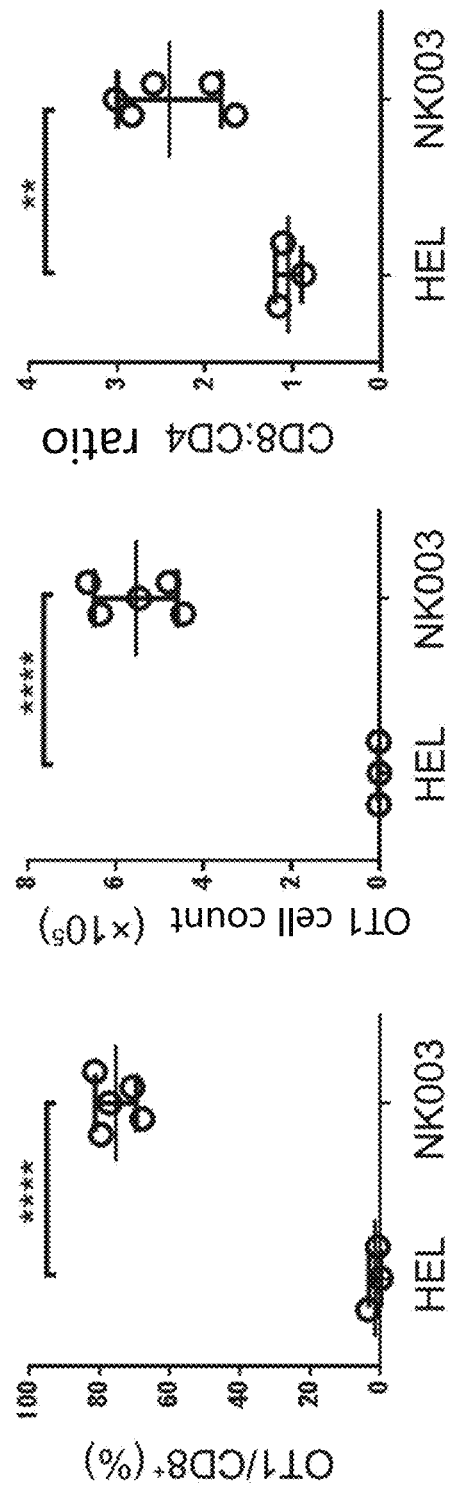

FIG. 14 shows that the activation of the immune system by the administration of the antibody NK003 of the present invention and the negative control HEL produced in 293F cells to MC38 tumor-bearing CD40-humanized mice and the increasing of the number of OT1 cells, the ratio of OT1 cells to CD8 cells (OT1/CD8$^+$ ratio) and the ratio of CD8 cells to CD4 cells (CD8/CD4 ratio) is indicative of the activation of the immune system.

Figure 15A:
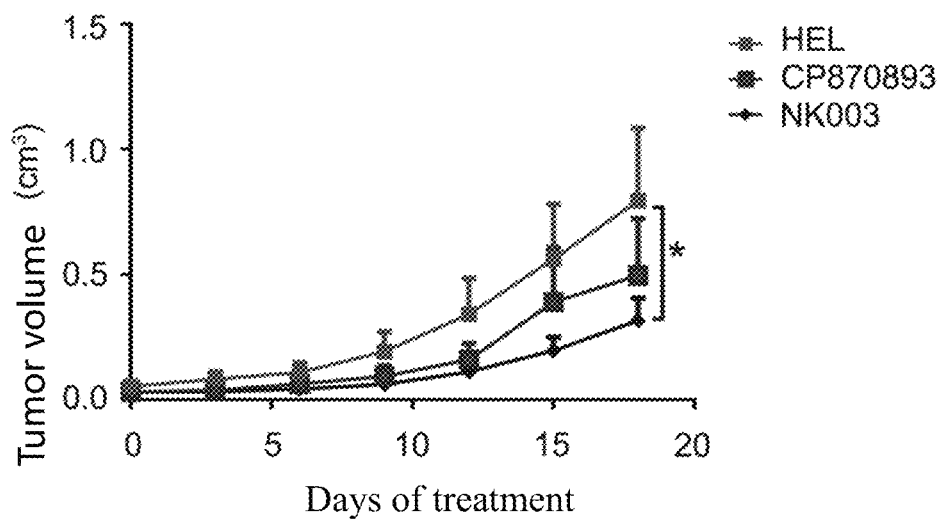
Figure 15B:
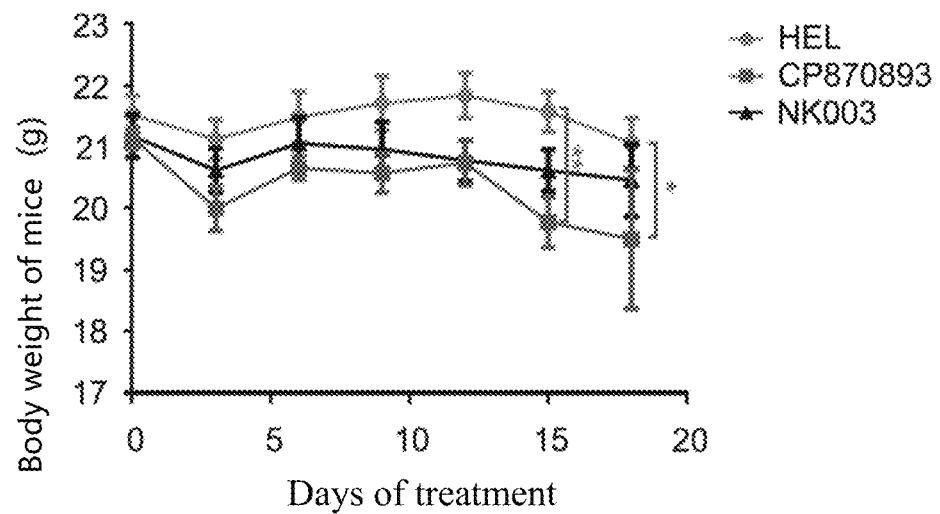

FIGS. 15A-15B show the individual mouse tumor growth curves (FIG. 15A) and mouse body weight curves (FIG. 15B) of the MC38 tumor-bearing CD40-humanized mice, to which the antibody NK003 of the present invention, the negative control HEL and the positive control CP870893 produced in 293F cells were administered.

Figure 16A:
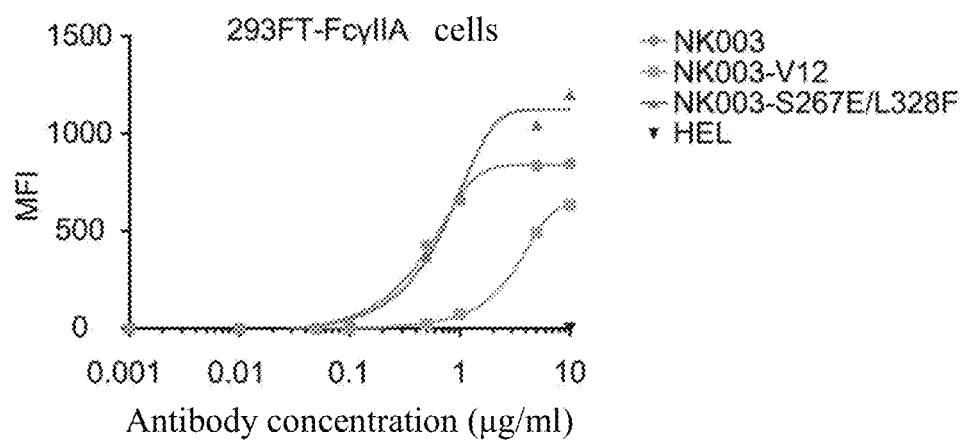
Figure 16B:
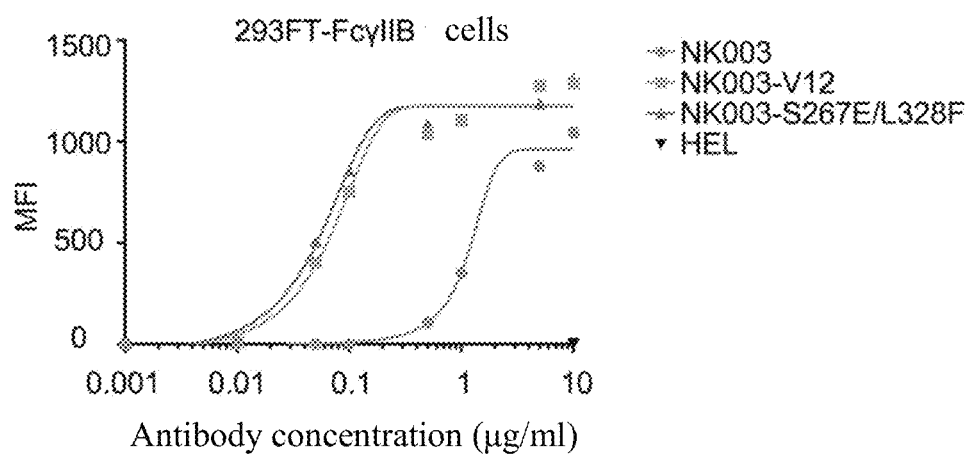

FIGS. 16A-16B show the activation of Jurkat/NF-κB-GFP+hCD40 reporter cells by the antibodies NK003 of the invention, FcγRIIB-enhanced variant NK003-V12, FcγRIIA/FcγRIIB-enhanced variant NK003-S267E/L328F and negative control HEL produced in 293F cells, cross-linked by 293 FT-FcγRIIA cells (FIG. 16A) and 293 FT-FcγRIIB cells (FIG. 16B), respectively, as determined by flow cytometry on 293F cells. GFP is detected in the FITC channel, and MFI is defined as the product of the geometric mean of GFP-positive cells and the percentage of GFP-positive cells.

Figure 17:
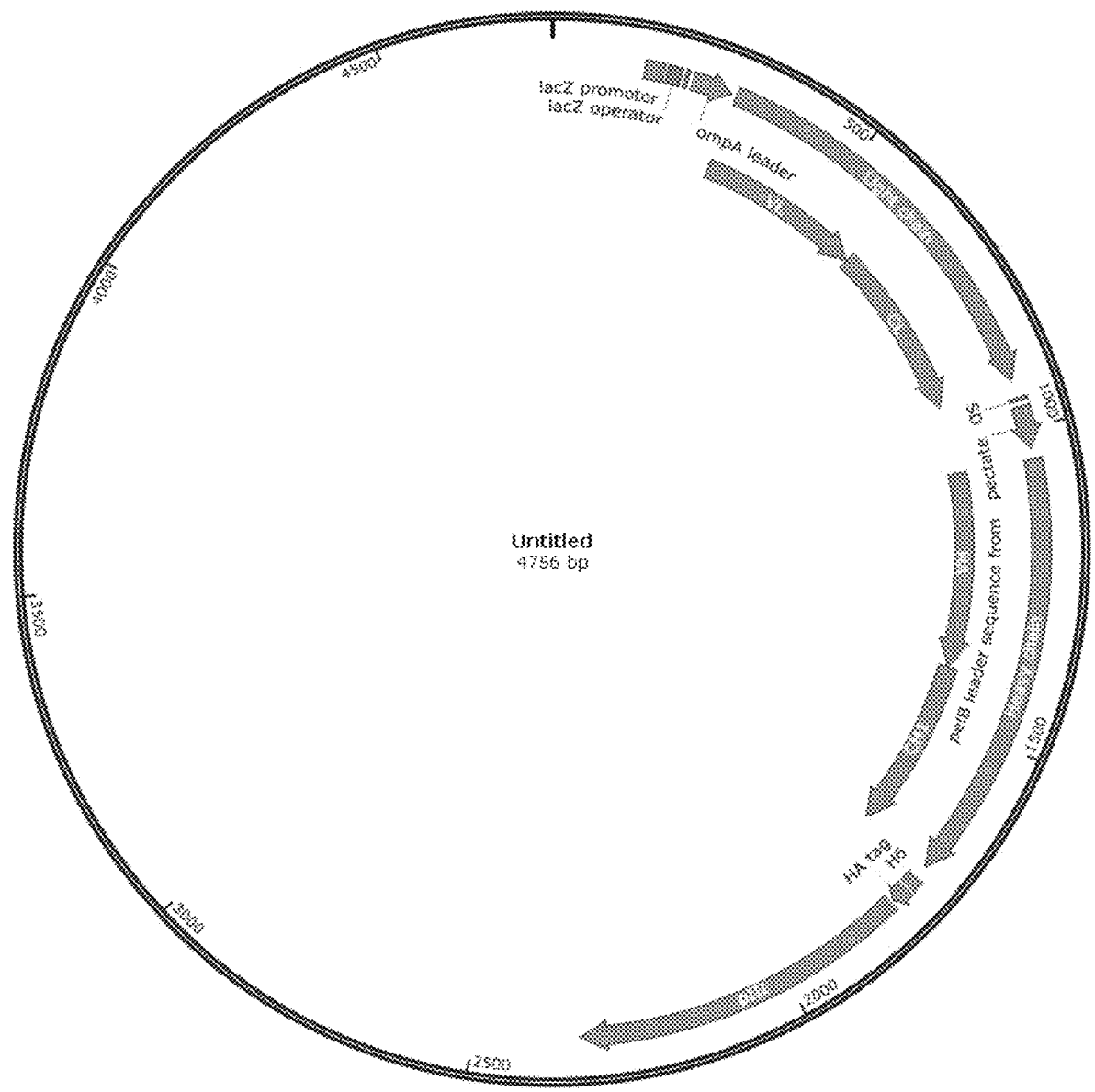

FIG. 17 shows a plasmid map of pcomb3 vector inserted by NK003 in Fab form.

Figure 18:
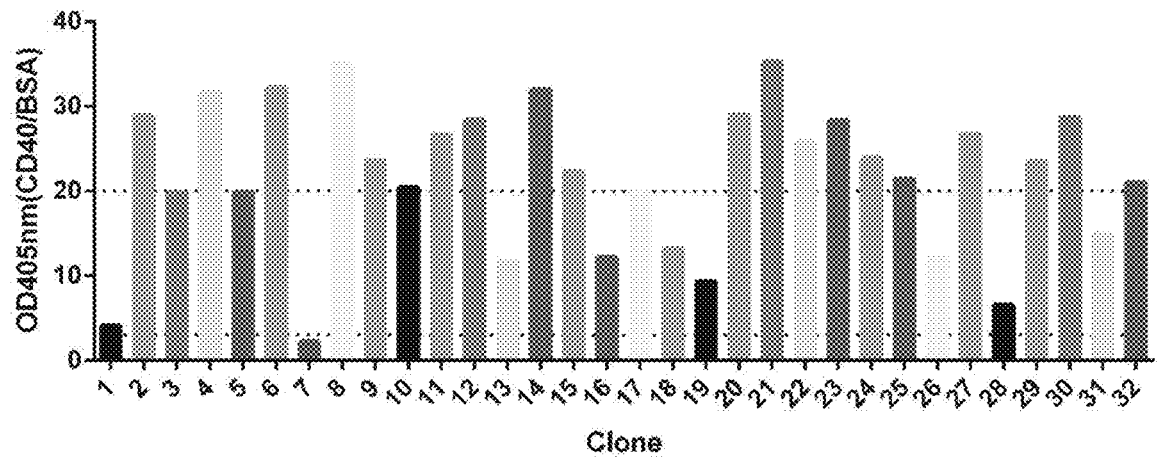

FIG. 18 shows the positive rate of CD40-binding antibody in the antibody library obtained from the third round of phage display as determined by phage ELISA, with antibodies with its binding to CD40 more than three times greater than the binding signal to BSA defined as positive antibodies.

Figure 19A:
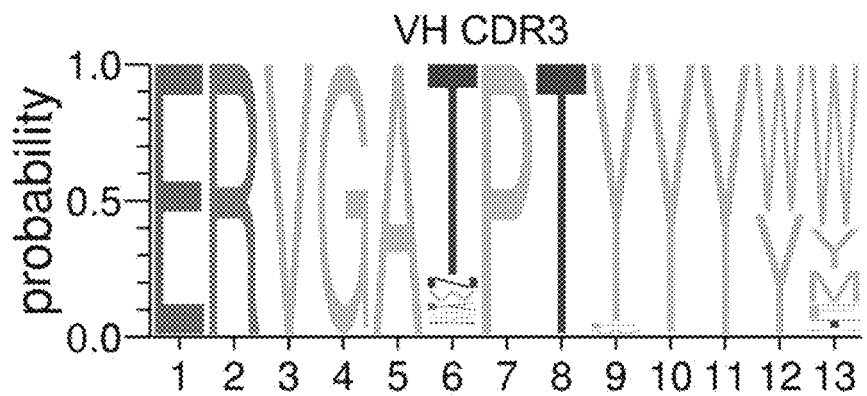
Figure 19B:
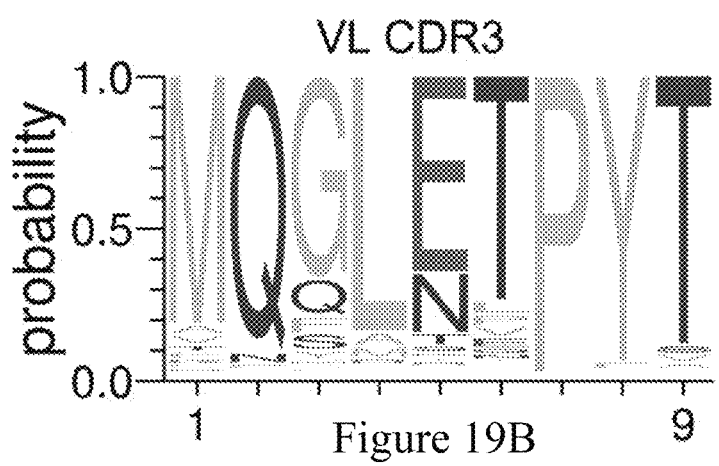

FIGS. 19A-19B show the third generation sequencing results of affinity maturation for complementarity determining region CDR3 of NK003 VH (FIG. 19A), VL (FIG. 19B).

Figure 20:
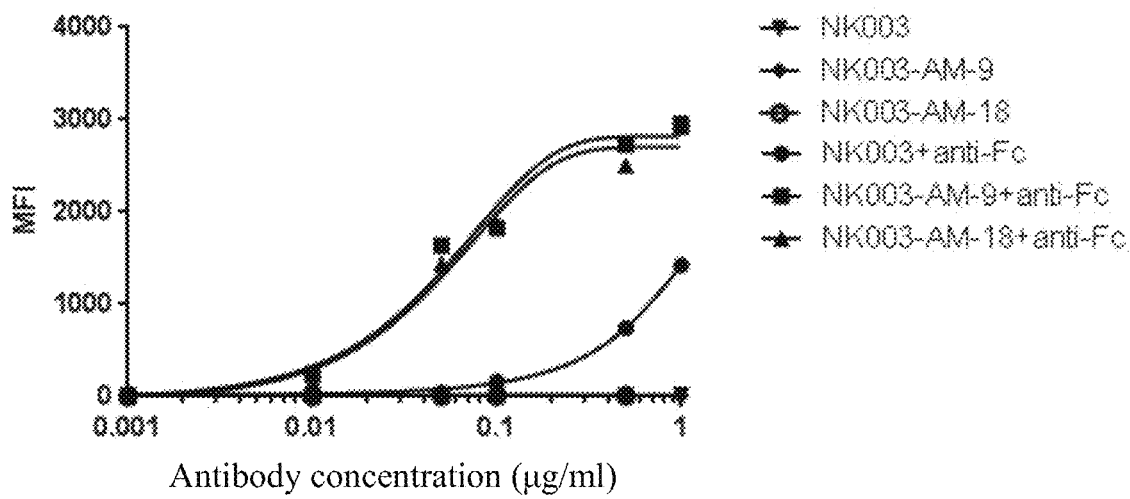

FIG. 20 shows the activation of Jurkat/NF-κB-GFP+ hCD40 reporter cells by the antibodies NK003-AM-9, NK003-AM-18 of the invention produced in 293F cells in a cross-linked form as determined by flow cytometry. GFP is detected in the FITC channel, and MFI is defined as the product of the geometric mean of GFP-positive cells and the percentage of GFP-positive cells.

Figure 21A:
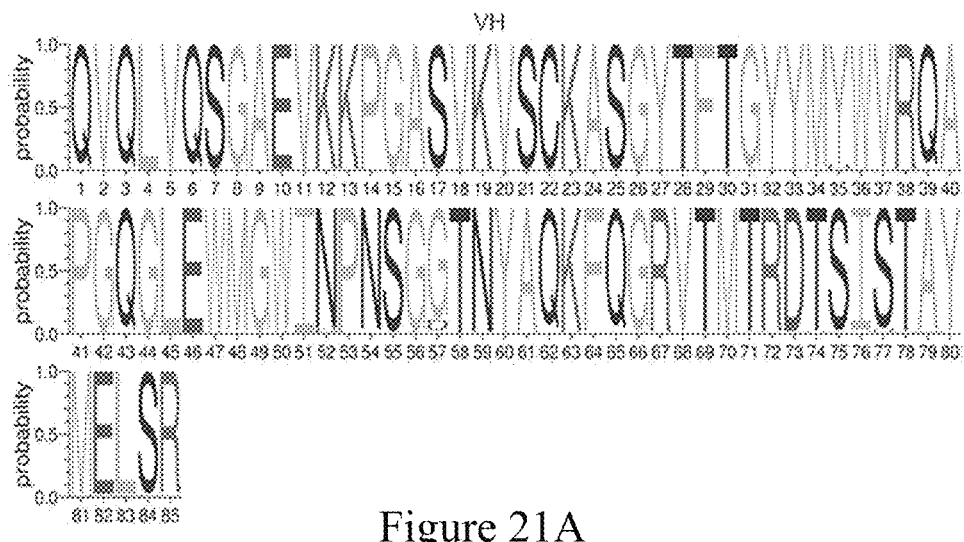
Figure 21B:
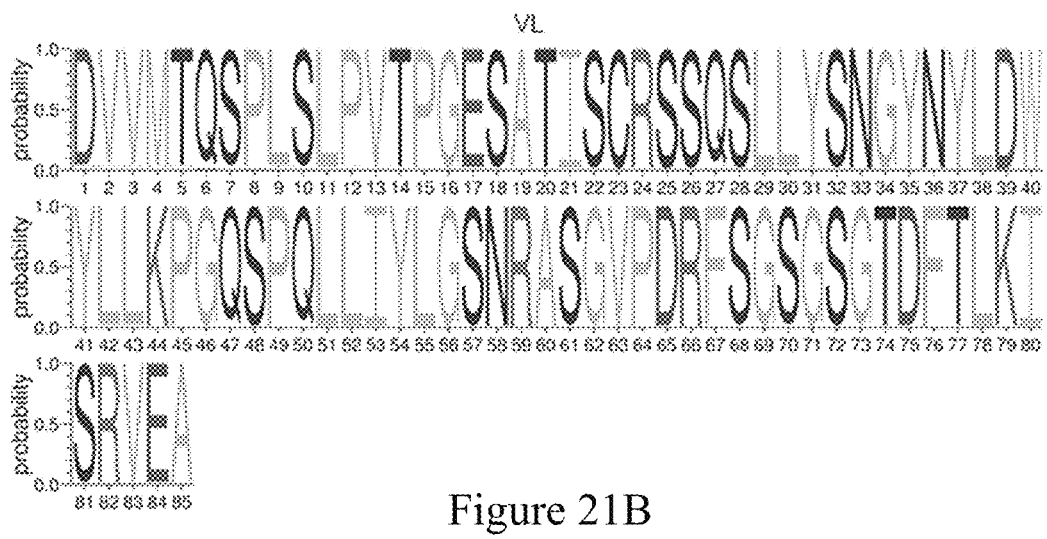

FIGS. 21A-21B show the third generation sequencing results of affinity maturation for framework regions of NK003 VH (FIG. 21A), VL (FIG. 21B).

Figure 22:
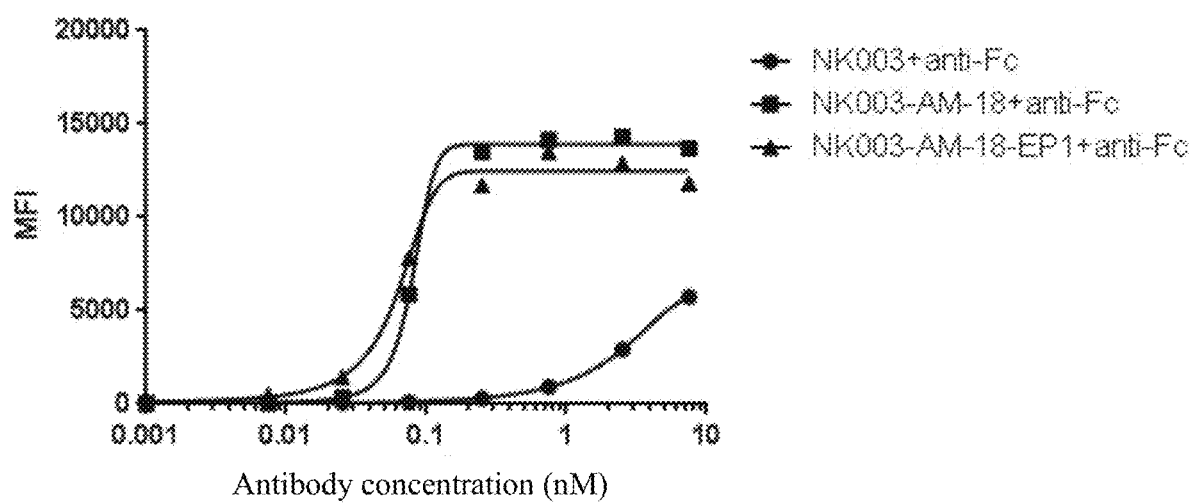

FIG. 22 shows that the antibody NK003-AM-18-EP1 of the invention produced in 293F cells activated the Jurkat/NF-κB-GFP+hCD40 reporter cells in a cross-linked form as determined by flow cytometry, with GFP being detected by FITC channel, and MFI being defined as the product of the geometric mean of GFP-positive cells and the percentage of GFP-positive cells.

DEFINITION

It should be understood that the terminology used herein is only intended to describe specific embodiments rather than limit the scope of the present invention, which will be limited only by the appended claims. Unless otherwise defined, any technical and scientific term used herein has the same meaning as commonly understood by those of ordinary skill in the art to which the present invention belongs.

For the purpose of explaining this specification, the following definitions will be used, and wherever appropriate, terms used in the singular form may also include the plural form, and vice versa. It should be understood that the terminology used herein is for the purpose of describing specific embodiments only and is not intended to be limiting.

The term "about" used in combination with a numerical value is intended to encompass the numerical values in a range from a lower limit less than the specified numerical value by 5% to an upper limit greater than the specified numerical value by 5%.

As used herein, the term "and/or" refers to any one of the options or any two or more of the options.

As used herein, the term "comprise" or "include" is intended to mean that the described elements, integers or steps are included, but none of any other elements, integers or steps are excluded. The term "comprise" or "include" used herein, unless otherwise specified, also encompasses the situation where the entirety consists of the described elements, integers or steps. For example, when referring to "comprise" an antibody variable region of a particular sequence, it is also intended to encompass an antibody variable region consisting of the specific sequence.

As used herein, the term "CD40" is known in the art, e.g., human CD40 or Rhesus CD40. CD40 is also known as tumor necrosis factor receptor superfamily member 5 (TNFRSF5), CD40L receptor, or CD154 receptor. The human full-length CD40 protein is a type I membrane protein with 277 amino acids, see e.g. NCBI, NM_001250.5. Rhesus monkey (*Macaca mulatta*) CD40 is see e.g. NCBI, NM_001265862.1.

The terms "anti-CD40 antibody", "anti-CD40", "CD40 antibody" or "antibody that binds CD40" or "antibody that specifically binds CD40" as used herein refer to an antibody that is capable of binding the (human or Rhesus) CD40 subunit or a fragment thereof with sufficient affinity such that the antibody can be used as a diagnostic and/or therapeutic agent in targeting (human or Rhesus) CD40. In one embodiment, the anti-CD40 antibody binds to a non-(human or Rhesus) CD40 protein to a lesser extent than about 10%, about 20%, about 30%, about 40%, about 50%, about 60%, about 70%, about 80%, or about 90% or more of the binding of the antibody to (human or Rhesus) CD40, as measured, for example, by radioimmunoassay (RIA), biological optical interferometry, or MSD assay.

Antibodies that specifically bind human CD40 may be cross-reactive to other related antigens, e.g., to the same antigen from other species (homologues), such as Rhesus monkey. Although monospecific antibodies specifically bind to one antigen or one epitope, and bispecific antibodies specifically bind to two different antigens or two different epitopes.

"Complementarity determining region" or "CDR region" or "CDR" is a region in an antibody variable domain that is highly variable in sequence and forms a structurally defined loop ("hypervariable loop") and/or comprises antigen-contacting residues ("antigen contact site"). CDRs are primarily responsible for binding to antigen epitopes. The CDRs of heavy and light chains are generally referred to as CDR1, CDR2, and CDR3, which are numbered sequentially from N-terminus. The CDRs located in a heavy chain variable domain of an antibody are referred to as HCDR1, HCDR2, and HCDR3, whereas the CDRs located in a light chain variable domain of an antibody are referred to as LCDR1, LCDR2, and LCDR3. In a given amino acid sequence of a light chain variable region or a heavy chain variable region, the exact amino acid sequence boundary of each CDR can be determined using any one or a combination of many well-known antibody CDR assignment systems including, e.g., Chothia based on the three-dimensional structure of antibodies and the topology of the CDR loops (Chothia et al. (1989) Nature 342:877-883; Al-Lazikani et al., Standard conformations for the canonical structures of immunoglobulins, Journal of Molecular Biology, 273:927-948 (1997)), Kabat based on antibody sequence variability (Kabat et al., Sequences of Proteins of Immunological Interest, 4th edition, U.S. Department of Health and Human Services, National Institutes of Health (1987)), AbM (University of Bath), Contact (University College London), International ImMunoGeneTics database (IMGT) (imgt.cines.fr/ on the World Wide Web), and North CDR definition based on the affinity propagation clustering using a large number of crystal structures.

For example, according to different CDR determination schemes, the residues of each CDR are as follows.

| CDR | Kabat scheme | AbM scheme | Chothia scheme | Contact scheme |
|---|---|---|---|---|
| LCDR1 | L24-L34 | L24-L34 | L26-L32 | L30-L36 |
| LCDR2 | L50-L56 | L50-L56 | L50-L52 | L46-L55 |
| LCDR3 | L89-L97 | L89-L97 | L91-L96 | L89-L96 |
| HCDR1 | H31-H35B | H26-H35B | H26-H32 | H30-H35B |
| (Kabat numbering system) | | | | |
| HCDR1 | H31-H35 | H26-H35 | H26-H32 | H30-H35 |
| (Chothia numbering system) | | | | |
| HCDR2 | H50-H65 | H50-H58 | H53-H55 | H47-H58 |
| HCDR3 | H95-H102 | H95-H102 | H96-H101 | H93-H101 |
| (Kabat numbering system) | | | | |

CDRs can also be determined based on having the same Kabat numbering positions as a reference CDR sequence (e.g., any of the exemplary CDRs of the present invention).

Unless otherwise stated, the term "CDR" or "CDR sequence" used herein encompasses CDR sequences determined by any of the schemes above.

Unless otherwise stated, in the invention, when referring to the residue positions in an antibody variable region (including heavy chain variable region residues and light chain variable region residues), it refers to the numbering positions according to the Kabat numbering system (Kabat et al., Sequences of Proteins of Immunological Interest, 5th Ed. Public Health Service, National Institutes of Health, Bethesda, Md. (1991)).

In one embodiment, the CDRs boundaries of the antibodies are determined by IMGT rules, for example using an IMGT database.

It should be noted that boundaries of CDRs in variable regions of an antibody determined by different assignment systems may differ. That is, CDR sequences of variable regions of an antibody defined by different assignment systems differ. Therefore, when it comes to defining an antibody with specific CDR sequences defined in the present invention, the scope of antibody also encompasses such antibodies whose variable region sequences comprise the specific CDR sequences, but having claimed CDR boundaries different from the specific CDR boundaries defined by the present invention due to a different protocol (e.g., different assignment system rules or their combinations) applied.

"Fc region" or "Fc domain" or "Fc" refers to the C-terminal region of the heavy chain of an antibody that mediates binding of an immunoglobulin to host tissues or factors, including binding to Fc receptors located on various cells of the immune system (e.g., effector cells) or to the first component of the classical complement system (C1q). Thus, the Fc region comprises the constant region of an antibody excluding the first constant region immunoglobulin domain (e.g., CH1 or CL). In IgG, IgA, and IgD isotypes, the Fc region comprises the CH2 and CH3 constant regions in each of the two heavy chains of an antibody; the IgM and IgE Fc regions comprise three heavy chain constant domains (CH domains 2-4) in each polypeptide chain. For IgG, the Fc region comprises the immunoglobulin domains Cγ2 and Cγ3 and the hinge between Cγ1 and Cγ2. Although the boundaries of the Fc region of an immunoglobulin heavy chain may vary, the human IgG heavy chain Fc region is generally defined as the fragment from the amino acid residue at position C226 or P230 (or the amino acid between these two amino acids) to the carboxy-terminus of the heavy chain, with numbering according to the EU index in Kabat. Kabat et al (1991) Sequences of proteins of Immunological Interest, National Institutes of Health, Bethesda, Md.; see also FIG. 3c-3f of U.S. patent application publication NO: 2008/0248028. The CH2 domain of the human IgG Fc region extends from about amino acid 231 to about amino acid 340, while the CH3 domain is located C-terminal to the CH2 domain in the Fc region, i.e., it extends from about amino acid 341 to about amino acid 447 (including the C-terminal lysine) of the IgG. As used herein, an Fc region can be a native sequence Fc, including any allotypic variant, or a variant Fc (e.g., a non-naturally occurring Fc). Fc may also refer to this region in isolation or in the context of Fc-containing protein polypeptides such as "binding proteins comprising an Fc region," also referred to as "Fc fusion proteins" (e.g., antibodies or immunoadhesins).

As used herein, the term "epitope" refers to the portion of an antigen (e.g., CD40) that specifically interacts with an antibody molecule. Epitopes within a protein antigen can be formed from contiguous amino acids (typically linear epitopes) or noncontiguous amino acids juxtaposed by tertiary folding of the protein (typically conformational epitopes). Epitopes formed from contiguous amino acids are typically, but not always, retained upon exposure to denaturing solvents, while epitopes formed from tertiary folding are typically lost upon treatment with denaturing solvents. Epitopes typically comprise at least 3, 4, 5, 6, 7, 8, 9, 10, 11, 12, 13, 14 or 15 amino acids in a unique spatial conformation.

"Antibody that binds to the same or overlapping epitope" as a reference antibody refers to an antibody that blocks more than 50%, 60%, 70%, 80%, 90%, or 95% of the binding of the reference antibody to its antigen in a competition assay, or conversely, the reference antibody blocking more than 50%, 60%, 70%, 80%, 90%, or 95% of the binding of the antibody to its antigen in a competition assay.

An antibody that competes with a reference antibody to bind to its antigen refers to an antibody that blocks more than 50%, 60%, 70%, 80%, 90%, or 95% of the binding of the reference antibody to its antigen in a competition assay. Conversely, the reference antibody blocks more than 50%, 60%, 70%, 80%, 90%, or 95% of the binding of the antibody to its antigen in a competition assay. Numerous types of competitive binding assays can be used to determine whether an antibody competes with another, such as direct or indirect solid-phase radioimmunoassay (RIA), direct or indirect solid-phase enzyme immunoassay (EIA), and sandwich competition assay (see, e.g., Stahli et al., 1983, *Methods in Enzymology* 9: 242-253).

An antibody that inhibits (e.g., competitively inhibits) the binding of a reference antibody to its antigen refers to an antibody that inhibits more than 50%, 60%, 70%, 80%, 90%, or 95% of the binding of the reference antibody to its antigen. Conversely, the reference antibody inhibits more than 50%, 60%, 70%, 80%, 90%, or 95% of the binding of the antibody to its antigen. The binding of an antibody to its antigen can be measured by affinity (e.g., equilibrium dissociation constant). Methods for determining affinity are known in the art.

An antibody that shows the same or similar binding affinity and/or specificity as a reference antibody refers to an antibody that is capable of having at least more than 50%, 60%, 70%, 80%, 90%, or 95% of the binding affinity and/or specificity of the reference antibody. This can be determined by any method known in the art for determining binding affinity and/or specificity.

An "IgG form of an antibody" refers to the IgG form to which the heavy chain constant region of an antibody belongs. The heavy chain constant regions are the same for all antibodies of the same type and differ between antibodies of different types. For example, an antibody in the form of IgG1 refers to an Ig domain whose heavy chain constant region Ig domain is IgG1.

"human" antibodies (humabs) refer to antibodies having variable regions in which both framework and CDR regions are derived from human germline immunoglobulin sequences. Furthermore, if the antibody contains constant regions, the constant regions are also derived from human germline immunoglobulin sequences.

"humanized" antibodies refer to antibodies in which some, most, or all of the amino acids outside the CDR domains of a non-human antibody (e.g., a mouse antibody) are replaced with corresponding amino acids derived from a human immunoglobulin. In one embodiment of a humanized form of an antibody, some, most, or all of the amino acids outside of the CDR domains have been replaced with amino acids from a human immunoglobulin, while some, most, or all of the amino acids within one or more CDR regions have not been altered. Small additions, deletions, insertions, substitutions or modifications of amino acids are permissible provided they do not abrogate the ability of the antibody to bind to a particular antigen. "humanized" antibodies retain an antigen specificity similar to the original antibody.

As used herein, "chimeric antibody" refers to an antibody in which the variable regions are derived from one species and the constant regions are derived from another species, such as an antibody in which the variable regions are derived from a mouse antibody and the constant regions are derived from a human antibody.

As used herein, "antibody fragment" refers to a molecule different from an intact antibody that comprises a portion of an intact antibody and binds to an antigen to which the intact antibody binds. As used herein, the term "antigen-binding fragment" as used herein refers to one or more fragments of an antibody that retain the ability to specifically bind to an antigen (e.g., human CD40). Examples of antibody fragments include, but are not limited to, Fv, Fab, Fab', Fab'-SH, F (ab')$_2$; diabody; a linear antibody; single chain antibodies (e.g., scFv); a single domain antibody; a bivalent or bispecific antibody or fragment thereof; camelid antibodies; and bispecific or multispecific antibodies formed from antibody fragments.

As used herein, "multispecific" refers to an antibody that specifically binds to at least two different antigens or two different epitopes within an antigen, e.g., three, four, or five different antigens or epitopes.

As used herein, "bispecific" refers to an antibody that specifically binds to two different antigens or two different epitopes within the same antigen. Bispecific antibodies may be cross-reactive to other related antigens or may bind an epitope shared between two or more different antigens.

As used herein, the term "cross-linking" refers to a higher degree of multimerization of CD40 on cells induced by the binding of an antibody that specifically binds human CD40 to cis or trans FcγRIIb, resulting in the induction of agonistic activity of CD40. Cross-linking can be assessed in vitro using anti-human F (ab') 2 as described herein as a cross-linking agent.

As used herein, the term "cross-reactivity" refers to the ability of an antibody described herein to bind CD40 from different species. For example, an antibody described herein that binds human CD40 also binds CD40 from another species (e.g., cynomolgus monkey CD40). As used herein, cross-reactivity can be measured by detecting specific reactivity or binding or otherwise functionally interacting with cells physiologically expressing CD40 with purified antigens in a binding assay (e.g., SPR, ELISA). Methods for determining cross-reactivity include standard binding assays as described herein, for example by BIACORE® Surface Plasmon Resonance (SPR) analysis using BIACORE 2000 SPR instruments (Biacore AB, Uppsala, Sweden) or flow cytometry techniques.

An "immunoconjugate" is an antibody conjugated to one or more other substances, including but not limited to cytotoxic agents or labels.

The term "label" used herein refers to a compound or composition which is directly or indirectly conjugated or fused to an agent, such as a polynucleotide probe or an antibody, and facilitates the detection of the agent to which it is conjugated or fused. The label itself can be detectable (e.g., a radioisotope label or a fluorescent label) or can catalyze a chemical change of a detectable substrate compound or composition in the case of enzymatic labeling. The term is intended to encompass direct labeling of a probe or an antibody by coupling (i.e., physical linking) a detectable substance to the probe the an antibody and indirect labeling of a probe or antibody by reacting with another reagent which is directly labeled. Examples of indirect labeling include detection of a primary antibody using a fluorescently labeled secondary antibody, and end labeling of a biotinylated DNA probe such that it can be detected with a fluorescently labeled streptavidin.

"Vector" refers to a polynucleotide that is capable of replication within a biological system or is movable between such systems. Vector polynucleotides typically contain elements such as origins of replication, polyadenylation signals, or selectable markers that function to facilitate replication or maintenance of these polynucleotides in a biological system. Examples of such biological systems may include cells, viruses, animals, plants, and biological systems reconstituted with biological components capable of replicating vectors. The polynucleotide comprising the vector may be a DNA or RNA molecule or a hybrid of such molecules. An "expression vector" refers to a vector that can be used in a biological system or a reconstituted biological system to direct the translation of a polypeptide encoded by a polynucleotide sequence present in the expression vector.

An "isolated" antibody is an antibody which has been separated from components of its natural environment. In some embodiments, the antibody is purified to a purity greater than 95% or 99% as determined by, e.g., electrophoresis (e.g., SDS-PAGE, isoelectric focusing (IEF) and capillary electrophoresis) or chromatography (e.g., ion exchange or reverse-phase HPLC). For a review of methods for assessing antibody purity, see, for example, Flatman et al., *J. Chromatogr.*, B848:79-87 (2007).

An "isolated" nucleic acid is a nucleic acid molecule that has been separated from components of its natural environment. An isolated nucleic acid includes a nucleic acid molecule contained in a cell that normally contains the nucleic acid molecule, but which is present extrachromosomally or at a chromosomal location different from its natural chromosomal location.

The calculation of sequence identity between sequences is performed as follows.

To determine the percent identity of two amino acid sequences or two nucleic acid sequences, the sequences are aligned for optimal comparison purposes (e.g., for optimal alignment, gaps can be introduced in one or both of the first and second amino acid sequences or nucleic acid sequences, or non-homologous sequences can be discarded for comparison). In one preferred embodiment, for comparison purposes, the length of the aligned reference sequence is at least 30%, preferably at least 40%, more preferably at least 50% or 60%, and even more preferably at least 70%, 80%, 90%, or 100% of the length of the reference sequence. Amino acid residues or nucleotides at corresponding amino acid positions or nucleotide positions are then compared. When a position in the first sequence is occupied by the same amino acid residue or nucleotide at the corresponding position in the second sequence, the molecules are identical at this position.

A mathematical algorithm can be used to compare the sequences and calculate percent identity between two sequences. In one preferred embodiment, the percent identity between two amino acid sequences is determined with the Needlema and Wunsch algorithm (((1970) J. Mol. Biol., 48:444-453; available at http://www.gcg.com) which has been integrated into the GAP program of the GCG software package, using the Blossom 62 matrix or PAM250 matrix and gap weights of 16, 14, 12, 10, 8, 6, or 4 and length weights of 1, 2, 3, 4, 5, or 6. In another preferred embodiment, the percent identity between two nucleotide acid sequences is determined with the GAP program (available at http://www.gcg.com) of the GCG software package, using the NWSgapdna.CMP matrix and gap weights of 40, 50, 60, 70, or 80 and length weights of 1, 2, 3, 4, 5, or 6. A particularly preferred parameter set (and one that should be used unless otherwise stated) is a Blossom 62 scoring matrix with a gap penalty of 12, a gap extension penalty of 4, and a frameshift gap penalty of 5.

The percent identity between two amino acid sequences or nucleotide sequences can also be determined with PAM120 weighted remainder table, gap length penalty of 12 and gap penalty of 4, using the E. Meyers and W. Miller algorithms which have been incorporated into the ALIGN program (version 2.0) ((1989) CABIOS, 4:11-17).

Additionally or alternatively, the nucleic acid sequences and protein sequences described herein can be further used as "query sequences" to perform searches against public databases to, e.g., identify other family member sequences or related sequences. As used herein, the term "hybridizes under low stringency, medium stringency, high stringency, or very high stringency conditions" describes hybridization and wash conditions. Guidance for performing hybridization reactions can be found in Current Protocols in Molecular Biology, John Wiley & Sons, N.Y. (1989), 6.3.1-6.3.6, which are incorporated by reference. Aqueous and non-aqueous methods are described in the reference and either method may be used. Specific hybridization conditions referred to herein are as follows: 1) low stringency hybridization conditions are those in 6× sodium chloride/citrate (SSC) at about 45° C. followed by two washes in 0.2×SSC, 0.1% SDS at least at 50° C. (the temperature of the wash can be increased to 55° C. for low stringency conditions); 2) moderate stringency hybridization conditions are one or more washes in 6×SSC at about 45° C. followed by 0.2× SSC, 0.1% SDS at 60° C.; 3) high stringency hybridization conditions are one or more washes in 6×SSC at about 45° C. followed by 0.2×SSC, 0.1% SDS at 65° C.; and preferably 4) very high stringency hybridization conditions are one or more washes in 0.5M sodium phosphate, 7% SDS at 65° C. followed by 0.2×SSC, 0.1% SDS at 65° C. The very high stringency condition (4) is the preferred condition and one should be used unless otherwise specified.

The terms "host cell," "host cell line," and "host cell culture" are used interchangeably and refer to a cell into which an exogenous nucleic acid is introduced, including the progeny of such a cell. Host cells include "transformants" and "transformed cells," which include primarily transformed cells and progeny derived therefrom, regardless of the number of passages. Progeny may not be identical in nucleic acid content to the parent cell but may contain mutations. Included herein are mutant progeny screened or selected for the same function or biological activity in the originally transformed cell. Suitable host cells for use in the present invention include prokaryotic microorganisms, such as *E. coli*. The host cell may also be a eukaryotic microorganism such as a filamentous fungus or yeast, or various eukaryotic cells such as insect cells and the like. Vertebrate cells can also be used as hosts. For example, mammalian cell lines engineered to be suitable for growth in suspension may be used. Examples of useful mammalian host cell lines include SV40 transformed monkey kidney CV1 line (COS-7); human embryonic kidney lines (HEK 293 or 293F cells), 293 cells, baby hamster kidney cells (BHK), monkey kidney cells (CV1), African green monkey kidney cells (VERO-76), human cervical cancer cells (HELA), canine kidney cells (MDCK), Bufarro rat liver cells (BRL 3A), human lung cells (W138), human liver cells (Hep G2), Chinese hamster ovary cells (CHO cells), CHOK1SV cells, CHOK1SV GS-KO cells, CHOS cells, NSO cells, myeloma cell lines such as Y0, NS0, P3X63, Sp2/0, and the like. A review of mammalian host cell lines suitable for protein production is found, for example, in Yazaki and Wu, Methods in Molecular Biology, Vol. 248 (published in B. K. C. Lo, Humana Press, Totowa, NJ), pp. 255-268 (2003). In a preferred embodiment, the host cell is a CHO cell, such as a CHOS cell CHOK1SV cell or CHOK1SV GS-KO, or the host cell is a 293 cell, such as a HEK293 cell.

The term "agonist" or "agonism" refers to an antibody that specifically binds to human CD40, which upon binding to CD40 induces proliferation or activation of B cells and/or Dendritic Cells (DCs) or T cells. Proliferation or activation of B cells and DC and T cells can be determined by: measuring increased B cell proliferation, or measuring upregulation of any of the surface markers CD23, CD80, CD83, CD86 on B cells, or CD80, CD83, CD86, and HLA-DR on DCs. Agonists are able to induce B-cell and/or DC and/or T-cell activation in a statistically significant manner when compared to control samples without antibody.

By "inhibiting tumor cell/tumor growth" is meant a measurable decrease in tumor cell growth or tumor in vitro or in vivo upon contact with a therapeutic agent or combination of therapeutic agents, as compared to the growth of the same tumor cell or tumor in the absence of the therapeutic agent. The inhibition of tumor cell or tumor growth in vitro or in vivo may be at least about 10%, 20%, 30%, 40%, 50%, 60%, 70%, 80%, 90%, 99% or 100%.

The term "therapeutic agent" as used herein encompasses any substance that is effective in preventing or treating a disease, such as a tumor (e.g., cancer) and an infection (e.g., chronic infection), including chemotherapeutic agents, cytotoxic agents, vaccines, other antibodies, anti-infective agents, small molecule drugs, or immunomodulators.

"Chemotherapeutic agents" include chemical compounds useful in the treatment of diseases of the immune system, including but not limited to alkylating agents; antimetabolites; anti-microtubule inhibitors, natural products; antibiotics; enzymes; miscellaneous agents; hormones and antagonists; Anti-estrogens; anti-androgens; non-steroidal anti-androgens, topoisomerase inhibitors, receptor tyrosine kinase inhibitors, angiogenesis inhibitors, etc. Exemplary chemotherapeutics of the present invention such as anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), Cisplatin (Platinol®), Claribine (Leustatin®), Cyclophosphamide (Cytoxan® or Neosar®), Cytarabine, Cytosine Arabinoside (Cytosar-U®), Cytosine arabinoside Liposome injection (DepoCyt®), dacarbazine (DTIC-Dome®), dactinomycin (actinomycin D, Cosmegan), daunorubicin hydrochloride (Cerubidine®), daunorubicin citrate Liposome injection (DaunoXome®), dexamethasone, docetaxel (Taxotere®), doxorubicin hydrochloride (Adriamycin®, Rubex®), etoposide (Vepesid®), fludarabine phosphate (Fludara)®), 5-Fluorouracil (Adrucil®, Efudex®), flutamide (Eulexin®), tezacitibine, gemcitabine (difluorodeoxycytidine), hydroxyurea (Hydrea®), idarubicin (Idamycin®), iso Cyclophosphamide (IFEX®), irinotecan (Camptosar®), L-asparaginase (ELSPAR®), leucovorin, melphalan (Alkeran®), 6-mercaptopurine (Purinethol®), methamine Pterin (Folex®), mitoxantrone (mitoxantrone), milota (mylotarg), paclitaxel (Taxol®), phoenix (yttrium 90/MX-DTPA), pentostatin, polystyrene 20Combined with carmustine implant (Gliadel®), tamoxifen citrate (Nolvadex®), teniposide (Vumon®), 6-thioguanine, cytepa, tirapazamine (Tirazone®), Topotecan Hydrochloride for Injection (Hycamptin®), Vinblastine (Velban®), Vincristine (Oncovin®), Vinorelbine (Vinorelbine), Ibrutinib, Gilead (idelalisib) and Brentuximab vedotin, and pharmaceutically acceptable salts, acids or derivatives of any of the above substances. This definition also includes anti-hormonal drugs such as anti-estrogen drugs used to modulate or inhibit the effect of hormones on tumors, including, for example, tamoxifen, raloxifene, aromatase inhibition 4 (5)-imidazole, 4-hydroxy Tamoxifen, trovoxifene, keoxifene, LY117018, onlastone and toremifene and antiandrogens such as flutamide, nilutamide, bicalutamide, leuprolide acetate and ge Serrelin; and a pharmaceutically acceptable salt, acid or derivative of any of the above.

The term "cytotoxic agent" as used herein refers to a substance that inhibits or prevents cell function and/or causes cell death or destruction. Exemplary cytotoxic agents include, but are not limited to: radioisotopes such as iodine ($^{131}$I, $^{125}$I, $^{123}$I, $^{121}$I), carbon ($^{14}$C), sulfur ($^{35}$S), tritium ($^3$H), indium ($^{115}$In, $^{113}$In, $^{112}$In and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; a growth inhibitor; alkylating agents (including but not limited to nitrogen mustards, ethylenimine derivatives, alkyl sulfonates, nitrosoureas, and triazenes), such as uracil mustards, nitrogen mustards (Chlormethine), cyclophosphamide (CYTOXA $^{117TM}$ 1), ifosfamide (fosfamide), melphalan, chlorambucil, guanhemogen, triethylenemelamine, triethylenethiophosphamide (triethylenethiophosphamide), busulfan, carmustine, lomustine, streptozotocin, dacarbazine, and temozolomide; or antimetabolites (including but not limited to folate antagonists, pyrimidine analogs, purine analogs, and adenosine deaminase inhibitors): methotrexate, 5-fluorouracil, floxuridine, cytarabine, 6-mercaptopurine, 6-thioguanine, fludarabine phosphate, pentostatin (pentastatin), and gemcitabine. In some embodiments, exemplary cytotoxic agents of the invention include antimicrotubule drugs, topoisomerase inhibitors, antimetabolites, mitotic inhibitors, alkylating agents, anthracyclines, vinca alkaloids, intercalating agents, agents capable of interfering with signal transduction pathways, pro-apoptotic agents, proteasome inhibitors, and irradiation (e.g., local or systemic irradiation (e.g., gamma radiation).

The term "small molecule drug" refers to a low molecular weight organic compound capable of regulating biological processes. "Small molecule" is defined as a molecule with a molecular weight of less than 10 kD, usually less than 2 kD and preferably less than 1 kD. The small molecule includes but is not limited to inorganic molecules, organic molecules, organic molecules containing inorganic components, molecules containing radioactive atoms, synthetic molecules, peptide mimetics, and antibody mimetics. As therapeutic agents, small molecules penetrate cells better, is less susceptible to degradation and is less likely to induce an immune response compared with large molecules. For descriptions of small molecules, such as peptide mimetics of antibodies and cytokines, and small molecule toxins, see, for example, Casset et al. (2003), *Biochem. Biophys. Res. Commun.*, 307:198-205; Muyldermans (2001), *J. Biotechnol.*, 74:277-302; Li (2000), *Nat. Biotechnol.*, 18:1251-1256; Apostolopoulos et al. (2002), *Curr. Med. Chem.*, 9:411-420; Monfardini et al. (2002), *Curr. Pharm. Des.*, 8:2185-2199; Domingues et al. (1999), *Nat. Struct. Biol.*, 6:652-656; Sato and Sone (2003), *Biochem. J.*, 371:603-608; U.S. Pat. No. 6,326,482.

The term "anti-infective active agent" includes any molecule that specifically inhibits or eliminates the growth of a microorganism, such as a virus, bacterium, fungus, or protozoan, e.g., a parasite, at the administered concentration and dosing interval, but is not lethal to the host. As used herein, the term anti-infective active agent includes antibiotics, antibacterial agents, antiviral agents, antifungal agents, and antiprotozoal agents. In a particular aspect, the anti-infective active agent is non-toxic to the host at the administration concentration and dosing interval.

Anti-infective active agents or antibacterial agents that are antibacterial may be broadly classified as bactericidal (i.e., direct killing) or bacteriostatic (i.e., arresting division). Antimicrobial anti-infective actives may be further subclassified as either narrow spectrum antimicrobials (i.e., affecting only a small subset of bacteria, e.g., gram-negative, etc.) or broad spectrum antimicrobials (i.e., affecting a wide variety). Examples include amikacin, gentamicin, geldanamycin, herbimycin, mupirocin, nitrofurantoin, pyrazinamide, quinupristin/dalfopristin, rifampin/ifonamide or tinidazole and the like.

The term "antiviral agent" includes any substance that inhibits or eliminates viral growth, pathogenesis and/or survival. This includes, for example, acyclovir, cidofovir, zidovudine, didanosine (ddI, VIDEX), zalcitabine (ddC, HMD), stavudine (d4T, ZERIT), lamivudine (3TC, EPIVIR), abacavir (ZIAGEN), Emtricitabine (EMTRIVA), and the like.

The term "antifungal agent" includes any substance that inhibits or eliminates fungal growth, pathogenesis and/or survival. This includes, for example, natamycin, rimocidin, felopine, nystatin, amphotericin B, candelilla, patchoul, neem seed oil, Coconut Oil, and the like.

The term "antiprotozoal agent" includes any substance that inhibits or eliminates the growth, pathogenesis, and/or survival of a protozoan organism (e.g., a parasite). Examples of antiprotozoal agents include antimalarial agents such as quinine, quinidine, and the like.

The term "immunomodulator" as used herein refers to a natural or synthetic active agent or drug that inhibits or modulates an immune response. The immune response may be a humoral response or a cellular response. The immunomodulator comprises an immunosuppressant.

The term "immune checkpoint molecule" means a class of inhibitory signaling molecules present in The immune system, which avoid tissue damage by modulating The persistence and intensity of The immune response in peripheral tissues, and are involved in maintaining tolerance to self-antigens (Pardol D M., The block of immune checkpoints in Cancer immunology. Nat Rev Cancer, 2012, 12(4): 252-. It has been found that one of the reasons why tumor cells can escape the immune system in vivo and proliferate uncontrollably is to utilize the inhibitory signaling pathway of immune checkpoint molecules, thereby inhibiting the activity of T lymphocytes, so that T lymphocytes cannot effectively exert a killing effect on tumors (Yao S, Zhu Y and Chen L., Advances in targeting cell surface signaling molecules for tumor modulation, Nat Rev Drug Discov, 2013, 12(2): 130-146). Immune checkpoint molecules include, but are not limited to, programmed death 1 (PD-1), PD-L1, PD-L2, cytotoxic T lymphocyte antigen 4 (CTLA-4), LAG-3, and TIM-3.

The term "co-stimulatory molecule" refers to a corresponding binding partner on a T cell that specifically binds to a co-stimulatory ligand, thereby mediating a co-stimulatory response (e.g., without limitation, proliferation) of the T cell. Costimulatory molecules are cell surface molecules that contribute to an effective immune response in addition to the antigen receptor or its ligand. Costimulatory molecules include, but are not limited to, MHC class I molecules, TNF receptor proteins, immunoglobulin-like proteins, cytokine receptors, integrins, signaling lymphocyte activation molecules (SLAM proteins), activating NK cell receptors, OX40, CD40, GITR, 4-1BB (i.e., CD137), CD27, and CD 28. In some embodiments, a "co-stimulatory molecule" is OX40, GITR, 4-1BB (i.e., CD137), CD27, and/or CD 28.

The term "cytokine" is a generic term for proteins released by one cell population that act on another cell as intercellular mediators. Examples of such cytokines are lymphokines, monokines, Interleukins (IL), such as IL-1, IL-1α, IL-2, IL-3, IL-4, IL-5, IL-6, IL-7, IL-8, IL-9, IL-11, IL-12, IL-15; tumor necrosis factors such as TNF-α or TNF-β; and other polypeptide factors, including LIF and Kit Ligand (KL) and interferon gamma. As used herein, the term cytokine includes proteins from natural sources or from recombinant cell culture and biologically active equivalents of the native sequence cytokines, including small molecule entities produced by artificial synthesis, and pharmaceutically acceptable derivatives and salts thereof.

The term "inhibitor" or "antagonist" includes substances that decrease certain parameters (e.g., activity) of a given molecule (e.g., an immune checkpoint molecule). For example, this term includes substances that cause a given molecule to be inhibited by at least 5%, 10%, 20%, 30%, 40% or more of the activity (e.g., PD-L1 activity). Thus, the inhibition need not be 100%.

The term "activator" includes substances that increase certain parameters (e.g., activity) of a given molecule (e.g., a co-stimulatory molecule). For example, this term includes substances that cause a given molecule to be increased by at least 5%, 10%, 20%, 30%, 40%, or more of the activity (e.g., OX40 activity). Thus, the activation effect need not be 100%.

The term "pharmaceutical excipients" refers to diluents, adjuvants (e.g., Freund's adjuvants (complete and incomplete)), excipients, carriers or stabilizers, etc., which are administered with the active substance.

The term "pharmaceutical composition" refers to such a composition that exists in a form allowing effective biological activity of the active ingredient contained therein, and does not contain additional ingredients having unacceptable toxicity to a subject to which the composition is administered.

The term "combination product" refers to a kit of a fixed combination, a non-fixed combination, or parts for combined administration in the form of a dosage unit, wherein two or more therapeutic agents can be independently administered simultaneously or separately administered within time intervals, especially when these intervals allow combination partners to exhibit collaboration, such as synergistic effect. The term "fixed combination" means that the antibody and combination partners (e.g., other therapeutic agents, such as immunomodulatory agents, such as immunosuppressive agents or anti-inflammatory agents) are administered to a patient simultaneously in the form of a single entity or dose. The term "non-fixed combination" means that the antibody of the invention and combination partners (e.g., other therapeutic agents, such as immunomodulatory agents, such as immunosuppressive agents or anti-inflammatory agents) are administered to a patient as separate entities simultaneously, concurrently, or sequentially, without specific time limitation, wherein such administration provides therapeutically effective levels of the two compounds in the patient. The latter also applies to a cocktail therapy, e.g., administration of three or more therapeutic agents. In one preferred embodiment, the drug combination is a non-fixed combination.

"Immunogenicity" refers to the ability of a particular substance to elicit an immune response. Tumors are immunogenic and enhancing tumor immunogenicity helps to eliminate tumor cells by an immune response.

An "immune response" refers to a biological response in vertebrates against foreign substances that protects an organism from these substances and the diseases caused by them. The immune response is mediated by the action of cells of the immune system (e.g., T lymphocytes, B lymphocytes, Natural Killer (NK) cells, macrophages, eosinophils, mast cells, dendritic cells, or neutrophils) and soluble macromolecules produced by these cells or the liver, including antibodies, cytokines, and complements, which result in the selective targeting, binding, damage, destruction, and/or elimination of invading pathogens, cells, or tissues infected with pathogens, cancerous or other abnormal cells, or (in the case of autoimmunity or pathological inflammation) normal human cells or tissues from the vertebrate body. Immune responses include, for example, activation or suppression of T cells, e.g., effector T cells or Th cells, such as CD4+ or CD8+ T cells, or suppression or depletion of Treg cells. "T effector" ("$T_{eff}$") cells refer to T cells with cytolytic activity (e.g., CD4+ and CD8+ T cells) and T helper (Th) cells that secrete cytokines and activate and direct other immune cells, but regulatory T cells (Treg cells) are not included.

The term "effective amount" refers to an amount or dosage of the antibody, fragment, conjugate or composition of the invention which generates expected effects in a patient in need of treatment or prevention after administered to the patient in a single or multiple doses. The effective amount can be easily determined by an attending physician as a person skilled in the art by considering a variety of factors as follows: species such as mammals; its size, age, and general health condition; the specific disease involved; the extent or severity of the disease; response in an individual patient; specific antibody administered; route of administration; bioavailability characteristics of the administered formulation; selected dosage regimen; and use of any concomitant therapy.

The "therapeutically effective amount" refers to an amount effective to achieve a desired therapeutic result at a necessary dosage for a desired period of time. The therapeutically effective amount of an antibody or antibody fragment, or conjugate or composition thereof may vary depending on a variety of factors such as morbid state, age, sex, and weight of an individual, and the ability of the antibody or antibody portion to elicit a desired response in an individual. The therapeutically effective amount is also such an amount that any toxic or undesired effect of the antibody or antibody fragment, or conjugate or composition thereof is inferior to the therapeutically beneficial effect. "Therapeutically effective amount" preferably inhibits a measurable parameter (e.g., swelling rate, etc.) by at least about 20%, more preferably at least about 40%, even more preferably at least about 50%, 60%, or 70%, and still more preferably at least about 80% or 90%, relative to untreated subjects. The capacity of a compound to inhibit a measurable parameter (e.g., swelling rate) can be evaluated in an animal model system that predicts efficacy in human autoimmune diseases or inflammation.

The "prophylactically effective amount" refers to an amount effective to achieve a desired prophylactic result at a required dosage for a desired period of time. Generally, since a prophylactic dose is administered in a subject before or at an earlier stage of a disease, a prophylactically effective amount will be less than a therapeutically effective amount.

The terms "individual" or "subject" as used herein are used interchangeably and include mammals. Mammals include, but are not limited to, domestic animals (e.g., cows, sheep, cats, dogs, and horses), primates (e.g., humans and non-human primates such as monkeys), rabbits, and rodents (e.g., mice and rats). In some embodiments, the individual or subject may be a mammal, e.g., a primate, preferably a higher primate, e.g., a human (e.g., a patient having or at risk of having a disease described herein). In one embodiment, the subject has or is at risk of having a disease described herein (e.g., a tumor or infection as described herein). In certain embodiments, the subject receives or has received other treatment, such as chemotherapy treatment and/or radiation therapy. Alternatively, or in combination, the subject is or is at risk of being immunocompromised due to the infection.

The term "combination therapy" refers to the administration of two or more therapeutic agents or modalities (e.g., radiation therapy or surgery) to treat IL-23 associated diseases as described in this disclosure. Such administration includes co-administration of these therapeutic agents in a substantially simultaneous manner, for example, in a single capsule with a fixed proportion of active ingredients. Alternatively, such administration includes co-administration of each active ingredient in a variety of or separate containers (such as tablets, capsules, powder and liquid). The powder and/or liquid can be reconstituted or diluted to a desired dosage before administration. In addition, such administration also includes using each type of therapeutic agents in a sequential manner at approximately the same time or at different times. In any case, the therapeutic regimen will provide the beneficial effect of the drug combination in the treatment of disorders or symptoms described herein.

As used herein, "treatment" (or "treat" or "treating") refers to slowing, interrupting, arresting, alleviating, stopping, reducing, or reversing the progression or severity of an existing symptom, disorder, condition, or disease.

As used herein, "prevention" (or "prevent" or "preventing") includes the inhibition of the onset or progression of a disease or disorder or a symptom of a specific disease or disorder. In some embodiments, subjects with family history of immune system diseases (autoimmune diseases or inflammation) are candidates for preventive regimens. Generally, in the context of immune system diseases (autoimmune diseases or inflammation), the term "prevention" refers to the administration of a drug prior to the onset of conditions or symptoms of immune system diseases (autoimmune diseases or inflammation), particularly in subjects at risk of immune system diseases (autoimmune diseases or inflammation).

"Subject/patient sample" refers to a collection of cells or fluids obtained from a patient or a subject. The source of tissue or cell samples can be solid tissues, e.g., from fresh, frozen and/or preserved organ or tissue samples or biopsy samples or puncture samples; blood or any blood component; body fluids such as cerebrospinal fluids, amniotic fluids, peritoneal fluids, or interstitial fluids; and cells from a subject at any time during pregnancy or development. Tissue samples may comprise compounds which are naturally not mixed with tissues, such as preservatives, anticoagulants, buffers, fixatives, nutrients, antibiotics, and the like.

These and other aspects and embodiments of the invention are described in the Figures (brief description of the Figures follows) and in the following detailed description of the invention and are illustrated in the following examples. Any or all of the features discussed above and throughout this application may be combined in various embodiments of the invention. The following examples further illustrate the invention; however, it is to be understood that the examples are described by way of illustration and not limitation, and that various modifications may be made by those skilled in the art.

EXAMPLES

Example 1 Construction of Reporter Cell Line Jurkat/NF-kB-GFP+hCD40

There are a plurality of NF-kB transcription factor binding elements in the promoter of NF-kB-GFP reporter gene lentivirus system (QIAGEN, CCS-013G), and the activation of the promoter can drive the expression of GFP. Jurkat cells (ATCC, TIB-152) were infected with NF-κB-GFP reporter lentivirus and lentivirus-infected Jurkat cells were screened with puromycin (InvivoGen, ant-pr-1) according to the kit instructions. Cells screened with puromycin were stimulated by addition of 10 ng/ml TNFα protein (Sino Biological, 10602-HNAE) for 24 h, and flow cytometry (BD, FACSAria III) were used to sort cell subsets of GFP-fluorescent to obtain Jurkat/NF-κB-GFP cells.

Human CD40 CDS (Sino Biological, HG 10774-M) was constructed into lentiviral core plasmid pCDH (Systems Biosciences). The obtained lentiviral core plasmid and helper plasmid pPACKH1-GAG, pPACKH1-REV, pVSVG (all from System Biosciences) were co-transfected at 1:1:1:1 into 293FT cells (Thermo Fisher Scientific, R70007) with PEI (polyscience, 24885-2) using standard procedures. 6 h after the transfection, the medium is replaced. The culture is in DMEM medium (Life technologies, C11995500 CP) containing 10% fetal bovine serum (Biological Industries, 04-001-1A) at 37° C. and the supernatant containing human CD40 lentivirus is collected after a further 48 h of culture.

The positive control CD40L sequence used herein was from Patent WO 2016/177771 (SEQ ID NO: 15) and the negative control HEL sequence is shown in Table 10. The DNA sequences of CD40L and HEL were subjected to full gene synthesis in GENEWIZ, Inc. For the purification of CD40L and HEL, the DNA sequences were inserted into the eukaryotic expression vector pFUSE (InvivoGen, pFUSE-hg1fc 1) and then transfected into 293F cells (Thermo Fisher Scientific, R79007) with PEI using standard procedures; cells were shaking-bed cultured at 37° C. using Freestyle medium (Life technologies, 12338026). After 7 days of culture, the supernatant was collected and purified on AKTA system (GE) using Superdex™ 200 Increatase prepacked column (GE, 28-9909-44).

CD40 signaling activates the NF-κB pathway, and if CD40 is successfully expressed on the cell membrane surface of Jurkat/NF-κB-GFP, CD40L stimulation would induce the expression of GFP. Constructed Jurkat/NF-κB-GFP cells sorted as described above were infected with human CD40 lentivirus supernatant obtained as described above, and after 16 h, 100 nM of the above-obtained CD40L protein (as positive control) and HEL (as negative control) were added to stimulate for 24 h, followed by sorting for with the strongest GFP fluorescence into 96 well plates using single cell sorting by flow cytometer.

Figure 1:
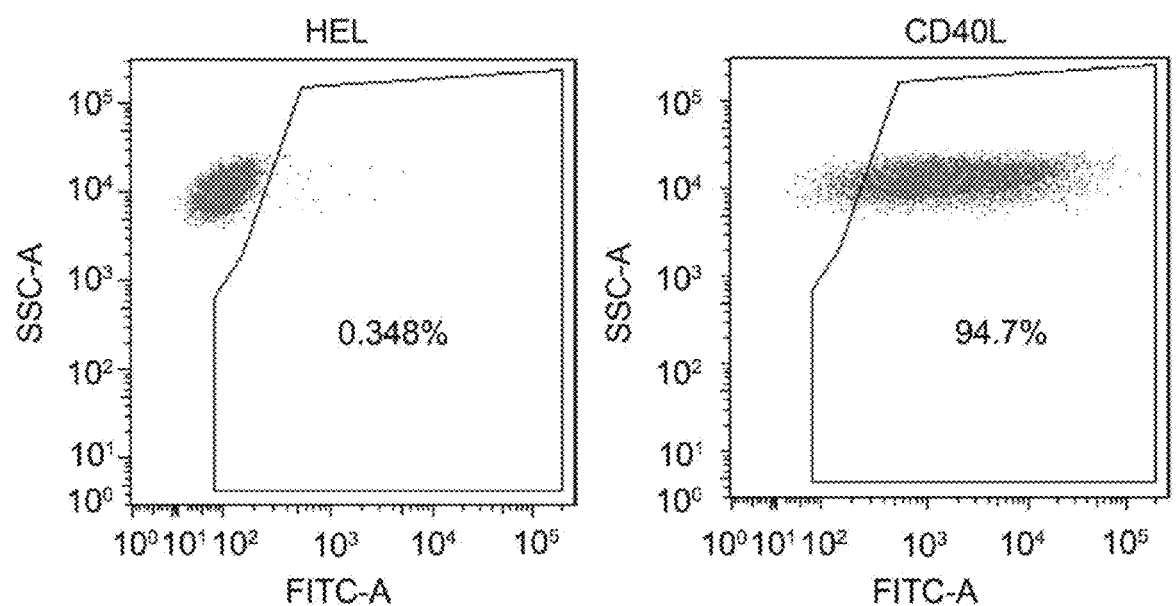
FIG. 1 shows the activation of single clone of Jurkat/NF-κB-GFP+hCD40 reporter cells by HEL and CD40L produced by 293F cells, as determined through flow cytometry, and the activation of reporter cells was followed by GFP expression, the positive rate of which was detected via the FITC channel.

The above-mentioned cells in the 96-well plate were cultured in RPMI 1640 medium (Lifetechnologies, C11875500 CP) containing 10% fetal bovine serum (Biological Industries, 04-001-1A) for 2 weeks. After the growing-up of single cells, 100 nM of the trimerized CD40L protein (as positive control) and HEL (as negative control) obtained above were added, and single clones that were strongly positive for CD40L and negative for HEL were selected as the Jurkat/NF-κB-GFP+hCD40 (NF-κB-GFP+hCD40 for short) cells for the subsequent experiments. The results were shown in FIG. 1, the GFP positive rate for Jurkat/NF-kB-GFP+hCD40 single clones after CD40L stimulation being 94.7%, with no activation after HEL stimulation.

Example 2 Screening of Phage Display Antibody Libraries for CD40 Binding Antibodies Peripheral blood of 30 healthy adults was purchased from Tianjin Blood Center and Miaotong (Shanghai) Biological Science & Technology Co. Ltd., and PBMC was obtained by centrifugation using ficoll separation liquid (Tian Jin Hao Yang Biological Manufacture Co., Ltd, LDS 1075), and the centrifugation conditions were as follows: 20° C., 2000 rpm, up-5-down-0 mode for 30 minutes. Human natural antibody libraries were constructed using PBMCs obtained as described above, the library construction being by conventional methods (phage display, Tim Clackson and Henry B. Lowman). The obtained antibody heavy chain and light chain variable regions are randomly combined and displayed on the N-terminal of the phage capsid protein pIII in the form of single-chain antibody scFv to obtain a phage display antibody library with a library capacity of up to $10^{10}$.

Phage screening is conventional techniques (Phage Display: A Laboratory Manual, Carlos F Barbas III). Firstly, biotinylated CD40 protein (acrobiosystems, TN5-H82F9) was incubated with the phage display antibody library obtained as described above for 2 h at room temperature. After the incubation was complete, 150 ul streptavidin magnetic beads Dynabeads M280 (Life technologies, 11205D) were added directly and incubated for 30 min on a homogenizer at room temperature. Phages that did not bind to the antigen were washed off with 0.05% PBS-Tween (PBS: Life technologies, 70011044; Tween: Sigma-Aldrich, 9005-64-5), and finally the phages bound to the antigen were eluted with 0.2M glycine-HCl (pH 2.2). *E. Coli* XL1-blue (Agilent, 200236) was infected with the eluted phage and amplified after the addition of the helper phage VCSM13 (Agilent, 200251) for the next round of screening. Three rounds of screening were performed in total. After the three rounds, antibody phages bound to CD40 were enriched and the screening results are shown in Table 1.

TABLE 1 screening of human natural antibody libraries for CD40-binding antibodies using phage display technology

| | | First round | Second round | Third round |
|---|---|---|---|---|
| CD40 | The starting number | $5.4 \times 10^{13}$ | $8 \times 10^{12}$ | $9.2 \times 10^{12}$ |
| | The acquisition number | $8 \times 10^{6}$ | $3 \times 10^{7}$ | $2 \times 10^{9}$ |

Figure 2A:
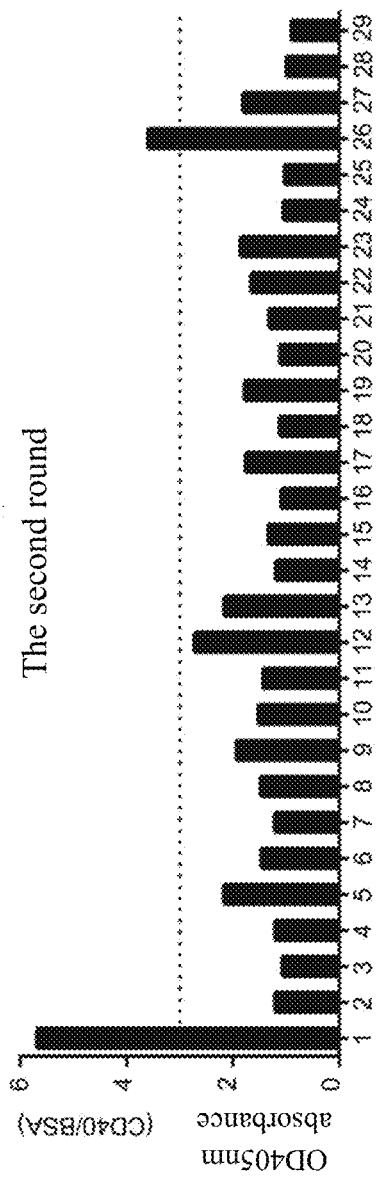
FIGS. 2A-2B show the positive rate of CD40-binding antibodies in the antibody library obtained by phage ELISA assay for the second (FIG. 2A) and third (FIG. 2B) rounds of phage display enrichment, with antibodies with its binding to CD40 more than three times greater than the binding signal to BSA defined as positive antibodies.
Figure 2B:
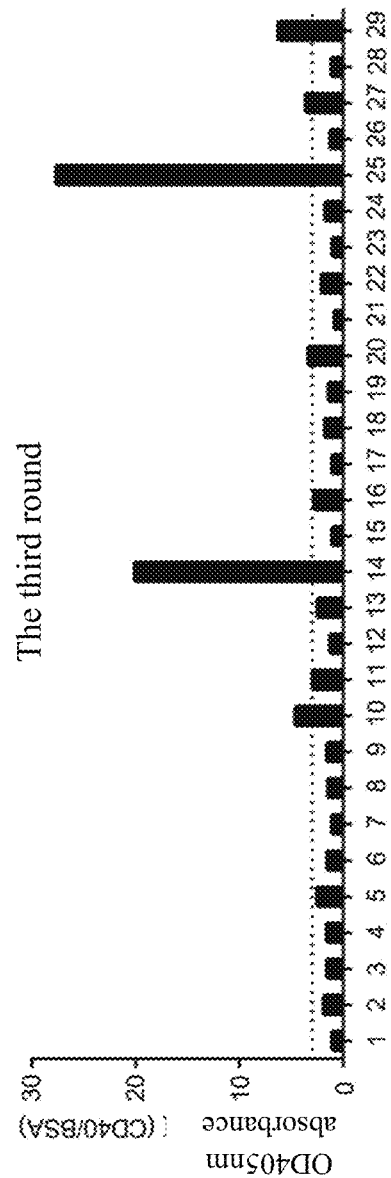

To preliminarily evaluate the positive rate of the screened for CD40-binding antibodies, we picked 29 phage single clones from the second and third round respectively, for phage ELISA analysis. Phage ELISA is a routine technique, as follows: picking 29 phage single clones from both of the phage single clones of the second and third round cultured in the deep-well plates, respectively, and shaking at 37° C. and 300 rpm until OD=0.5-0.8, then adding helper phage VCSM13 to amplify, followed by inducing the phage overnight at 30° C. for antibody expression. 1 µg/ml human CD40 (Acrobiosystems, CD 0-H5228) was coated on ELISA plates (Corning, 3690) and incubated overnight at 4° C. The ELISA plates incubated overnight were loaded with overnight-induced phage supernatants, incubated for 1 h at room temperature, and washed 8 times with 0.05% PBST. BSA (Solarbio, A8020-100) was used as a negative control. Bound antibody phage was detected by the addition of HRP-conjugated anti-M13 (GE, 27-9421-01, M13 is the phage capsid protein). Positive clones were defined as the binding signal to CD40 being more than three times the binding signal to BSA. The results are shown in FIG. 2, in which the positive rates for the second round of screening and the third round of screening are 6.9% and 27.6%, respectively.

Example 3. Agonist Antibody Screening for the Costimulatory Molecule CD40

Figure 3:
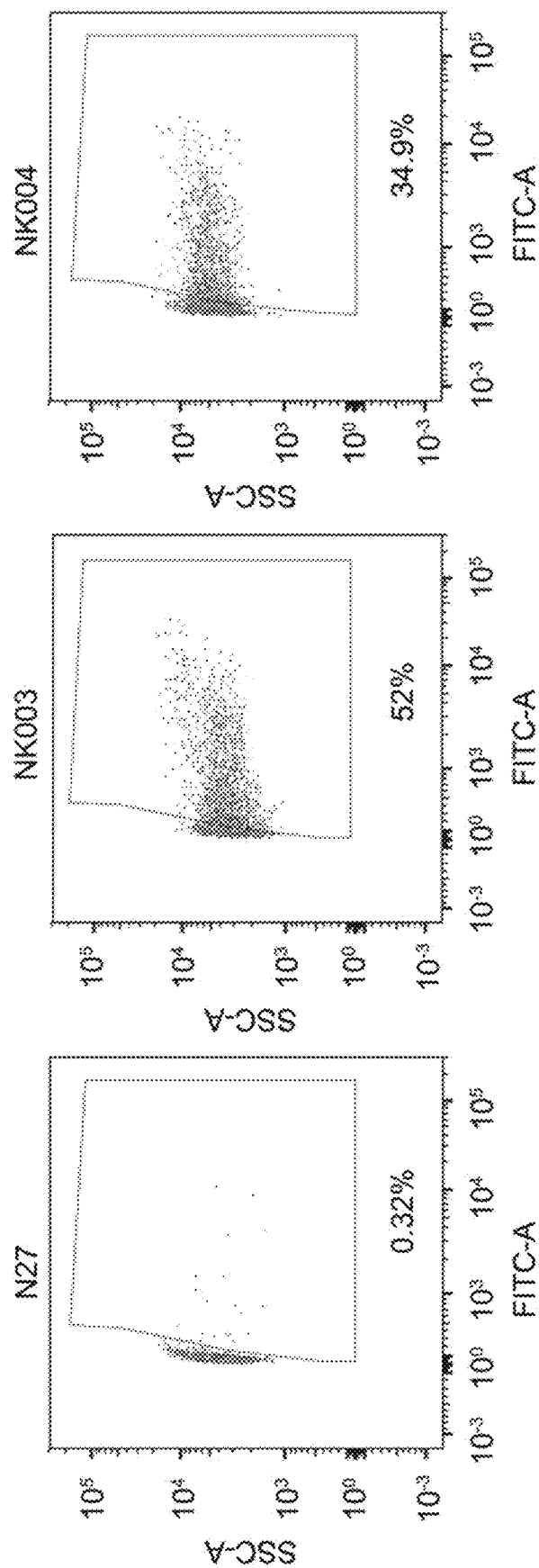
FIG. 3 shows the activation of Jurkat/NF-κB-GFP+hCD40 reporter cells by supernatants containing negative control N27, positive CD40 agonist antibodies produced from a single clone of Jurkat/NF-κB-GFP+hCD40 reporter cells, as determined through flow cytometry. The fluorescence intensity of GFP detected in the FITC channel represents the degree of activation of the monoclonal.

At first, we subcloned the enriched antibodies from the third round of phage display into the secretory lentiviral vector pCDH while cloning the N27 ScFv, the sequence of which is shown in table 11, into the secretory lentiviral vector pCDH as a negative control. 293FT cells were co-transfected with a lentivirus core plasmid and helper plasmids pPACKH1-GAG, pPACKH1-REV and pVSVG at 1:1:1:1, followed by a replacement of medium 6 h later, and a further 48 h of continuous culture in a DMEM medium containing 10% fetal bovine serum (Biological Industries, 04-001-1A) at 37° C., and the supernatant containing the lentivirus library of the CD40-binding antibody is collected; 50000 pg of the obtained lentivirus library of the CD40-binding antibody is used to infect HEK293 cells, after infecting for 16 h, the culture medium containing lentivirus is disgarded by centrifugation and a fresh culture medium is added. The infected HEK293 cells were sorted into a 96-well plate using a flow cell sorting technique, so that each well contains 1 infected HEK293 cell only. After the cells were cultured for 3 weeks to reach a certain amount, the supernatant was taken and had $3\times10^5$ Jurkat/NF-κB-GFP+ hCD40 reporter cells obtained as described above added, together with a secondary antibody of 2.5 µg/ml goat anti-human Fc (Southern Biotech, SBA-2048-01) to crosslink the antibody secreted from the cells to enhance the activating intensity of the agonist antibody. After 24 h of culture, the activity of the cell supernatant was tested, and the detection result of the positive antibody is shown in FIG. 3. Genes of the antibodies are extracted from HEK293 cells with positive cell supernatant activity, and constructed to pFUSE vectors for sequencing to obtain positive antibody VH and VL sequences. The two positive antibodies obtained are numbered as NK003 and NK004, and the sequences thereof (including CDR, VH/VL, heavy chain and light chain) are referred to sequences in tables 4 to 8 of the sequence listing.

Example 4. Expression and Purification of Full-Length Antibody IgG

The expression and purification of the antibody are conventional methods, and are specifically as follows:

The heavy and light chain DNA of selected agonist antibodies NK003, NK004 were synthesized according to antibody sequence (GENEWIZ, Inc.), cloned into the vector pFUSE separately and respectively, and the plasmids containing the heavy and light chains, respectively, were transiently co-transfected into 293F suspension cells at 1:1 to express full length antibody. After 1 week of culture, purification was performed on AKTA system using Superdex™ 200 Increatase pre-packed column.

Figure 4:
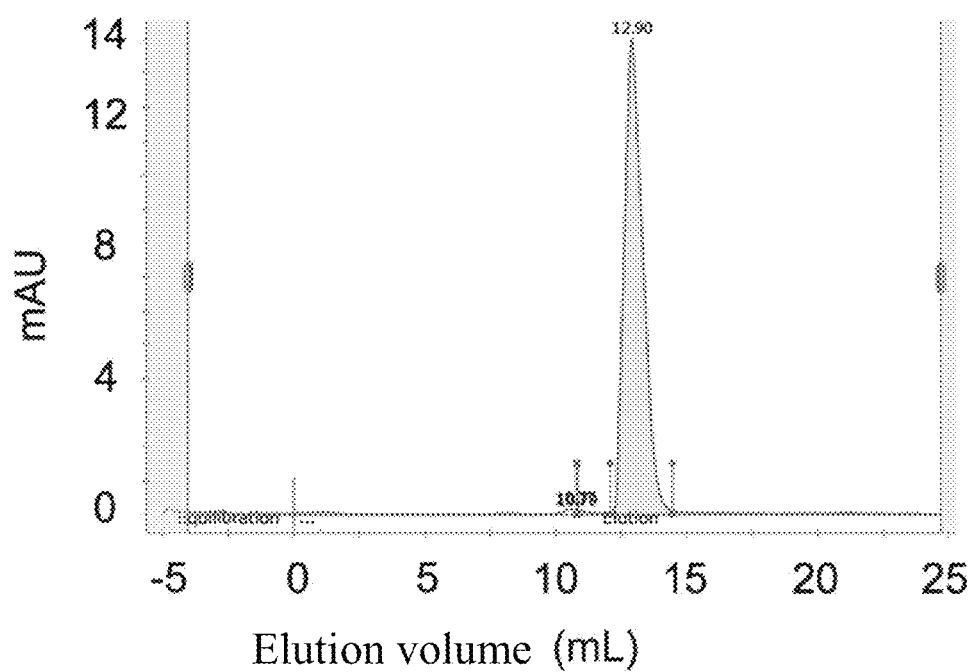
FIG. 4 shows the polymer nature of the antibody NK003 of the invention produced by 293F cells as determined by size exclusion chromatography.

The purified antibody was identified by SDS-PAGE and the aggregation of the antibody was analyzed using size exclusion pre-packed column Superdex 200. The results are shown in FIG. 4, wherein NK003 elution peak shape is symmetry and retention time at elution remained consistent with that of a monoclonal antibody having a molecular weight of a single molecule, while a small amount of aggregates were present in the antibody.

Example 5. In Vitro Characterization of Human CD40 Antibodies NK003 and NK004

5.1 Binding of NK003, NK004 to CD40

Figure 5A:
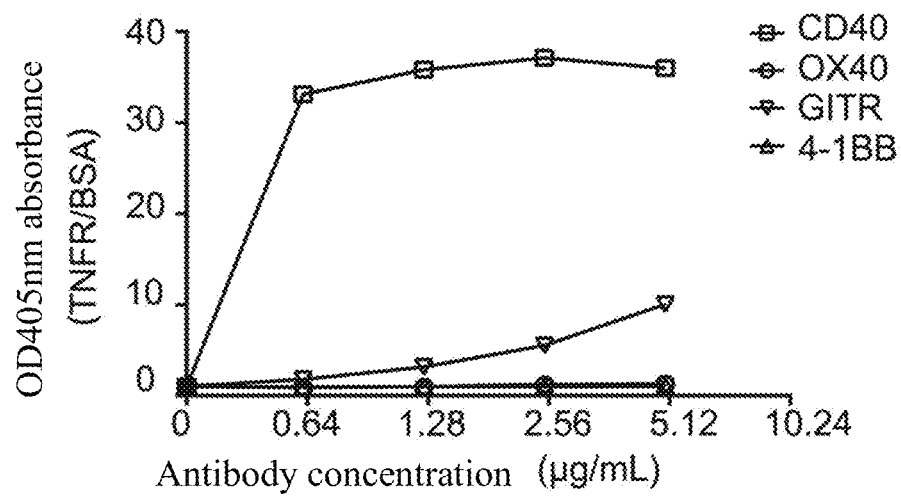
FIG. 5A shows that the antibody NK003 of the present invention produced by 293F cells specifically binds to CD40 and does not bind or binds poorly to the other TNFR family members OX40, 4-1BB, GITR, as determined by ELISA.

NK003 binding selectivity was evaluated by direct ELISA with TNFR family members OX40, 4-1BB and GITR. PBS solutions containing 1 µg/ml of human OX40 (Acrobiosystems, OX 0-H5224), 4-1BB (Acrobiosystems, 41B-H5227), GITR (Acrobiosystems, GIR-H5228) and CD40 (Acrobiosystems, CD 0-H5228) were coated on the ELISA plates and incubated overnight at 4° C. NK003 diluted with PBS to different concentrations as obtained in example 4 was added: 0.625 µg/ml, 1.25 µg/ml, 2.5 µg/ml and 5 µg/ml. After 30 mins of incubation at room temperature, washing was carried out for 8 times with 0.05% PBS-Tween. Bound NK003 was detected by addition of goat anti-human HRP conjugated Fc antibody (southern biotech, 2048-05). As shown in FIG. 5A, NK003 selectively binds to human CD40 with low or no binding to other TNFR family proteins tested.

Figure 5B:
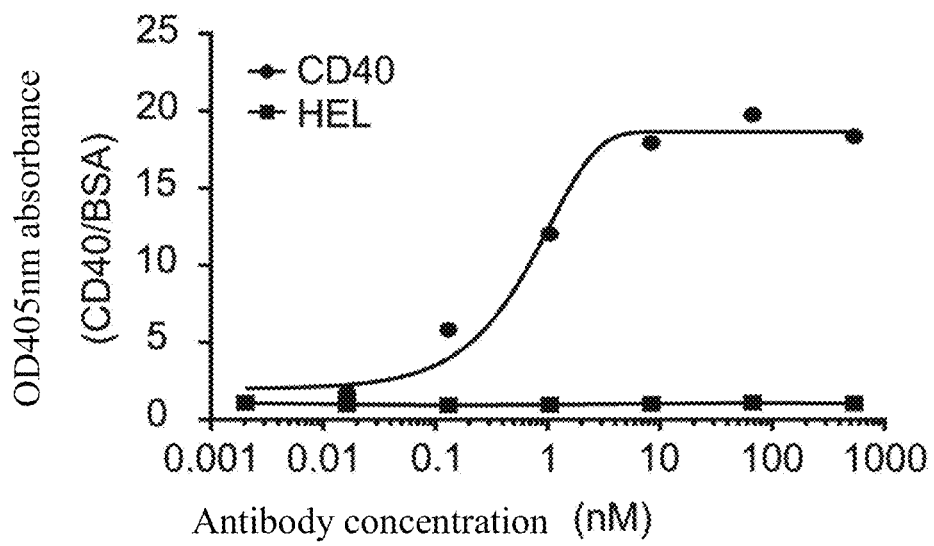
FIG. 5B shows the specific binding of the antibody NK004 of the invention to CD40 produced by 293F cells as determined by ELISA.

To evaluate NK004 binding to CD40, 1 µg/ml PB solution of human CD40 (Acrobiosystems, CD 0-H5228) was coated on the ELISA plates and incubated overnight at 4° C. NK004 diluted with PBS to different concentrations as obtained in Example 4 was added NK004: 0.002 nM, 0.016 nM, 0.13 nM, 1 nM, 8 nM, 64 nM and 500 nM, with HEL being a negative control antibody. The antibodies were incubated at room temperature for 30 min, and washed 8 times with 0.05% PBS-Tween. Bound NK004 was detected by addition of goat anti-human HRP conjugated Fc antibody. As shown in FIG. 5B, NK004 can bind to human CD40.

5.2 NK003 Blocks the Binding of CD40L to CD40

Figure 6:
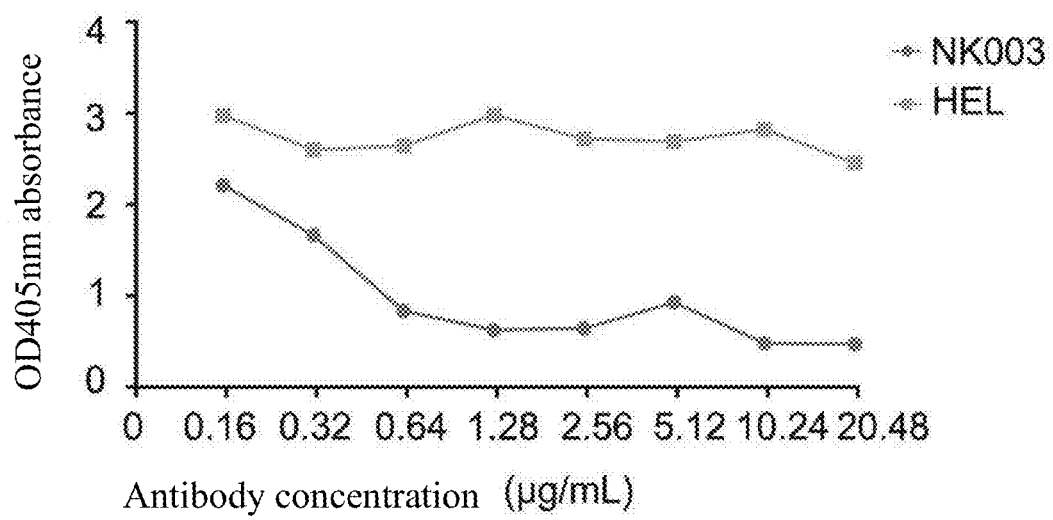
FIG. 6 shows that the antibody NK003 of the present invention produced by 293F cells competed with CD40L for binding to CD40 as determined by ELISA.

The effect of NK003 on the binding of CD40L to CD40 was evaluated by ELISA. Firstly, CD40L was biotinylated using a protein biotinylation kit (GeneCopoeia, BI 001) according to the instructions. 1 µg/ml human CD40 was coated on the ELISA plates and incubated overnight at 4° C. NK003 diluted with PBS to different concentrations as obtained in example 4 was added NK003: 0.156 µg/ml, 0.313 µg/ml, 0.625 µg/ml, 1.25 µg/ml, 2.5 µg/ml, 5 µg/ml, 10 µg/ml and 20 µg/ml, with HEL being a control antibody. After 1 h incubation at room temperature, 2.5 µg/ml biotinylated CD40L was added, and after 30 mins incubation at room temperature, washing was carried out 8 times with 0.05% PBS-Tween. After addition of Streptavidin-HRP, OD405 values were read using a microplate reader (SpectraMax i3x) to detect the amount of bound CD40L to CD40. As shown in FIG. 6, the results are that NK003 blocked the binding of CD40 to CD40L.

Figure 7A:
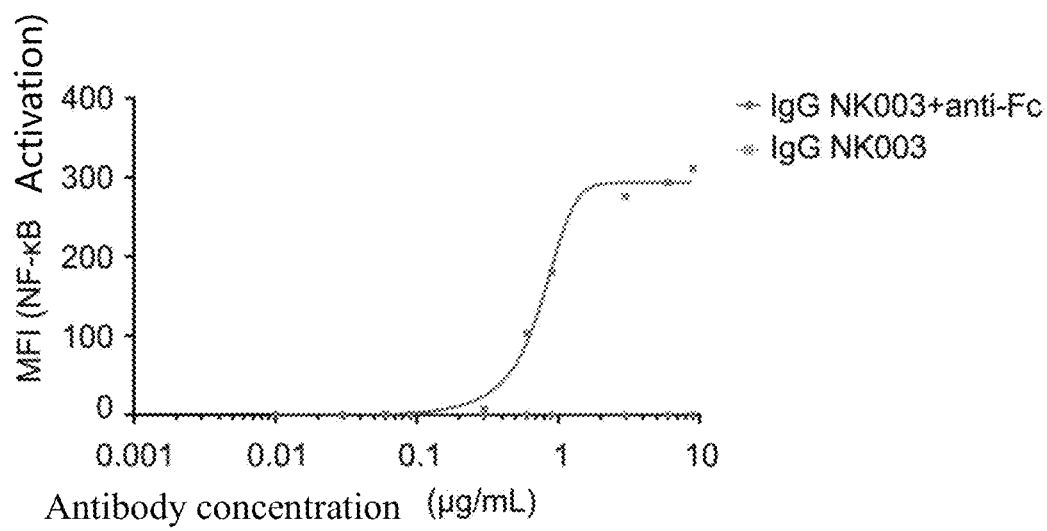
FIG. 7A shows that the antibody NK003 of the present invention produced by 293F cells activates the Jurkat/NF-κB-GFP+hCD40 reporter cells in a cross-linked form, as determined by flow cytometry.
Figure 7B:
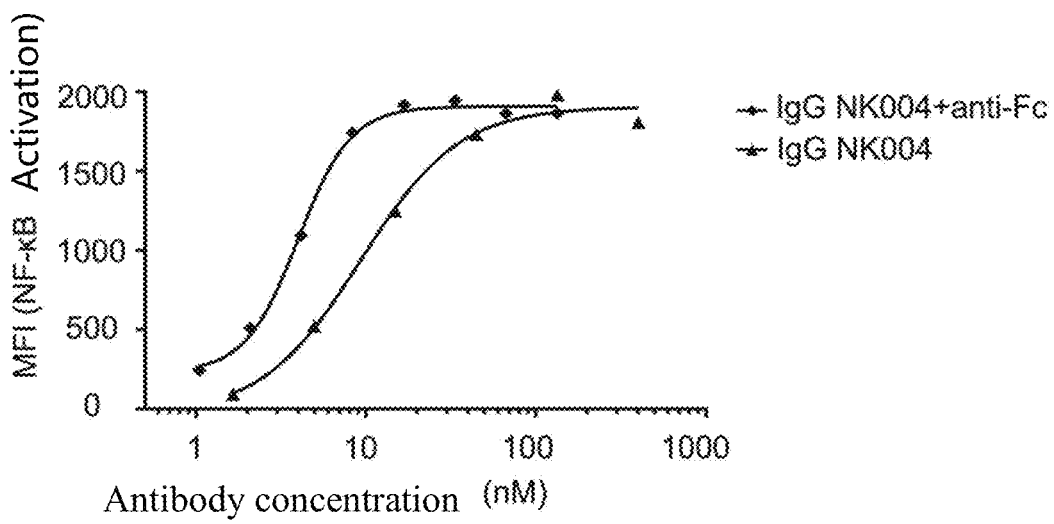
FIG. 7B shows that the antibody NK004 of the present invention produced by 293F cells activates the Jurkat/NF-κB-GFP+hCD40 reporter cells in a constitutive form independent of cross-linking, as determined by flow cytometry. GFP is detected in the FITC channel, and MFI is defined as the product of the Geometric Mean of GFP-positive cells and the percentage of GFP-positive cells.

5.3 NK003 and NK004 Activate NF-kB-GFP+hCD40 Reporter Cell Line in a Cross-Linked Form In this example, the activation of NF-κB-GFP+hCD40 reporter cell line by NK003, NK004 antibodies was detected by flow cytometry, and the EC50 of the two antibodies was determined, specifically as follows:

$3\times10^5$ cells/tube NF-κB-GFP+hCD40 reporter cells as obtained in example 1 were respectively fetched and added into NK003 or NK004 as obtained in Example 4 and diluted to different concentrations: 0.001 μg/ml, 0.005 μg/ml, 0.01 μg/ml, 0.05 μg/ml, 0.1 μg/ml, 0.5 μg/ml, 1 μg/ml, 5 μg/ml and 10 μg/ml, using HEL antibody as a negative control; for cross-linking, a secondary antibody, goat anti-human Fc, was added to each group simultaneously at a concentration of 2.5 μg/ml. After co-culture in RPMI 1640 medium (Life technologies, C11875500 CP) containing 10% fetal bovine serum (Biological Industries, 04-001-1A) at 37° C. for 24 h, the cells were washed with PBS for three times and analyzed using flow cytometry. The data obtained were fitted to curves using GraphPad Prism 6.0 and EC50 was calculated. As a result, as shown in FIG. 7, NK003 relied on cross-linking of secondary antibodies to activate CD40 and activated the NF-κB-GFP+hCD40 reporter cell line in a cross-linked form, with EC50 at 2 nM (FIG. 7A). NK004 activated CD40 independently of secondary antibody cross-linking, activating the NF-κB-GFP+hCD40 reporter cell line in a constitutive form, with EC50 at 4 nM with the addition of the secondary antibody (FIG. 7B).

5.4 Quantitative Analysis of NK003 Dynamics and Affinity by Surface Plasmon Resonance Biacore T200 (GE Healthcare) was used to detect the affinity of the antibodies NK003, NK004. NK003, NK004 were passed through the Protein A chip at 10 μL/min and captured onto the chip. The antigen to be tested, i.e. human CD40 recombinant protein (Acrobiosystems, CD 0-H5228) was diluted gradiently with a Running buffer (HBS-EP+, GE) at concentrations of 2 μM, 1 μM, 500 nM, 250 nM, 125 nM, 62.5 nM, 31.25 nM. The above-mentioned CD40 with different concentrations was flowed through the chip on which the antibody was captured at a flow rate of 30 μL/min for 120 s of binding, and then the Running buffer was flowed through the chip at a flow rate of 30 μL/min for 240 s, with the antigen dissociating gradually from the chip on which the antibody was captured. Data processing was performed using BIAevaluation software S200, the necessary software of Biacore T200 instrument and binding constants (Ka), dissociation constants (Kd), and equilibrium dissociation constants ($K_D$) were calculated. The results are shown in Table 2.

TABLE 2 measurement of affinity of antibody to human CD40 using surface plasmon resonance technology platform

| Sensors | Antibodies | Antigen(s) | ka (1/Ms) | kd (1/s) | $K_D$ (M) |
|---|---|---|---|---|---|
| Protein A | NK003 | CD40 | 3.67E+04 | 1.21E−02 | 3.31E−07 |
| Protein A | NK004 | CD40 | 8.87E+04 | 3.90E−02 | 4.40E−07 |

5.5 NK003 Cross Reaction

The binding of NK003 to 293FT cells expressing Rhesus and human CD40 was detected by flow cytometry and the cross-reactivity of NK003 to Rhesus and human CD40 was determined.

The CDS region of Rhesus monkey CD40 (NCBI, NM_001265862.1) and human CD40 (NCBI, NM_001250.5) (GENEWIZ, Inc synthesis) were cloned into pCDH vector, then transiently transfected into 293FT cells with PEI using standard procedures, the medium was replaced after 6 h and cells were cultured in DMEM medium containing 10% fetal bovine serum (Biological Industries, 04-001-1A) at 37° C. Cells expressing Rhesus monkey CD40 and human CD40, respectively, were obtained after 48 h of expression.

Figure 8A:
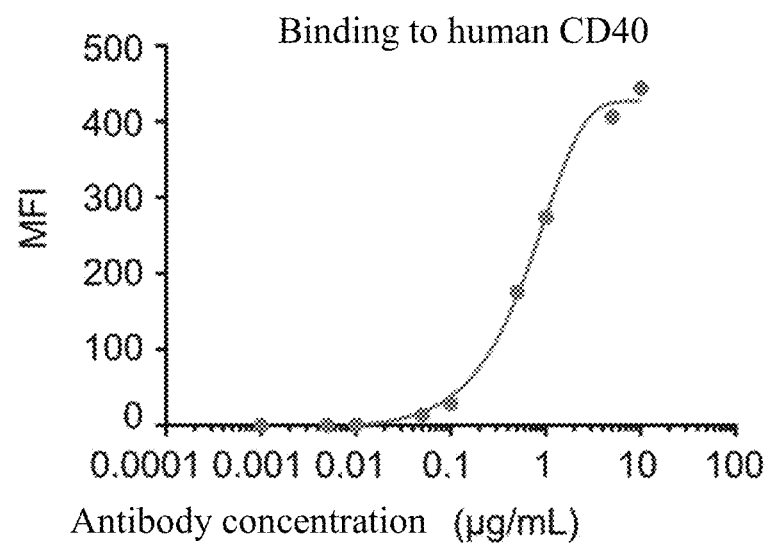
FIGS. 8A-8B show the binding of the distribution of the antibody NK003 of the invention produced by 293F cells to 293FT cells overexpressing human CD40 (FIG. 8A), 293FT cells overexpressing Rhesus CD40 (FIG. 8B), as determined by flow cytometry.
Figure 8B:
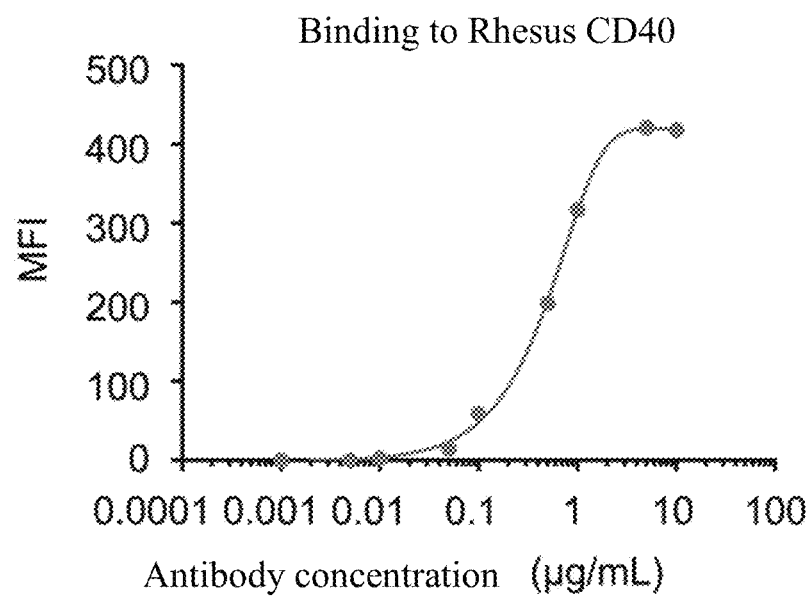

The 293FT cells expressing Rhesus monkey and human CD40 obtained as described above were taken $3\times10^5$ cells/tube, respectively, and added into NK003 as obtained in Example 4 and diluted to different concentrations with PBS: 0.001 μg/ml, 0.005 μg/ml, 0.01 μg/ml, 0.05 μg/ml, 0.1 μg/ml, 0.5 μg/ml, 1 μg/ml, 5 μg/ml and 10 μg/ml, with HEL 10 μg/ml being negative controls. Cells were incubated with different concentrations of NK003 at 4° C. for 30 min, washed three times with PBS, and then supplemented with Alexa Fluro 488 goat anti-human Fc fluorescent secondary antibody (Lifetechnologies, A11013) at 1:100, and the mixture was incubated at 4° C. in the dark for 30 min and then analyzed by flow cytometry. GraphPad Prism 6.0 was used to fit the curves and calculate EC50. As the result shown in FIG. 8, it can be seen that NK003 cross-reacts with both Rhesus CD40 (FIG. 8B) and human CD40 (FIG. 8A), EC50 for the binding to Rhesus CD40 is 8 nM and for the binding to human CD40 is 10 nM.

5.6 NK003 Induces Apoptosis of Tumor Cells

Lymphoma cells Raji and Ramos have expression of CD40 of the membrane surface, and we tested the ability of NK003 to promote apoptosis of tumor cells using Raji cells (ATCC, CRL-7936) and Ramos cells (ATCC, CRL-1596).

Figure 9A:
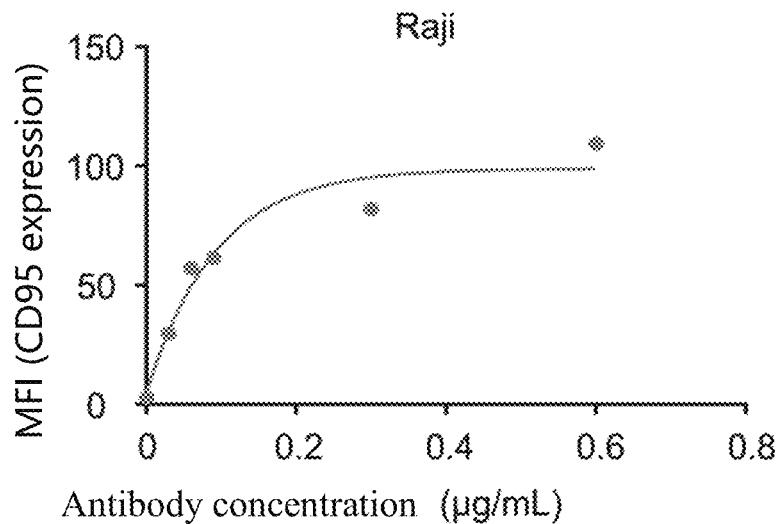
FIGS. 9A-9B show the antibody NK003 of the present invention produced by 293F cells induces apoptosis of Raji cells (FIG. 9A) and Ramos cells (FIG. 9B), as determined by flow cytometry, and the apoptosis index is the expression of CD95. MFI was defined as the product of the geometric mean of CD95-positive cells and the percentage of CD95-positive cells.
Figure 9B:
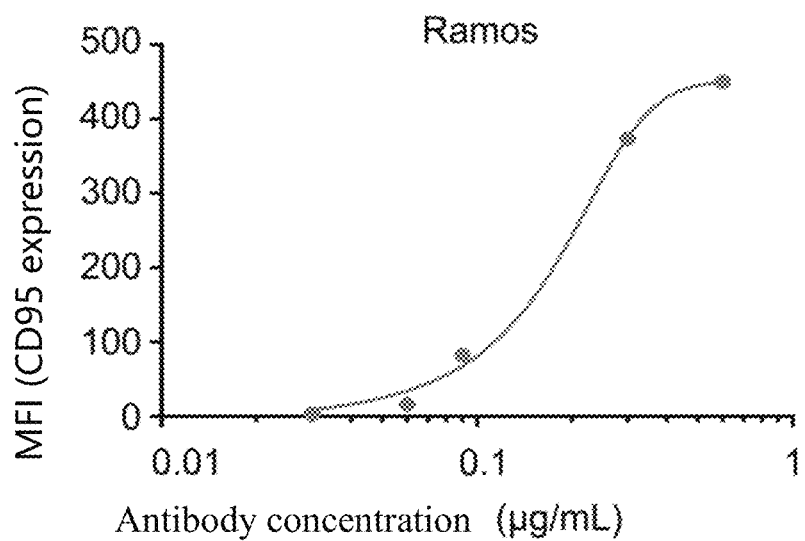

Raji and Ramos cells were seeded in 24-well plates at a density of $3\times10^5$/mL, cultured in RPMI 1640 medium containing 10% fetal bovine serum (life technologies, 10091148), and cell seeding was performed simultaneously with the addition of NK003 as obtained in Example 4 and diluted to different concentrations with PBSNK003: 0.03 μg/ml, 0.06 μg/ml, 0.09 μg/ml, 0.3 μg/ml, 0.6 μg/ml, 0.9 μg/ml, 3 μg/ml, 6 μg/ml and 9 μg/ml, with HEL at 9 μg/ml as a negative control, and goat anti-human Fc was also added as a crosslinking agent at a concentration of 2.5 μg/ml per well. After the coculture for 24 h, washing was carried out three times with PBS, and PE-CD95 (Biolegend, 305611) was added at 1:100 and incubated at 4° C. for 30 min in the dark. Apoptosis was detected by flow cytometry analysis of the expression of the apoptosis marker molecule CD95 (indicated as MFI). Curves were fitted using GraphPad Prism 6.0 and EC50 was calculated. The results are shown in FIG. 9, that NK003 promoted apoptosis of Raji with a EC50 of 2.6 nM (FIG. 9A); and NK003 promoted apoptosis of Ramos cells with an EC50 of 3 nM (FIG. 9B).

Example 6. Primary T Cell Activity Assay 6.1 DC Cell Activation

Human Peripheral Blood Mononuclear Cells (PBMCs) were used to determine NK003's ability to activate dendritic cells (DCs). The isolation of DC cells is a conventional method, and is specifically as follows: PBMCs (Hemacare, PB 009C-3) were cultured in RPMI1640 medium containing 10% fetal bovine serum (Lifetechnologies, 10091148) at 37° C. and adherent monocytes were harvested after 6 hours; the supernatant was removed and serum-free RPMI1640 medium containing 100 ng/mL GM-CSF (R & D Systems, 204-IL) and 10 ng/mL IL4 (R & D Systems, 215-GM) was added for culture, at 37° C.; three days later half of the medium was replaced and GM-CSF and IL4 were supplemented to 100 ng/mL and 10 ng/mL; on the sixth day of culture, the suspended cells were collected and move to a new flask, and the same serum-free RPMI1640 medium containing 100 ng/mL GM-CSF and 10 ng/mL IL4 was applied for the further culture of 24 h to obtain DC cells.

On the seventh day, DC cells obtained by the above induction were seeded in 96-well plates in the number of $1\times10^5$/well, and NK003 at different concentrations were added: 0.01 µg/ml, 0.05 µg/ml, 0.1 µg/ml, 0.5 µg/ml, 1 µg/ml, 10 µg/ml and 100 µg/ml. 100 µg/ml HEL was used as a negative control. Goat anti-human Fc was simultaneously added to each group at a concentration of 2.5 µg/ml for cross-linking.

After incubating the above DC cells and antibodies together for 24 h, the mixture was washed with PBS for three times, PE-CD11c (DC cell marker, Biolegend, 117309) and APC-CD86 (DC cell activation marker, Biolegend, 105007) were added at 1:100 and incubated at 4° C. for 30 min in the dark. DC cell activation was detected by flow cytometry and expressed as MFI of APC-CD86. Activation of DC cells can lead to a stronger anti-tumor T cell response. Curves were fitted using GraphPad Prism 6.0 and EC50 was calculated. As shown in FIG. 10, the result is that NK003 can significantly activate human DC cells, and EC50 was 2 nM (FIG. 10A). EC50 was 8 nM (FIG. 10B) after the addition of a cross-linking agent (goat anti-human Fc, anti-Fc), and the intensity of NK003 the activation of DC by NK003 in a cross-linked form was significantly enhanced compared to that by NK003 not in a cross-linked form (MFI was significantly higher).

6.2 B Cell Proliferation

Human Peripheral Blood Mononuclear Cells (PBMCs) were used to determine the ability of NK003 to induce B cell proliferation. CD19⁺ B cells were sorted from human PBMC (Hemacacare, PB009C-3) using the CD19 immunomagnetic bead kit (Miltenyi Biotec, 130-050-301) according to the kit instructions.

The sorted B cells were cultured in RPMI 1640 medium containing 10% fetal bovine serum (Life technologies, 10091148) supplemented with 10 ng/mL IL4. B cells were seeded in 96-well plates at $1\times10^5$/well, and different concentrations of NK003: 0.01 µg/ml, 0.05 µg/ml, 0.1 µg/ml, 0.5 µg/ml, 1 µg/ml, 10 µg/ml and 100 µg/ml were added. HEL at 100 µg/ml was used as a negative control. After incubation at 37° C. for 48 h, the proliferation of the cells was examined using the CellTiter-Glo kit (Promega, G7570) as follows: according to the kit instructions, 70 µl of cells are taken and 100 µl of CellTiter-Glo® Reagent was added, blend it well and leave to set for 10 mins in the dark. The ELISA reader is used for reading the fluorescence intensity, and the higher the intensity is, the more active the cell proliferation is. Curves were fitted using GraphPad Prism 6.0 and EC50 was calculated. As shown in FIG. 11, the result is that NK003 s was able to promote the proliferation of human B cells with an EC50 of 4 nM.

6.3 B Cell Activation

Human Peripheral Blood Mononuclear Cells (PBMCs) were used to determine NK003 the ability of NK003 to activate B cells.

CD19⁺B cells were sorted from human PBMCs using the CD19 immunomagnetic bead kit as shown in 6.2. The B cells obtained by the above sorting were cultured in RPMI 1640 medium containing 10% fetal bovine serum (Lifetechnologies, 10091148). B cells were seeded in 96-well plates at $1\times10^5$/well, and different concentrations of NK003: 0.01 µg/ml, 0.05 µg/ml, 0.1 µg/ml, 0.5 µg/ml, 1 µg/ml, 10 µg/ml and 100 µg/ml were added. HEL at 100 µg/ml was used as a negative control. For crosslinking, goat anti-human Fc was further added to each of the above groups at a concentration of 2.5 µg/ml. After 48 h of co-incubation, PBS was employed to wash for three times, PE-CD86 (B cell activation marker, Biolegend, 105007) was added at 1:100 and incubated at 4° C. for 30 min in the dark. B cell activation after antibody addition (with and without cross-linking) was measured using flow cytometry and expressed as MFI of APC-CD86. Curves were fitted using GraphPad Prism 6.0 and EC50 was calculated. As shown in FIGS. 12A and B, the result is that NK003 could activate human B cells, with an EC50 at 70 nM in case of the absence of a cross-linking agent (goat anti-human Fc, anti-Fc) (FIG. 12A), and an EC50 of 4 nM after the addition of a cross-linking agent (FIG. 12B), and the intensity of activation of B cells by NK003 in a cross-linked form was significantly enhanced compared to that by NK003 not in a cross-linked form (CD86 expression was significantly higher).

Example 7. In Vivo Characterization of Human CD40 Antibody NK003

Different in vivo experiments were performed to further characterize the effect of NK003 human antibody.

7.1 NK003 Inhibits Tumor Growth in SCID Mice

Antibody-dependent cell-mediated cytotoxicity (ADCC) refers to the binding of the Fab segment of the antibody to the epitope of tumor cells, and the binding of Fc segment to FcR on the surface of killer cell (NK cell, macrophage, etc.) mediate the direct killing of target cell by the killer cell. To evaluate NK003-mediated ADCC killing of tumor cells, we used SCID mice to inoculate tumor cells expressing CD40.

Eight male SCID mice which were five weeks old were purchased in Vital River and hbred in SPF grade animal houses. After feeding for a week, the animals were randomly divided into two groups, and was inoculated with Raji cells subcutaneously on the back in an amount of $2.5\times10^6$cell/mouse, four mice per group, and the Day of inoculation was recorded as Day 0. The first group was given NK003 antibody and the second group was given HEL control antibody.

From Day 1, NK003 was intraperitoneally administered at a dose of 7.5 mg/kg once every 7 days for three times in total, and HEL was used as a control antibody, at the same dose and frequency with NK003. The body weight was weighed, and the vertical size of the tumor was measured using a vernier caliper every three days for the mice. The volume of the tumor=(length×width×width)/2. The tumor growth curves were plotted.

The results showed that no significant tumors were seen in NK003 group mice as compared to the control group (FIG. 13A), and the survival rate of mice in NK003 group was 100% (FIG. 13B). NK003 can obviously inhibit the growth of tumors through mediating ADCC effect and improve the survival rate of mice.

7.2 NK003 Activated Immune System in CD40 Humanized Mice

Human CD40 and Fc receptors FcγRIIA, FcγRIIB and FcγRIIIA are inserted into the mouse genome in the genetic background of C57BL/6 to replace the expression of endogenous CD40 and Fc receptors in mice while expressing human CD40 and Fc receptor proteins. The humanized mouse model of CD40 was constructed and supplied by Li Fubin, from Shanghai Jiao Tong University and was bred in the SPF class animal house. OT-1 mice were provided by Li Fubin, Shanghai Jiao Tong University and were bred in SPF-grade animal houses. OT-1 mice were sacrificed by dislocation of cervical vertebrae and spleens were harvested and crushed to collect splenocytes. CD8+ T cells, i.e., OT-1 C8+ T cells, were isolated using the immunomagnetic bead kit (R & D Systems, MAGM 203) according to the kit instructions.

Eight-week-old male CD40-humanized mice, were selected and injected with OT-1 CD8+ T cells by tail vein injection in the amount of 2×10⁶ cells/mouse, and simultaneously injected with 0.1 mg/kg DEC-OVA (Sigma-Aldrich, SAB 4700735) and 5 mg/kg NK003 (the same dose of HEL was used as a control antibody) by intraperitoneal injection. Seven days after the inoculation of cells, the spleens were isolated from sacrifice mice by cervical dislocation. Spleen was ground to obtain single cell suspensions and after lysis to remove red blood cells, staining were carried out using anti-CD4 (ebioscience, RM4-5), anti-CD8 (Biolegend, 53-6.7), anti-CD 45.1 (Biolegend, A20) and anti-TCR-Vα2 (Biolegend, B20.1), and the proliferation of OVA-specific OT-1 C8+ T cells was detected by flow cytometry. The CD45.1+CD8+TCR−Vα2+ subgroup was OT-1CD8+ T cells (OT1 cells). The CD45.1+CD8+ subgroup was CD8 cells, and the CD45.1+CD4+ subgroup was CD4 cells. The results, which were shown in FIG. 14, were that the proportion of OT-1 CD8+ T cells in the NK003 group increased significantly, with the number of cells increasing significantly, and the ratio of CD8 to CD4 increasing correspondingly. NK003 can activate the CD40 humanized mouse immune system.

7.3 NK003 Inhibits Tumor Growth in CD40 Humanized Mice

In order to evaluate the effect of NK003 on activating the immune system and suppressing tumors, we used CD40 humanized mice constructed and provided by Li Fubin of Shanghai Jiaotong University as described in 7.2 to carry the tumor cell MC38 (Basic Medical Cell Center, Institute of Basic Medicine, Chinese Academy of Medical Sciences, 3111C0001CCC000523) inoculation.

The sequences of the positive control anti-CD40 antibody CP870893 used herein come from the U.S. Pat. No. 7,338,660 (see SEQ ID NO: 46 and SEQ ID NO: 48 for light chain and heavy chain sequences therein). The light chain and heavy chains of CP870893 synthesized by GENEWIZ, Inc. were transfected into pFUSE vector, which were transiently co-transfected into 293F suspension cells at a ratio of 1:1 to express the full-length antibody. After 1 week of expression, Superdex™ 200 Increase pre-packed column is used on the AKTA system for purification (the specific steps are the same with those described in Example 4).

Eight-week-old male CD40-humanized mice were subcutaneously inoculated with MC38 cells in the number of 2×10⁶/mouse on the back. When the tumors grew to about 100 mm³, the mice were randomly divided into three groups: 8 mice for the HEL control group, and 5 mice for each of NK003 and CP870893 (Positive control) groups. The antibody was injected intraperitoneally at a dose of 3 mg/kg, once every 3 days for twice in total. The weight of the mice were weighed every three days and measured for the vertical size of the tumor with a vernier caliper. The body weight was weighed, and the vertical size of the tumor was measured using a vernier caliper every three days for the mice. The volume of the tumor=(length×width×width)/2. The tumor growth curve and the mouse body weight curve were plotted. Tumor inhibition rate=(average volume of control group-average volume of experimental group)/average volume of control group×100%.

The results are shown in FIG. 15A, where on the 18th day, the tumor suppression rate of NK003 was 75%, while the tumor suppression rate of CP870893 was only 60%. At the same time, we tested the body weight of the mice. As shown in FIG. 15B, the body weight of the mice using the NK003 antibody did not decrease significantly. Therefore, NK003 can significantly inhibit the growth of tumors and has no significant effect on the body weight of mice.

Example 8. NK003-V12, NK003-S267E/L328F Fc Region Mutants Increased Binding to FcγRIIB and CD40 Agonist Activity To increase binding to FcγR and increase the agonist activity of NK003 antibodies, the Fc region of NK003 (IgG1, EU numbering) was mutated from glutamic acid (E) to aspartate (D) at residue 233, from glycine (G) to aspartate (D) at residue 237, from Histidine (H) to aspartate (D) at residue 268, fro Proline (P) to glycine (G) at residue 271, and from Alanine (A) to arginine (R) at residue 330, resulting in an NK003-V12 variant. The NK003 Fc region (IgG1, EU numbering) was mutated to from Serine (S) to glutamic acid (E) at residue 267 and from Leucine (L) to phenylalanine (F) at residue 328, resulting in the NK003-S267E/L328F variant (see sequence listing). NK003-V12 and NK003-S267E/L328F variant are constructed and then confirmed by sequencing.

TABLE 3

NK003 Fc region mutation site summary

| variant | Amino acid substitution | | | | |
|---|---|---|---|---|---|
| NK003-V12 | E233D | G237D | H268D | P271G | A330R |
| NK003-S267E/L328F | S267E | | | L328F | |

To evaluate the agonist activity of the NK003-V12 and NK003-S267E/L328F variants, the light and heavy chains of the NK003-V12 and NK003-S267E/L328F variants synthesized by GENEWIZ, Inc. were transfected into pFUSE vectors which is transiently co-transfected at 1:1 into 293F suspension cells. Full-length antibodies were expressed, and after 1 week of expression, Superdex™ 200 Increase pre-packed column is used on the AKTA system for purification (the specific steps are the same with those described in Example 4).

The GENEWIZ, Inc. synthesized FcγRIIA (NCBI, NM-001136219.1) and FcγRIIb (NCBI, NM-004001.4) CDS region were cloned into pCDH vector, transiently transfected into 293FT cells with PEI using standard procedures. The medium was replaced 6 h after the transfection, and continuous culture in a DMEM medium containing 10% fetal bovine serum (Biological Industries, 04-001-1A) at 37° C., and after 48 h of expression, FcγRIIA-expressing cells and FcγRIIb-expressing 293FT cells were obtained, respectively.

2×10⁵ cells/tube of 293FT-FcγRIIA or 293FT-FcγRIIB cells as described above were taken, and 2×10⁵ cells/tube of NF-κB-GFP+hCD40 reporter cells were further added to each tube (as described in Example 1). Different concentrations of NK003, NK003-V12 and NK003-S267E/L328F diluted in PBS were added to each tube: 0.01 μg/ml, 0.05 μg/ml, 0.1 μg/ml, 0.5 μg/ml, 1 μg/ml, 5 μg/ml and 10 μg/ml, and 10 μg/ml HEL were used as a negative control. After coculture at 37° C. for 24 hours, washing was carried out with PBS for three times, and analysis by flow cytometry was applied to detect the MFI of GFP. The results are shown in FIG. 16. Compared to wild-type NK003, NK003-V12, NK003-S267E/L328F have significantly enhanced agonist activity.

Example 9 Affinity Maturation of the Humanized CD40 Antibody NK003

Mutation libraries were constructed separately for the NK003 VH, VL complementarity determining regions and the framework region, which is inserted in the Fab format (FIG. 17) into the pcomb3 phage vector (Biovector inc. 108925), and NK003 optimization was accomplished using the phage affinity maturation method.

9.1 Affinity Maturation for NK003 VH, VL Complementarity Determining Region CDR3

9.1.1 Construction of the Mutation Libraries of NK003 VH and VL Complementarity Determining Region CDR3

The light chain VL and CL fragments were amplified using the primer pairs VL1/VL2 and CL1/CL2, respectively, using NK003 light chain DNA (SEQ ID NO:72) with a stop codon inserted in CDR3 as a template. The reaction conditions are as follows: 2 min at 95° C., 1 cycle; 95° C. for 30 s, 65° C. for 30 s, 72° C. for 10 s, 35 cycles; 5 min at 72° C., 1 cycle. PCR fragments of interest were recovered using a recovery kit from TIANGEN BIOTECH (BEIJING) CO., LTD. The primers are as follows:

```
VL1:
5'-GCGGCCGAGCTCGATGTTGTGATGACTCAG-3'

VL2:
5'-GGTCCCCTGGCCAAA AGT GTA CGG AGT

TCA TAG ACC TTG CAT
```

GCAGTAATAAAG-3' (randomly any two sites of the underlined regions are mutated to MNN, synthesized by GENEWIZ, Inc. in high throughput)

```
CL1:
5'-TTTGGCCAGGGGACCAAGCTGGAGATC-3'

CL2:
5'-TATCTAGATTAATTAAATCACTCTCCCCTGTTGAAGCTC-3'
```

By performing overlap PCR amplification of the above-mentioned two parts of PCR products, an NK003 light chain mutation library was obtained. The reaction conditions are as follows: 2 min at 95° C., 1 cycle; 95° C. for 30 s, 65° C. for 30 s, 72° C. for 20 s, 8 cycles; adding VL1/CL2 primers, 30 s at 95° C., 30 s at 65° C., 20 s at 72° C., 27 cycles; 5 min at 72° C., 1 cycle. The NK003 light chain mutant library and pcomb3 vector were double-digested with SacI (NEB, R3156L) and PacI (NEB, R0547L), respectively, and the PCR target fragment was recovered using a recovery kit from TIANGEN BIOTECH (BEIJING) CO., LTD. The mutant library gene and the vector were ligated at 25° C. for 3 h with T4 ligase (NEB, M0202L) in a molar ratio of 3:1. The ligation products were electrotransformed into XL1-Blue electrotransferase competent cells, and a library of $5 \times 10^5$ light chain mutations, named pcomb3-NK003-LCDR3, was constructed.

Heavy chain VH and CH1 fragments were amplified using the primer pairs VH1/VH2 and CH1-1/CH1-2, respectively, using NK003 heavy chain DNA (SEQ ID NO:73) with a stop codon inserted in CDR3 as a template. The reaction conditions are as follows: 2 min at 95° C., 1 cycle; 95° C. for 30 s, 65° C. for 30 s, 72° C. for 10 s, 35 cycles; 5 min at 72° C., 1 cycle. The primers are as follows:

```
VH1:
5'-TGCAGCTGCTCGAGCAGGTACAGCTGGTGCAGTC-3'

VH2:
5'-CTTTGCCCCAGACGTC CAT GTA GTA GTA GTA GGT

TCA AGT AGC TCC CAC TCT TTC TCTCGCACAG-3'
```

(randomly any two sites of the underlined regions are mutated to MNN, synthesized by GENEWIZ, Inc. in high throughput)

```
CH1-1:
5'-GACGTCTGGGGCAAAGGGACCACGGTC-3'

CH1-2:
5'-GCCTGGCCACTAGTTTTGTCAACTTTCTTGTCC-3'
```

By performing overlap PCR amplification of the above-mentioned two parts of PCR products, an NK003 heavy chain mutation library was obtained, wherein the reaction conditions are as follows: 2 min at 95° C., 1 cycle; 95° C. for 30 s, 65° C. for 30 s, 72° C. for 20 s, 8 cycles; adding VH1/CH1-2 primer, 30 s at 95° C., 30 s at 65° C., 20 s at 72° C., 27 cycles; 5 min at 72° C., 1 cycle. The NK003 heavy chain mutant library, pcomb3-NK003-LCDR3 vector were double digested with SpeI (NEB, R3133L) and XhoI (NEB, R0146L), respectively, and PCR target fragments were recovered using a recovery kit from TIANGEN BIOTECH (BEIJING) CO., LTD. The mutant library gene and the vector are ligated for 3 h at a molar ratio of 3:1 by T4 ligase at 25° C. The ligation products were electrotransformed into XL1-Blue electrotransferase competent cells, and a light-heavy chain double-mutation library with a library capacity of $2.4 \times 10^7$, named pcomb3-NK003-AM, was constructed.

9.1.2 Phage Mutant Antibody Library Screening

The pcomb3-NK003-AM antibody library was used to screen for antibodies that bind to CD40. The specific method was as described in Example 2. The screening results are shown in Table 1.

TABLE 12

Screening of the pcomb3-NK003-AM antibody library for CD40 binding antibodies using phage display technology

| | | First round | Second round | Third round |
|---|---|---|---|---|
| CD40 | The starting number | $7.2 \times 10^{11}$ | $8 \times 10^{11}$ | $8 \times 10^{11}$ |
| | The acquisition number | $1.28 \times 10^8$ | $1.3 \times 10^7$ | $4.9 \times 10^6$ |
| | Antigen concentration | 20 nM | 2 nM | 0.2 nM |

To preliminarily evaluate the positive rate of screened for CD40-binding antibodies, we picked 32 phage single clones from the third round for phage ELISA analysis. Specific methods for phage ELISA are described in Example 2. Positive clones were defined as the binding signal to CD40 being more than three times the binding signal to BSA control. The results are shown in FIG. 18, and the positive rate of the third round of screening is 96.8%.

The phage eluted in the third round was infected with XL1-blue and then spread on a plate. After blending by scraper, NK003-AM plasmid was extracted by plasmid mini-extracting kit from TIANGEN BIOTECH (BEIJING) CO., LTD. A target fragment of about 1500 bp is recovered after double enzyme digestion by using SacI and SpeI, and sent to TIANGEN BIOTECH (BEIJING) CO., LTD for third-generation sequencing. The sequencing results are shown in FIG. 19. According to the results of the third generation sequencing the heavy chain DNA and light chain DNA of the screened antibodies NK003-AM-9 and NK003-AM-18 were synthesized (GENEWIZ, Inc.), and are cloned into a vector pFUSE, respectively, and the specific methods for purification and expression are shown in Example 4. The NK003-AM-9 and NK003-AM-18 VH/VL sequences are seen in Tables 6 to 8 of the sequence list.

9.1.3 NK003 CDR3 Affinity Maturation Activity Identification

In this example, flow cytometry was used to detect the activation of NF-κB-GFP+hCD40 reporter cell lines by NK003-AM-9 and NK003-AM-18 antibodies, the specific steps were as follows:

$3 \times 10^5$ cells/tube NF-κB-GFP+hCD40 report cells as obtained in Example 1 were taken respectively, and NK003-AM-9, NK003-AM-18 and NK003 at the following different concentrations: 0.01 μg/ml, 0.05 μg/ml, 0.1 μg/ml, 0.5 μg/and 1 μg/ml were further added, respectively. For crosslinking, a secondary antibody, goat anti-human Fc (southern Biotech, SBA-2048-01) was added to each group at a concentration of 2.5 μg/ml simultaneously. After coculture in RPMI 1640 medium (Life technologies, C11875500 CP) containing 10% fetal bovine serum (Biological Industries, 04-001-1A) at 37° C. for 24 h, the mixture was washed with PBS three times and analyzed using flow cytometry. The data obtained were fitted to curves using GraphPad Prism 6.0 and EC50 was calculated. As shown in FIG. 20, The results are that the NK003-AM-9 and NK003-AM-18 activate the NF-kB-GFP+hCD40 reporter cell line in a cross-linked form. The EC50 is 0.25 nM and 0.3 nM respectively, and the activities of the two antibodies are similar and are improved by nearly 10 times as compared with the wild type NK003.

9.2 Affinity Maturation for NK003 VH, VL Framework Region 9.2.1 Construction of NK003 VH, VL Framework Region Mutation Library The light chain VL region was amplified by nested PCR using NK003 light chain DNA (SEQ ID NO:74) as a template and using random mutation PCR kit (Agilent Technologies, 200550) and primer pairs VL1/VL2, VL3/VL4 under reaction conditions: 2 min at 95° C., 1 cycle; 30 s at 95° C., 30 s at 65° C., 30 s at 72° C., 28 cycle; 10 min at 72° C., 1 cycle. The light chain CL region was amplified using the NK003 light chain DNA (SEQ ID NO:11) as a template and using the primer pair CL1/CL2, reaction conditions: 2 min at 95° C., 1 cycle; 95° C. for 30 s, 65° C. for 30 s, 72° C. for 30 s, 30 cycles; 5 min at 72° C., 1 cycle. Target PCR fragments were recovered using a recovery kit of TIANGEN BIOTECH (BEIJING) CO., LTD. The primers are as follows:

```
VL1:
5'-CTATCGCGATTGCAGTGGCACTGGCTG-3'

VL2:
5'-CCAGATTTCAACTGCTCATCAGATGGC-3'

VL3:
5'-CTACCGTGGCCCAGGCGGCCGAGCTC-3'

VL4:
5'-GAAGACAGATGGTGCAGCCACAGTTCG-3'
```

-continued
```
CL1:
5'-CGAACTGTGGCTGCACCATCTGTCTTC-3'

CL2:
5'-TATCTAGATTAATTAAATCACTCTCCCCTGTTGAAGCTC-3'
```

Performing overlap PCR amplification of the above VL and CL PCR products obtained an NK003 light chain mutation library. The reaction conditions are as follows: 2 min at 95° C., 1 cycle; 95° C. for 30 s, 65° C. for 30 s, 72° C. for 40 s, 8 cycles; adding VL3/CL2 primers, 30 s at 95° C., 30 s at 65° C., 40 s at 72° C., 27 cycles; 10 min at 72° C., 1 cycle. The NK003 light chain mutant library and the pcomb3 vector were subjected to double digestion with SacI and PacI, respectively, and the PCR target fragment was recovered using a recovery kit of TIANGEN BIOTECH (BEIJING) CO., LTD. The mutant library genes and the vector are ligated for 3 h at a molar ratio of 3:1 by T4 ligase at 25° C. The ligation products were electrotransformed into XL1-Blue electrotransferase competent cells, and a light chain mutation library with a library capacity of $1 \times 10^5$, named pcomb3-NK003-VL, was constructed. The heavy chain VH domain was amplified by nested PCR using NK003 heavy chain DNA (SEQ ID NO:75) as a template, using the primer pairs VH1/VH2, VH3/VH4, under reaction condition 3: 2 min at 95° C., 1 cycle; 30 s at 95° C., 30 s at 65° C., 30 s at 72° C., 28 cycles; 10 min at 72° C., 1 cycle. The heavy chain CH1 region was amplified using the NK003 heavy chain DNA (SEQ ID NO:12) as a template using the primer pair CH1-1/CH1-2, under reaction conditions: 2 min at 95° C., 1 cycle; 30 s at 95° C., 30 s at 65° C., 30 s at 72° C., 32 cycles; 10 min at 72° C., 1 cycle. PCR fragments of interest were recovered using a recovery kit of TIANGEN BIOTECH (BEIJING) CO., LTD. The primers are as follows:

```
VH1:
5'-GCCGCTGGATTGTTATTACTCGCTGC-3'

VH2:
5'-CAGAGGTGCTCTTGGAGGAGGGTGCC-3'

VH3:
5'-GCCATGGCCGAGGTGCAGCTGCTCGAG-3'

VH4:
5'-GAAGACCGATGGGCCCTTGGTGGAGGC-3'

CH1-1:
5'-GCCTCCACCAAGGGCCCATCGGTCTTC-3'

CH1-2:
5'-GCCTGGCCACTAGTTTTGTCAACTTTCTTGTCC-3'
```

The VH and CH1 PCR products were subjected to overlap PCR amplification to obtain the NK003 heavy chain mutation library. The reaction conditions are as follows: 2 min at 95° C., 1 cycle; 95° C. for 30 s, 65° C. for 30 s, 72° C. for 40 s, 8 cycles; adding VH3/CH1-2 primer, 95° C. 30 s, 65° C. 30 s, 72° C. 40 s, 27 cycles; 10 min at 72° C., 1 cycle. Double enzyme digestion on the NK003 heavy chain mutant library and the pcomb3-NK003-VL vector were performed by using SpeI and XhoI respectively, and target PCR fragments were recovered using a recovery kit of TIANGEN BIOTECH (BEIJING) CO., LTD. The mutant library gene and the vector are ligated for 3 h at a molar ratio of 3:1 by T4 ligase at 25° C. The ligation products were electrotransformed into XL1-Blue electrotransforming competent cells. A light-heavy chain double mutation library with a library capacity of $2.4 \times 10^7$, named pcomb3-NK003-EP, was constructed.

9.2.2 Phage Mutant Antibody Library Screening

The pcomb3-NK003-EP antibody library was used to screen for antibodies that bind to CD40. The specific method was as described in Example 2. The screening results are shown in Table 2.

TABLE 13

Screening of the pcomb3-NK003-EP antibody library for CD40 binding antibodies using phage display technology

|  |  | First round | Second round | Third round |
|---|---|---|---|---|
| CD40 | The starting number | $7 \times 10^{11}$ | $7.6 \times 10^{11}$ | $5.9 \times 10^{11}$ |
|  | The acquisition number | $3.7 \times 10^7$ | $1.1 \times 10^7$ | $4.3 \times 10^6$ |
|  | Antigen concentration | 20 nM of light | 10 nM | 2 nM |

The phage eluted in the third round was infected with XL1-blue and then spread on a plate. After blending by scraper, NK003-EP plasmid was extracted by plasmid mini-extracting kit ofrom TIANGEN BIOTECH (BEIJING) CO., LTD. A target fragment of about 1500 bp is recovered by double enzyme digestion by using SacI and SpeI, and sent to GENEWIZ, Inc. for third-generation sequencing. The sequencing results are shown in FIG. 21. According to the results of the third-generation sequencing, the antibody NK003-AM-18-EP1 heavy chain DNA was synthesized (GENEWIZ, Inc.) and cloned into the vector pFUSE. Plasmids containing the NK003-AM-18 light chain and NK003-AM-18-EP1 heavy chain, respectively, were transiently co-transfected into 293F suspension cells at 1:1 to express the full-length NK003-AM-18-EP1 antibody. The specific method for purification and expression is shown in Example 4. The VH sequence of NK003-AM-18-EP1 is shown in sequence table 6 of the sequence list.

9.2.3 Identification of Affinity Maturation Activity for NK003 Framework Region In this example, the activation of the NF-κB-GFP+hCD40 reporter cell line by the NK003-AM-18-EP1 antibody was detected by flow cytometry using the following specific steps:

$3 \times 10^5$ cells/tube NF-κB-GFP+hCD40 reporter cells as obtained in Example 1 were taken respectively, and NK003-AM-18, NK003-AM-18-EP1 and NK003 at different concentrations: 0.0075 nM, 0.025 nM, 0.075 nM, 0.25 nM, 0.75 nM, 2.5 nM and 7.5 nM were further added respectively. For cross-linking, a secondary antibody, goat anti-human Fc, was added to each group at a concentration of 2.5 μg/ml simultaneously. After coculture in RPMI 1640 medium (Life technologies, C11875500 CP) containing 10% fetal bovine serum (Biological Industries, 04-001-1A) at 37° C. for 24 h, the mixture was washed with PBS three times and analyzed using flow cytometry. The data obtained were fitted to curves using GraphPad Prism 6.0 and EC50 was calculated. As shown in FIG. 22, the result is that NK003-AM-18-EP1 activated the NF-κB-GFP+hCD40 reporter cell line in a cross-linked form with EC50 at 0.35 nM, which was similar to NK003-AM-18 activity.

TABLE 4

Sequences:
Sequences of FR and CDR of the heavy chain variable domain (VH) (or heavy chain variable region HCVR) of the exemplary antibody of the present invention (CDR sequences are defined by IMGT rules)

| Numbering of Antibody | VH FR1 | VH CDR1 | VH FR2 | VH CDR2 | VH FR3 | VH CDR3 | VH FR4 |
|---|---|---|---|---|---|---|---|
| NK003 | QVQLVQSGAEVKKPGASVKVSCKAS (SEQ ID NO: 23) | GYTFTGYY (SEQ ID NO: 1) | MHWVRQAPGQGLEWMGW (SEQ ID NO: 25) | INPNSGGT (SEQ ID NO: 3) | NYAQKFQGRVTMTRDTSISTAYMELSRLRSDDTAVYYC (SEQ ID NO: 27) | ARERVGATPTYYYMDV (SEQ ID NO: 5) | WGKGTTVTVSS (SEQ ID NO: 29) |
| NK003-AM-9 | SEQ ID NO: 23 | SEQ ID NO: 1 | SEQ ID NO: 25 | SEQ ID NO: 3 | SEQ ID NO: 27 | ARERVGATPTYYYWDV (SEQ ID NO: 51) | SEQ ID NO: 29 |
| NK003-AM-18 | SEQ ID NO: 23 | SEQ ID NO: 1 | SEQ ID NO: 25 | SEQ ID NO: 3 | SEQ ID NO: 27 | ARERVGANPTYYYWDV (SEQ ID NO: 52) | SEQ ID NO: 29 |
| NK003-AM-18-EP | SEQ ID NO: 23 | SEQ ID NO: 1 | MYWVRQAPGQGLEWMGW (SEQ ID NO: 76) | SEQ ID NO: 3 | SEQ ID NO: 27 | SEQ ID NO: 52 | SEQ ID NO: 29 |
| common sequence | SEQ ID NO: 23 | SEQ ID NO: 1 | SEQ ID NO: 25 | SEQ ID NO: 3 | SEQ ID NO: 27 | ARERVGAX1PTYYYX2X3DV (SEQ ID NO: 55) | SEQ ID NO: 29 |
| NK004 | QVQLVESGGGLVQPGRSLRISCAGS (SEQ ID NO: 2) | GFTFGDSA (SEQ ID NO: 2) | MHWVRQAPGKGLEWVSG (SEQ ID NO: 26) | ISRNSDTI (SEQ ID NO: 4) | VYADSVKGRFTISRDNAKNSLYLQMNSLRAEDTALY | ARRSGDHHAMDV (SEQ ID NO: 6) | WGPGTTVTVSS (SEQ ID NO: 30) |

TABLE 4-continued

Sequences:
Sequences of FR and CDR of the heavy chain variable domain (VH) (or heavy chain variable region HCVR) of the exemplary antibody of the present invention (CDR sequences are defined by IMGT rules)

| Numbering of Antibody | VH FR1 | VH CDR1 | VH FR2 | VH CDR2 | VH FR3 | VH CDR3 | VH FR4 |
|---|---|---|---|---|---|---|---|
| | NO: 24) | | | | | YC (SEQ ID NO: 28) | |

TABLE 5

The FR and CDR sequences of the light chain variable domain (VL) (or light chain variable region LCVR) of the exemplary antibody of the present invention (CDR sequences are defined by IMGT rules)

| Numbering of Antibody | VL FR1 | VL CDR1 | VL FR2 | VL CDR2 | VL FR3 | VL CDR3 | VL FR4 |
|---|---|---|---|---|---|---|---|
| NK003 | DVVMTQSPLSLPVTPGESATISCRSS (SEQ ID NO: 31) | QSLLYSNGYNYQLLIY (SEQ ID NO: 7) | LDWYLLKPGQSP (SEQ ID NO: 9) | LGS (SEQ ID NO: 33) | NRASGVPDRFSGSGSGTDFTLKISRVEAEDVGLYYC (SEQ ID NO: 35) | MQGLETPYT (SEQ ID NO: 11) | FGQGTKLEIK (SEQ ID NO: 37) |
| NK003-AM-9 | SEQ ID NO: 31 | SEQ ID NO: 7 | SEQ ID NO: 33 | SEQ ID NO: 9 | SEQ ID NO: 35 | MNGLEVPYT (SEQ ID NO: 53) | SEQ ID NO: 37 |
| NK003-AM-18/ NK003-AM-18-EP | SEQ ID NO: 31 | SEQ ID NO: 7 | SEQ ID NO: 33 | SEQ ID NO: 9 | SEQ ID NO: 35 | MQQLEQPYT (SEQ ID NO: 54) | SEQ ID NO: 37 |
| common sequence | SEQ ID NO: 31 | SEQ ID NO: 7 | SEQ ID NO: 33 | SEQ ID NO: 9 | SEQ ID NO: 35 | MX1X2LX3X4PYT (SEQ ID NO: 56) | SEQ ID NO: 37 |
| NK004 | ETTLTQSPATLSLSPGERATLSCRAS (SEQ ID NO: 34) | QSVNTY (SEQ ID NO: 8) | LAWYQQKPGQAPRLLMY (SEQ ID NO: 10) | DSS (SEQ ID NO: ) | SRATGIPDRFSGSGSGTDFTLTISRLEPEDFAVYYC (SEQ ID NO: ) | QQYSTVPLT (SEQ ID NO: 12) | FGGGTKLEIK (SEQ ID NO: 38) |

TABLE 5-continued

The FR and CDR sequences of the light chain variable domain (VL) (or light chain variable region LCVR) of the exemplary antibody of the present invention (CDR sequences are defined by IMGT rules)

| Numbering of Antibody | VL FR1 | VL CDR1 | VL FR2 | VL CDR2 | VL FR3 | VL CDR3 | VL FR4 |
|---|---|---|---|---|---|---|---|
| | NO: 32) | | | | | | (SEQ ID NO: 36) |

TABLE 6

DNA and amino acid sequences of the heavy chain variable domain (VH) (or heavy chain variable region HCVR) of the exemplary antibody of the present invention

| Numbering of Antibody | VH DNA sequence | VH amino acid sequence |
|---|---|---|
| NK003 | SEQ ID NO: 39 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARERVGATPTYYYYMDVWGKGTTVTVSS (SEQ ID NO: 13) |
| NK003-AM-9 | SEQ ID NO: 57 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARERVGATPTYYYWDVWGKGTTVTVSS (SEQ ID NO: 58) |
| NK003-AM-18 | SEQ ID NO: 59 | QVQLVQSGAEVKKPGASVKVSCKASGYTFTGYYMHWVRQAPGQGLEWMGWINPNSGGTNYAQKFQGRVTMTRDTSISTAYMELSRLRSDDTAVYYCARERVGANPTYYYYWDVWGKGTTVTVSS (SEQ ID NO: 60) |
| NK003-AM-18-EP1 | SEQ ID NO: 61 | QVQLVQSGAEVKKPGASVKVSCKASGYTFTGYYMYWVRQAPGQGLEWMGWINPNSGGTNYAQKFQGRVTMTRDTSISTAYMELSRLRSDDTAVYYCARERVGANPTYYYYWDVWGKGTTVTVSS (SEQ ID NO: 62) |
| NK004 | SEQ ID NO: 40 | QVQLVESGGGLVQPGRSLRISCAGSGFTFGDSAMHWVRQAPGKGLEWVSGISRNSDTIVY |

TABLE 6-continued

DNA and amino acid sequences of the heavy chain variable domain (VH) (or heavy chain variable region HCVR) of the exemplary antibody of the present invention

| Numbering of Antibody | VH DNA sequence | VH amino acid sequence |
|---|---|---|
| | | ADSVKGRFTISRDNA KNSLYLQMNSLRAED TALYYCARRSGDHHA MDVWGPGTTVTVSS (SEQ ID NO: 14) |

TABLE 7

DNA and amino acid sequences of the light chain variable domain (VL) (or light chain variable region LCVR) of the exemplary antibody of the present invention

| Numbering of Antibody | VL DNA sequence | VL amino acid sequence |
|---|---|---|
| NK003 | SEQ ID NO: 41 | DVVMTQSPLSLPVTPGESAT ISCRSSQSLLYSNGYNYLDW YLLKPGQSPQLLIYLGSNRA SGVPDRFSGSGSGTDFTLKI SRVEAEDVGLYYCMQGLETP YTFGQGTKLEIK (SEQ ID NO: 15) |
| NK003-AM-9 | SEQ ID NO: 63 | DVVMTQSPLSLPVTPGESAT ISCRSSQSLLYSNGYNYLDW YLLKPGQSPQLLIYLGSNRA SGVPDRFSGSGSGTDFTLKI SRVEAEDVGLYYCMNGLEVP YTFGQGTKLEIK (SEQ ID NO: 64) |
| NK003-AM-18/ NK003-AM-18-EP1 | SEQ ID NO: 65 | DVVMTQSPLSLPVTPGESAT ISCRSSQSLLYSNGYNYLDW YLLKPGQSPQLLIYLGSNRA SGVPDRFSGSGSGTDFTLKI SRVEAEDVGLYYCMQQLEQP YTFGQGTKLEIK (SEQ ID NO: 66) |
| NK004 | SEQ ID NO: 42 | ETTLTQSPATLSLSPGERAT LSCRASQSVNTYLAWYQQKP GQAPRLLMYDSSSRATGIPD RFSGSGSGTDFTLTISRLEP EDFAVYYCQQYSTVPLTFGG GTKLEIK (SEQ ID NO: 16) |

TABLE 8

Heavy and light chain sequences of exemplary antibodies of the invention

| Numbering of Antibody | IgG form | amino acid sequence of heavy chain | amino acid sequence of light chain |
|---|---|---|---|
| NK003 | IgG1 | SEQ ID NO: 17 | SEQ ID NO: 21 |
| NK003-V12 | IgG1mutant | SEQ ID NO: 18 | |
| NK003-S267E/ L328F | IgG1mutant | SEQ ID NO: 19 | |
| NK003-AM-9 | IgG1 | SEQ ID NO: 67 | SEQ ID NO: 68 |
| NK003-AM-18 | IgG1 | SEQ ID NO: 69 | SEQ ID NO: 71 |
| NK003-AM-18-EP1 | IgG1 | SEQ ID NO: 70 | |
| NK004 | IgG1 | SEQ ID NO: 20 | SEQ ID NO: 22 |

TABLE 9

Exemplary signal peptide DNA and amino acid sequences of the present invention

| DNA sequence of signal peptide | Amino acid sequence of signal peptide |
|---|---|
| ATGTACAGGATGCAACTCCTGTCTTGC ATTGCACTAAGTCTTGCACTTGTCACG AATTCG (SEQ ID NO: 44) | MYRMQLLSCIALSLALVTNS (SEQ ID NO: 43) |

TABLE 10

Amino acid and DNA sequences of the control antibody HEL of the present invention

| Numbering of Antibody | IgG form | Amino acid sequence of heavy chain | Amino acid sequence of light chain |
|---|---|---|---|
| HEL | IgG1 | SEQ ID NO: 45 | SEQ ID NO: 46 |

| Numbering of Antibody | IgG form | DNA sequence of heavy chain | DNA sequence of light chain |
|---|---|---|---|
| HEL | IgG1 | SEQ ID NO: 47 | SEQ ID NO: 48 |

TABLE 11

Amino acid and DNA sequence of the control antibody N27 of the present invention

| Numbering of Antibody | amino acid sequence |
|---|---|
| N27 | SEQ ID NO: 49 |

| Numbering of Antibody | DNA sequence |
|---|---|
| N27 | SEQ ID NO: 50 |

The invention claimed is:

1. An antibody or antigen-binding fragment thereof that binds to CD40, comprising
   (i) a heavy chain variable (VH) region comprising the 3 complementarity determining regions (CDRs) HCDR1, HCDR2 and HCDR3 of the heavy chain variable region as set forth in SEQ ID NO:13, 58, 60 or 62 and a light chain variable (VL) region comprising the 3 CDRs LCDR1, LCDR2 and LCDR3 of the light chain variable region as set forth in SEQ ID NO:15, 64 or 66;
   (ii) a VH region comprising the 3 CDRs HCDR1, HCDR2 and HCDR3 of the heavy chain variable region as set forth in SEQ ID NO: 13 and a VL comprising the 3 CDRs LCDR1, LCDR2 and LCDR3 of the light chain variable region as set forth in SEQ ID NO: 15;
   (iii) a VH region comprising the 3 CDRs HCDR1, HCDR2 and HCDR3 of the heavy chain variable region as set forth as SEQ ID NO: 58 and a VL region comprising the 3 CDRs LCDR1, LCDR2 and LCDR3 of the light chain variable region as set forth as SEQ ID NO: 64;
   (iv) a VH region comprising the 3 CDRs HCDR1, HCDR2 and HCDR3 of the heavy chain variable region as set forth as SEQ ID NO:60 or 62 and a VL region comprising the 3 CDRs LCDR1, LCDR2 and LCDR3 of the light chain variable region as set forth as SEQ ID NO:66; or
   (v) a VH region comprising the 3 CDRs HCDR1, HCDR2 and HCDR3 of the heavy chain variable region as set forth in SEQ ID NO: 14 and a VL region comprising the 3 CDRs LCDR1, LCDR2 and LCDR3 of the light chain variable region as set forth in SEQ ID NO: 16.

2. An antibody or antigen-binding fragment thereof that binds to CD40, comprising
   (i) a VH region comprising HCDR1, HCDR2 and HCDR3 comprising the amino acid sequences of SEQ ID NO:1, 3 and 5, respectively;
   (ii) a VH region comprising HCDR1, HCDR2 and HCDR3 comprising the amino acid sequences of SEQ ID NO:1, 3 and 51, respectively; or
   (iii) a VH region comprising HCDR1, HCDR2 and HCDR3 comprising the amino acid sequences of SEQ ID NO:1, 3 and 52, respectively
and
   (i) a VL region comprising LCDR1, LCDR2 and LCDR3 comprising the amino acid sequences of SEQ ID NO:7, 9 and 11, respectively;
   (ii) a VL region comprising LCDR1, LCDR2 and LCDR3 comprising the amino acid sequences of SEQ ID NO:7, 9 and 53, respectively; or
   (iii) a VL region comprising LCDR1, LCDR2 and LCDR3 comprising the amino acid sequences of SEQ ID NO:7, 9 and 54, respectively.

3. The antibody or antigen-binding fragment thereof of claim 1, wherein,
   (a) the VH region
      (i) comprises an amino acid sequence having at least 90%, 91%, 92%, 93%, 94%, 95%, 96%, 97%, 98% or 99% identity with an amino acid sequence selected from the group consisting of SEQ ID NO:13, 58, 60, 62, and 14;
      (ii) comprises an amino acid sequence selected from the group consisting of SEQ ID NO:13, 58, 60, 62, and 14; or
      iii) comprises an amino acid sequence having 1 or more amino acid alterations as compared to an amino acid sequence selected from the group consisting of SEQ ID NOs:13, 58, 60, 62, and 14;
   and/or
   (b) the VL region
      (i) comprises an amino acid sequence having at least 90%, 91%, 92%, 93%, 94%, 95%, 96%, 97%, 98% or 99% identity with an amino acid sequence selected from the group consisting of SEQ ID NO:15, 64, 66, and 16;
      (ii) comprises an amino acid sequence selected from the group consisting of SEQ ID NO:15, 64, 66, and 16; or
      (iii) comprises an amino acid sequence having 1 or more amino acid alterations as compared to an amino acid sequence selected from the group consisting of SEQ ID NO:15, 64, 66, and 16.

4. The antibody or antigen-binding fragment thereof of claim 3, wherein
   (i) the VH region comprises the amino acid sequence of SEQ ID NO: 13, 58, 60 or 62 and the VL region comprises an amino acid sequence selected from SEQ ID NO: 15, 64 or 66;

(ii) the VH region comprises the amino acid sequence of SEQ ID NO: 13 and the VL region comprises the amino acid sequence of SEQ ID NO: 15;

(iii) the VH region comprises the amino acid sequence of SEQ ID NO:58 and the VL region comprises the amino acid sequence of SEQ ID NO:64;

(iv) the VH region comprises the amino acid sequence of SEQ ID NO: 60 and the VL region comprises the amino acid sequence of SEQ ID NO: 66;

(v) the VH region comprises the amino acid sequence of SEQ ID NO:62 and the VL region comprises the amino acid sequence of SEQ ID NO:66; or (vi) the VH region comprises the amino acid sequence of SEQ ID NO: 14 and the VL region comprises the amino acid sequence of SEQ ID NO: 16.

5. The antibody or antigen-binding fragment thereof of claim 1, comprising a heavy chain and/or a light chain, wherein (a) the heavy chain
  (i) comprises an amino acid sequence having at least 85%, 90%, 91%, 92%, 93%, 94%, 95%, 96%, 97%, 98% or 99% identity with an amino acid sequence selected from the group consisting of SEQ ID NO:17, 18, 19, 67, 69, 70, and 20;
  (ii) comprises an amino acid sequence selected from the group consisting of SEQ ID NO:17, 18, 19, 67, 69, 70, and 20; or
  (iii) comprises an amino acid sequence having 1 or more amino acid alterations as compared to an amino acid sequence selected from the group consisting of SEQ ID NOs:17, 18, 19, 67, 69, 70, and 20;

and/or (b) the light chain
  (i) comprises an amino acid sequence having at least 85%, 90%, 91%, 92%, 93%, 94%, 95%, 96%, 97%, 98% or 99% identity with an amino acid sequence selected from the group consisting of SEQ ID NO:21, 68, 71, and 22;
  (ii) comprises an amino acid sequence selected from the group consisting of SEQ ID NO:21, 68, 71, and 22; or
  (iii) comprises an amino acid sequence having 1 or more amino acid alterations as compared to an amino acid sequence selected from the group consisting of SEQ ID NOs: 21, 68, 71, and 22.

6. The antibody or antigen-binding fragment thereof of claim 5, wherein (i) the heavy chain comprises an amino acid sequence selected from the group consisting of SEQ ID NO:17, 18, 19, 67, 69, and 70 and the light chain comprises an amino acid sequence selected from the group consisting of SEQ ID NO:21, 68, and 71, (ii) the heavy chain comprises an amino acid sequence selected from the group consisting of SEQ ID NO:17, 18, and 19 and the light chain comprises the amino acid sequence of SEQ ID NO:21;

(iii) the heavy chain comprises the amino acid sequence of SEQ ID NO:67 and the light chain comprises the amino acid sequence of SEQ ID NO:68;

(iv) the heavy chain comprises the amino acid sequence selected from SEQ ID NO:69 or 70 and the light chain comprises the amino acid sequence of SEQ ID NO:71; or (v) the heavy chain comprises the amino acid sequence of SEQ ID NO: 20 and the light chain comprises the amino acid sequence of SEQ ID NO: 22.

7. The antibody or antigen-binding fragment thereof of claim 1, wherein the antibody is a monoclonal antibody.

8. The antibody or antigen-binding fragment thereof of claim 1, wherein the antibody is a humanized antibody or a human antibody or a chimeric antibody.

9. An isolated nucleic acid encoding the antibody or antigen-binding fragment thereof of claim 1.

10. A vector comprising the nucleic acid of claim 9.

11. A host cell comprising the vector of claim 10.

12. A method of preparing an antibody or antigen-binding fragment thereof that binds CD40, the method comprising culturing a host cell comprising a nucleic acid encoding the antibody or antigen-binding fragment thereof of claim 1, under conditions suitable for expression of the antibody or antigen-binding fragment thereof, and the method further comprising recovering the antibody or antigen-binding fragment thereof from the host cell.

13. An immunoconjugate comprising the antibody or antigen-binding fragment thereof of claim 1 and an additional agent.

14. A pharmaceutical composition comprising the antibody or antigen-binding fragment thereof of claim 1 and a pharmaceutical excipient.

15. The pharmaceutical composition of claim 14, further comprising one or more additional therapeutic agents.

16. The pharmaceutical composition of claim 15, wherein said therapeutic agent is selected from a chemotherapeutic agent, other antibody, cytotoxic agent, vaccine, anti-infective active agent, small molecule drug, or immunomodulatory agent.

17. A detecting kit comprising the antibody or antigen-binding fragment thereof of claim 1.

* * * * *

SEQUENCE LISTING

```
<160> NUMBER OF SEQ ID NOS: 76

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1
```

```
Gly Tyr Thr Phe Thr Gly Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Gly Phe Thr Phe Gly Asp Ser Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Ile Asn Pro Asn Ser Gly Gly Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Ile Ser Arg Asn Ser Asp Thr Ile
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Construct

<400> SEQUENCE: 5

Ala Arg Glu Arg Val Gly Ala Thr Pro Thr Tyr Tyr Tyr Tyr Met Asp
1               5                   10                  15

Val

<210> SEQ ID NO 6
<211> LENGTH: 12
<212> TYPE: PRT
<213> ORGANISM: Artificial Sequence
<220> FEATURE:
<223> OTHER INFORMATION: Synthetic Construct

<400> SEQUENCE: 6

Ala Arg Arg Ser Gly Asp His His Ala Met Asp Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7
```

```
Gln Ser Leu Leu Tyr Ser Asn Gly Tyr Asn Tyr
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic Construct

<400> SEQUENCE: 8

Gln Ser Val Asn Thr Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: Synthetic Construct

<400> SEQUENCE: 9

Leu Gly Ser
1

<210> SEQ ID NO 10
<211> LENGTH: 3
<212> TYPE: PRT
<213> ORGANISM: Artificial Sequence
<220> FEATURE:
<223> OTHER INFORMATION: Synthetic Construct

<400> SEQUENCE: 10

Asp Ser Ser
1

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Met Gln Gly Leu Glu Thr Pro Tyr Thr
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Gln Tyr Ser Thr Val Pro Leu Thr
1               5

<210> SEQ ID NO 13
<211> LENGTH: 124
<212> TYPE: PRT
<213> ORGANISM: Artificial Sequence
<220> FEATURE:
<223> OTHER INFORMATION: Synthetic Construct

<400> SEQUENCE: 13
```

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Arg Val Gly Ala Thr Pro Thr Tyr Tyr Tyr Met Asp
        100                 105                 110

Val Trp Gly Lys Gly Thr Thr Val Thr Val Ser Ser
        115                 120

<210> SEQ ID NO 14
<211> LENGTH: 119
<212> TYPE: PRT
<213> ORGANISM: Artificial Sequence
<220> FEATURE:
<223> OTHER INFORMATION: Synthetic Construct

<400> SEQUENCE: 14

Gln Val Gln Leu Val Glu Ser Gly Gly Gly Leu Val Gln Pro Gly Arg
1               5                   10                  15

Ser Leu Arg Ile Ser Cys Ala Gly Ser Gly Phe Thr Phe Gly Asp Ser
            20                  25                  30

Ala Met His Trp Val Arg Gln Ala Pro Gly Lys Gly Leu Glu Trp Val
        35                  40                  45

Ser Gly Ile Ser Arg Asn Ser Asp Thr Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
            85                  90                  95

Ala Arg Arg Ser Gly Asp His His Ala Met Asp Val Trp Gly Pro Gly
        100                 105                 110

Thr Thr Val Thr Val Ser Ser
        115

<210> SEQ ID NO 15
<211> LENGTH: 112
<212> TYPE: PRT
<213> ORGANISM: Artificial Sequence
<220> FEATURE:
<223> OTHER INFORMATION: Synthetic Construct

<400> SEQUENCE: 15

Asp Val Val Met Thr Gln Ser Pro Leu Ser Leu Pro Val Thr Pro Gly
1               5                   10                  15

Glu Ser Ala Thr Ile Ser Cys Arg Ser Ser Gln Ser Leu Leu Tyr Ser
            20                  25                  30

Asn Gly Tyr Asn Tyr Leu Asp Trp Tyr Leu Leu Lys Pro Gly Gln Ser
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Leu Tyr Tyr Cys Met Gln Gly
                 85                  90                  95

Leu Glu Thr Pro Tyr Thr Phe Gly Gln Gly Thr Lys Leu Glu Ile Lys
            100                 105                 110
```

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

```
Glu Thr Thr Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Thr Tyr
                20                  25                  30

Leu Ala Trp Tyr Gln Gln Lys Pro Gly Gln Ala Pro Arg Leu Leu Met
            35                  40                  45

Tyr Asp Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Ser Thr Val Pro Leu
                 85                  90                  95

Thr Phe Gly Gly Gly Thr Lys Leu Glu Ile Lys
            100                 105
```

<210> SEQ ID NO 17
<211> LENGTH: 454
<212> TYPE: PRT
<213> ORGANISM: Artificial Sequence
<220> FEATURE:
<223> OTHER INFORMATION: Synthetic Construct

<400> SEQUENCE: 17

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Arg Val Gly Ala Thr Pro Thr Tyr Tyr Tyr Met Asp
            100                 105                 110

Val Trp Gly Lys Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
        130                 135                 140

Gly Thr Ala Ala Leu Gly Cys Leu Val Lys Asp Tyr Phe Pro Glu Pro
```

```
            145                 150                 155                 160
Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
                180                 185                 190

Val Thr Val Pro Ser Ser Ser Leu Gly Thr Gln Thr Tyr Ile Cys Asn
                195                 200                 205

Val Asn His Lys Pro Ser Asn Thr Lys Val Asp Lys Lys Val Glu Pro
            210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr Asn
        290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
                340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
                420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 18
<211> LENGTH: 454
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
```

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Glu Arg Val Gly Ala Thr Pro Thr Tyr Tyr Tyr Met Asp
            100                 105                 110

Val Trp Gly Lys Gly Thr Thr Val Thr Val Ser Ser Ala Ser Thr Lys
            115                 120                 125

Gly Pro Ser Val Phe Pro Leu Ala Pro Ser Ser Lys Ser Thr Ser Gly
            130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
            195                 200                 205

Val Asn His Lys Pro Ser Asn Thr Lys Val Asp Lys Val Glu Pro
210                 215                 220

Lys Ser Cys Asp Lys Thr His Thr Cys Pro Pro Cys Pro Ala Pro Asp
225                 230                 235                 240

Leu Leu Gly Asp Asp Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Asp Glu Asp Gly Glu Val Lys Phe Asn Trp Tyr Val Asp Gly
            275                 280                 285

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Arg Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 19

<211> LENGTH: 454
<212> TYPE: PRT
<213> ORGANISM: Artificial Sequence
<220> FEATURE:
<223> OTHER INFORMATION: Synthetic Construct

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Val Gly Ala Thr Pro Thr Tyr Tyr Tyr Tyr Met Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Glu His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Phe Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
            450

<210> SEQ ID NO 20
<211> LENGTH: 449
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Val Glu Ser Gly Gly Gly Leu Val Gln Pro Gly Arg
1               5                   10                  15

Ser Leu Arg Ile Ser Cys Ala Gly Ser Gly Phe Thr Phe Gly Asp Ser
            20                  25                  30

Ala Met His Trp Val Arg Gln Ala Pro Gly Lys Gly Leu Glu Trp Val
        35                  40                  45

Ser Gly Ile Ser Arg Asn Ser Asp Thr Ile Val Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Arg Ser Gly Asp His His Ala Met Asp Val Trp Gly Pro Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 21
<211> LENGTH: 219
<212> TYPE: PRT
<213> ORGANISM: Artificial Sequence
<220> FEATURE:
<223> OTHER INFORMATION: Synthetic Construct

<400> SEQUENCE: 21

Asp Val Val Met Thr Gln Ser Pro Leu Ser Leu Pro Val Thr Pro Gly
1               5                   10                  15

Glu Ser Ala Thr Ile Ser Cys Arg Ser Ser Gln Ser Leu Leu Tyr Ser
                20                  25                  30

Asn Gly Tyr Asn Tyr Leu Asp Trp Tyr Leu Leu Lys Pro Gly Gln Ser
                35                  40                  45

Pro Gln Leu Leu Ile Tyr Leu Gly Ser Asn Arg Ala Ser Gly Val Pro
            50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Gly
                85                  90                  95

Leu Glu Thr Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Thr Tyr
            20                  25                  30

Leu Ala Trp Tyr Gln Gln Lys Pro Gly Gln Ala Pro Arg Leu Leu Met
        35                  40                  45

Tyr Asp Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ser Thr Val Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 24
<211> LENGTH: 25
<212> TYPE: PRT
<213> ORGANISM: Artificial Sequence

```
<220> FEATURE:
<223> OTHER INFORMATION: Synthetic Construct

<400> SEQUENCE: 24

Gln Val Gln Leu Val Glu Ser Gly Gly Gly Leu Val Gln Pro Gly Arg
1               5                   10                  15

Ser Leu Arg Ile Ser Cys Ala Gly Ser
            20                  25

<210> SEQ ID NO 25
<211> LENGTH: 17
<212> TYPE: PRT
<213> ORGANISM: Artificial Sequence
<220> FEATURE:
<223> OTHER INFORMATION: Synthetic Construct

<400> SEQUENCE: 25

Met His Trp Val Arg Gln Ala Pro Gly Gln Gly Leu Glu Trp Met Gly
1               5                   10                  15

Trp

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Met His Trp Val Arg Gln Ala Pro Gly Lys Gly Leu Glu Trp Val Ser
1               5                   10                  15

Gly

<210> SEQ ID NO 27
<211> LENGTH: 38
<212> TYPE: PRT
<213> ORGANISM: Artificial Sequence
<220> FEATURE:
<223> OTHER INFORMATION: Synthetic Construct

<400> SEQUENCE: 27

Asn Tyr Ala Gln Lys Phe Gln Gly Arg Val Thr Met Thr Arg Asp Thr
1               5                   10                  15

Ser Ile Ser Thr Ala Tyr Met Glu Leu Ser Arg Leu Arg Ser Asp Asp
            20                  25                  30

Thr Ala Val Tyr Tyr Cys
        35

<210> SEQ ID NO 28
<211> LENGTH: 38
<212> TYPE: PRT
<213> ORGANISM: Artificial Sequence
<220> FEATURE:
<223> OTHER INFORMATION: Synthetic Construct

<400> SEQUENCE: 28

Val Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Leu Tyr Tyr Cys
        35
```

```
<210> SEQ ID NO 29
<211> LENGTH: 11
<212> TYPE: PRT
<213> ORGANISM: Artificial Sequence
<220> FEATURE:
<223> OTHER INFORMATION: Synthetic Construct

<400> SEQUENCE: 29

Trp Gly Lys Gly Thr Thr Val Thr Val Ser Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Trp Gly Pro Gly Thr Thr Val Thr Val Ser Ser
1               5                   10

<210> SEQ ID NO 31
<211> LENGTH: 26
<212> TYPE: PRT
<213> ORGANISM: Artificial Sequence
<220> FEATURE:
<223> OTHER INFORMATION: Synthetic Construct

<400> SEQUENCE: 31

Asp Val Val Met Thr Gln Ser Pro Leu Ser Leu Pro Val Thr Pro Gly
1               5                   10                  15

Glu Ser Ala Thr Ile Ser Cys Arg Ser Ser
            20                  25

<210> SEQ ID NO 32
<211> LENGTH: 26
<212> TYPE: PRT
<213> ORGANISM: Artificial Sequence
<220> FEATURE:
<223> OTHER INFORMATION: Synthetic Construct

<400> SEQUENCE: 32

Glu Thr Thr Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 33
<211> LENGTH: 17
<212> TYPE: PRT
<213> ORGANISM: Artificial Sequence
<220> FEATURE:
<223> OTHER INFORMATION: Synthetic Construct

<400> SEQUENCE: 33

Leu Asp Trp Tyr Leu Leu Lys Pro Gly Gln Ser Pro Gln Leu Leu Ile
1               5                   10                  15

Tyr

<210> SEQ ID NO 34
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 34

Leu Ala Trp Tyr Gln Gln Lys Pro Gly Gln Ala Pro Arg Leu Leu Met
1               5                   10                  15
Tyr

<210> SEQ ID NO 35
<211> LENGTH: 36
<212> TYPE: PRT
<213> ORGANISM: Artificial Sequence
<220> FEATURE:
<223> OTHER INFORMATION: Synthetic Construct

<400> SEQUENCE: 35

Asn Arg Ala Ser Gly Val Pro Asp Arg Phe Ser Gly Ser Gly Ser Gly
1               5                   10                  15
Thr Asp Phe Thr Leu Lys Ile Ser Arg Val Glu Ala Glu Asp Val Gly
            20                  25                  30
Leu Tyr Tyr Cys
        35

<210> SEQ ID NO 36
<211> LENGTH: 36
<212> TYPE: PRT
<213> ORGANISM: Artificial Sequence
<220> FEATURE:
<223> OTHER INFORMATION: Synthetic Construct

<400> SEQUENCE: 36

Ser Arg Ala Thr Gly Ile Pro Asp Arg Phe Ser Gly Ser Gly Ser Gly
1               5                   10                  15
Thr Asp Phe Thr Leu Thr Ile Ser Arg Leu Glu Pro Glu Asp Phe Ala
            20                  25                  30
Val Tyr Tyr Cys
        35

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Phe Gly Gln Gly Thr Lys Leu Glu Ile Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Phe Gly Gly Gly Thr Lys Leu Glu Ile Lys
1               5                   10

<210> SEQ ID NO 39
<211> LENGTH: 372
<212> TYPE: DNA
<213> ORGANISM: Artificial Sequence
<220> FEATURE:

<223> OTHER INFORMATION: Synthetic Construct

<400> SEQUENCE: 39

```
caggtacagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag ggcttgagtg gatgggatgg atcaaccctc acagtggtgg cacaaactat   180
gcacagaagt tcagggcag ggtcaccatg accaggaca cgtccatcag cacagcctac    240
atggagctga gcaggctgag atctgacgac acggccgtgt attactgtgc gagagaaaga   300
gtgggagcta ctccgaccta ctactactac atggacgtct ggggcaaagg gaccacggtc   360
accgtctcct ca                                                       372
```

<210> SEQ ID NO 40
<211> LENGTH: 357
<212> TYPE: DNA
<213> ORGANISM: Artificial Sequence
<220> FEATURE:
<223> OTHER INFORMATION: Synthetic Construct

<400> SEQUENCE: 40

```
caggtgcagc tggtggagtc tgggggggc ttggtacagc ctggcaggtc cctgagaata    60
tcctgtgcag gctctggatt cacctttggc gattcggcca tgcactgggt ccggcaagct   120
ccaggtaagg gcctggagtg gtctcaggt attagtagga atagtgatac catagtctat    180
gcggactctg tgaagggccg attcaccatc tccagagaca acgccaagaa ctccctgtat   240
ctgcaaatga acagtctgag agctgaggac acggccttgt attactgtgc aaggcggtcg   300
ggtgatcacc acgctatgga cgtctggggc cagggaccac ggtcaccgt ctcctca      357
```

<210> SEQ ID NO 41
<211> LENGTH: 336
<212> TYPE: DNA
<213> ORGANISM: Artificial Sequence
<220> FEATURE:
<223> OTHER INFORMATION: Synthetic Construct

<400> SEQUENCE: 41

```
gatgttgtga tgactcagtc tccactctcc ctgcccgtca cccctggaga gtcggccacc    60
atctcctgca ggtctagtca gagcctcctg tacagtaatg gatacaacta tttggattgg   120
tacctgctga agccagggca gtctccacaa ctcctgatct atttgggttc taatcgggcc   180
tccggggtcc ctgacaggtt cagtggcagt ggatcaggca cagattttac actgaagatc   240
agcagagtgg aggctgagga tgttggcctt tattactgca tgcaaggtct agaaactccg   300
tacacttttg gccagggac caagctggag atcaaa                              336
```

<210> SEQ ID NO 42
<211> LENGTH: 324
<212> TYPE: DNA
<213> ORGANISM: Artificial Sequence
<220> FEATURE:
<223> OTHER INFORMATION: Synthetic Construct

<400> SEQUENCE: 42

```
gaaacgacac tcacgcagtc tccagccacc ctgtctttgt ctccagggga aagagccacc    60
ctctcctgca gggccagtca gagtgttaac acttatttag cctggtacca acagaaacct   120
ggccaggctc ccaggctcct catgtatgat tcatccagca gggccactgg catcccagac   180
aggttcagtg gcagtgggtc tgggacagac ttcactctca ccatcagcag actggagcct   240
```

```
gaagattttg cagtgtatta ctgtcagcag tatagtaccg taccgctcac tttcggcgga    300
gggaccaagc tggagatcaa acgt                                           324
```

<210> SEQ ID NO 43
<211> LENGTH: 20
<212> TYPE: PRT
<213> ORGANISM: Artificial Sequence
<220> FEATURE:
<223> OTHER INFORMATION: Synthetic Construct

<400> SEQUENCE: 43

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 44
<211> LENGTH: 60
<212> TYPE: DNA
<213> ORGANISM: Artificial Sequence
<220> FEATURE:
<223> OTHER INFORMATION: Synthetic Construct

<400> SEQUENCE: 44

```
atgtacagga tgcaactcct gtcttgcatt gcactaagtc ttgcacttgt cacgaattcg    60
```

<210> SEQ ID NO 45
<211> LENGTH: 464
<212> TYPE: PRT
<213> ORGANISM: Artificial Sequence
<220> FEATURE:
<223> OTHER INFORMATION: Synthetic Construct

<400> SEQUENCE: 45

```
Met Met Val Leu Ser Leu Leu Tyr Leu Leu Thr Ala Leu Pro Gly Ile
1               5                   10                  15

Leu Ser Glu Val Gln Leu Glu Gln Ser Gly Ala Glu Leu Met Lys Pro
            20                  25                  30

Gly Ala Ser Val Lys Ile Ser Cys Lys Ala Thr Gly Tyr Thr Phe Thr
        35                  40                  45

Thr Tyr Trp Ile Glu Trp Ile Lys Gln Arg Pro Gly His Ser Leu Glu
    50                  55                  60

Trp Ile Gly Glu Ile Leu Pro Gly Ser Asp Ser Thr Tyr Tyr Asn Glu
65                  70                  75                  80

Lys Val Lys Gly Lys Val Thr Phe Thr Ala Asp Ala Ser Ser Asn Thr
                85                  90                  95

Ala Tyr Met Gln Leu Ser Ser Leu Thr Ser Glu Asp Ser Ala Val Tyr
            100                 105                 110

Tyr Cys Ala Arg Gly Asp Gly Phe Tyr Val Tyr Trp Gly Gln Gly Thr
        115                 120                 125

Thr Leu Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190
```

```
Ser Ser Gly Leu Tyr Ser Leu Ser Val Val Thr Val Pro Ser Ser
            195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
                260                 265                 270

Thr Pro Glu Val Thr Cys Val Val Val Asp Val Ser His Glu Asp Pro
            275                 280                 285

Glu Val Lys Phe Asn Trp Tyr Val Asp Gly Val Glu Val His Asn Ala
        290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
                340                 345                 350

Ile Ser Lys Ala Lys Gly Gln Pro Arg Glu Pro Gln Val Tyr Thr Leu
            355                 360                 365

Pro Pro Ser Arg Asp Glu Leu Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
        450                 455                 460

<210> SEQ ID NO 46
<211> LENGTH: 234
<212> TYPE: PRT
<213> ORGANISM: Artificial Sequence
<220> FEATURE:
<223> OTHER INFORMATION: Synthetic Construct

<400> SEQUENCE: 46

Met Asp Ser Gln Ala Gln Val Leu Met Leu Leu Leu Leu Trp Val Ser
1               5                   10                  15

Gly Thr Cys Gly Asp Ile Glu Leu Thr Gln Ser Pro Ala Thr Leu Ser
            20                  25                  30

Val Thr Pro Gly Asp Ser Val Ser Leu Ser Cys Arg Ala Ser Gln Ser
        35                  40                  45

Ile Ser Asn Asn Leu His Trp Tyr Gln Gln Lys Ser His Glu Ser Pro
    50                  55                  60

Arg Leu Leu Ile Lys Tyr Thr Ser Gln Ser Met Ser Gly Ile Pro Ser
65                  70                  75                  80

Arg Phe Ser Gly Ser Gly Ser Gly Thr Asp Phe Thr Leu Ser Ile Asn
                85                  90                  95
```

Ser Val Glu Thr Glu Asp Phe Gly Val Tyr Phe Cys Gln Gln Ser Gly
            100                 105                 110

Ser Trp Pro Arg Thr Phe Gly Gly Thr Lys Leu Asp Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 47
<211> LENGTH: 1392
<212> TYPE: DNA
<213> ORGANISM: Artificial Sequence
<220> FEATURE:
<223> OTHER INFORMATION: Synthetic Construct

<400> SEQUENCE: 47

```
atgatggtcc tgagcctgct gtatctgctg actgcactgc ctggaatcct gagcgaggtc      60
cagctggaac agagcggggc tgaactgatg aaacccggag caagtgtgaa aatctcctgc     120
aaggccacag gctacacttt caccacatat tggatcgagt ggattaagca gcgaccagga     180
cacagcctgg agtggatcgg cgaaattctg cctgggtcag acagcaccta ctataacgaa     240
aaggtgaaag gcaaggtcac ttttaccgcc gatgctagct ccaataccgc ttacatgcag     300
ctgtctagtc tgacatccga ggactctgcc gtctactatt gtgccagggg ggatgggttt     360
tatgtgtatt gggggcaggg caccactctg accgtgtcct cagcctccac taagggccca     420
tccgtgttcc ctctggcacc ctccagcaag agcacaagcg gaggcaccgc cgcactgggc     480
tgcctcgtga aggactactt cccagaaccc gtgaccgtca gctggaatag cggcgctctg     540
accagcggag tccacacttt ccccgcagtg ctgcagtcca gcggcctgta cagcctgagc     600
agcgtggtca ctgtgccaag cagcagcctg ggcactcaga cctacatctg caacgtcaac     660
cacaagccca gcaacacaaa ggtggacaag aaggtcgagc ccaagtcctg cgataagacc     720
cacacctgcc ctccatgtcc cgcccccgag ctgctgggag acccagcgt cttcctgttt     780 cccccaagc caaggacac cctgatgatc agcaggaccc ccgaagtgac ctgcgtcgtg     840
gtggacgtga gccacgaaga tcccgaggtg aagttcaact ggtacgtgga cggcgtggaa     900
gtgcacaacg ccaagacaaa acccagggag gagcagtatg ccagcaccta cagggtcgtg     960
agcgtcctga ccgtgctgca ccaagactgg ctgaacggca aggagtataa gtgcaaggtg    1020
agcaacaagg cactgcccgc ccccatcgag aagaccattt ccaaggccaa ggggcaacct    1080
agggagccac aggtctacac tctgccccct agcagggacg agctgaccaa gaaccaggtc    1140
tccctgactt gcctggtgaa ggggttttat cccagcgaca tcgccgtcga gtgggagagc    1200
aatggccagc ccgaaaacaa ctacaagacc acacccctg tgctggacag cgacggcagc    1260
```

-continued

```
ttctttctgt atagcaaact gacagtggat aagagcagat ggcagcaggg caacgtgttc    1320
tcctgctccg tgatgcacga ggccctgcac aatcactaca cccagaagtc cctgagcctg    1380
tcccccggaa aa                                                        1392
```

<210> SEQ ID NO 48
<211> LENGTH: 702
<212> TYPE: DNA
<213> ORGANISM: Artificial Sequence
<220> FEATURE:
<223> OTHER INFORMATION: Synthetic Construct

<400> SEQUENCE: 48

```
atggatagcc aggcccaggt gctgatgctg ctgctgctgt gggtgtccgg aacttgcggc     60
gatattgaac tgacccagag ccctgccact ctgtccgtga ccccaggcga cagcgtctcc    120
ctgtcttgca gggccagtca gtcaatcagc aacaatctgc actggtacca gcagaagtct    180
catgagagtc cccggctgct gatcaaatat acatcccagt ctatgagtgg cattcctagc    240
agattctcag gcagcgggtc cggaaccgac tttacactgt ctattaacag cgtggagacc    300
gaagatttcg gggtctactt ttgtcagcag agcgggtcat ggcctcggac attcggcggg    360
gggactaaac tggacatcaa acgaaccgtg gccgcaccaa gcgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagctttaac agaggcgagt gc                       702
```

<210> SEQ ID NO 49
<211> LENGTH: 472
<212> TYPE: PRT
<213> ORGANISM: Artificial Sequence
<220> FEATURE:
<223> OTHER INFORMATION: Synthetic Construct

<400> SEQUENCE: 49

```
Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Tyr Met His Trp Val Arg Gln Ala Pro Gly Gln Gly Leu Glu
        35                  40                  45

Trp Met Gly Gly Ile Ile Pro Ile Phe Gly Thr Gly Asn Tyr Ala Gln
    50                  55                  60

Lys Phe Gln Gly Arg Val Thr Ile Thr Ala Asp Glu Ser Thr Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Glu Glu Glu Gln Gln Phe Ser Leu Asp Tyr Trp Gly
            100                 105                 110

Gln Gly Thr Leu Val Thr Val Ser Ser Gly Gly Gly Gly Leu Ser
            115                 120                 125

Asn Phe Met Leu Thr Gln Pro His Ser Val Ser Glu Ser Pro Gly Lys
        130                 135                 140

Thr Val Thr Ile Ser Cys Thr Arg Ser Ser Gly Ser Ile Ala Ser Asn
145                 150                 155                 160
```

Ser Val His Trp Tyr Gln Gln Arg Pro Gly Ser Ala Pro Thr Thr Val
            165                 170                 175

Ile Ser Glu Asn Asn Gln Arg Pro Ser Gly Val Pro Asp Arg Phe Ser
            180                 185                 190

Gly Ser Ile Asp Ser Ser Asn Ser Ala Ser Leu Thr Ile Ser Gly
            195                 200                 205

Leu Lys Thr Glu Asp Glu Ala Asp Tyr Tyr Cys Gln Ser Tyr Asp Ser
210                 215                 220

Asn Phe His Trp Val Phe Gly Gly Gly Thr Gln Leu Thr Val Leu Gly
225                 230                 235                 240

Gly Leu Gly Gly Leu Asp Lys Thr His Thr Cys Pro Pro Cys Pro Ala
            245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
            275                 280                 285

Val Asp Val Ser His Glu Asp Pro Glu Val Lys Phe Asn Trp Tyr Val
            290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
            325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
            355                 360                 365

Arg Glu Pro Gln Val Tyr Thr Leu Pro Pro Ser Arg Asp Glu Leu Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
            405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
450                 455                 460

Ser Leu Ser Leu Ser Pro Gly Lys
465                 470

```
<210> SEQ ID NO 50
<211> LENGTH: 1416
<212> TYPE: DNA
<213> ORGANISM: Artificial Sequence
<220> FEATURE:
<223> OTHER INFORMATION: Synthetic Construct

<400> SEQUENCE: 50
atggcacagg ttcagctggt acagtctggg gctgaggtga agaagcctgg ggcctcagtg      60
aaggtctcct gcaaggcttc tggatacacc ttcaccagct actatatgca ctgggtgcga     120 caggccctg acaagggct tgagtggatg gagggatca tccctatctt tggtacagga      180
aactacgcac agaagttcca gggcagagtc acgattaccg cggacgaatc cacgagcaca     240
```

```
gcctacatgg agctgagcag cctgagatct gaggacacgg ccgtgtatta ctgtgcgaga    300
gaggaggagc agcagttcag cttggactac tggggccagg gaaccctggt caccgtctcc    360
tcaggcggcg gcggtggctt atccaatttt atgctgactc agccccactc tgtgtcggag    420
tctccgggga agacggttac catctcctgc acccgcagca gtggcagcat tgccagcaac    480
tctgtgcatt ggtaccagca gcgcccgggc agtgccccca ccactgtgat ctctgaaaat    540
aaccaacgac cctctggggt ccctgatcgg ttctctggct ccatcgacag ctcctccaac    600
tctgcctccc tcaccatctc tggactgaag actgaggacg aggctgacta ctactgtcag    660
tcttatgaca gcaactttca ttgggtgttc ggcggaggga cccagctcac cgttttaggt    720
ggcctcgggg gcctggacaa aactcacaca tgcccaccgt gcccagcacc tgaactcctg    780
gggggaccgt cagtcttcct cttcccccca aaacccaagg acaccctcat gatctcccgg    840 accccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgtgt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaagggcca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaa                             1416
```

<210> SEQ ID NO 51
<211> LENGTH: 17
<212> TYPE: PRT
<213> ORGANISM: Artificial Sequence
<220> FEATURE:
<223> OTHER INFORMATION: Synthetic Construct

<400> SEQUENCE: 51

Ala Arg Glu Arg Val Gly Ala Thr Pro Thr Tyr Tyr Tyr Trp Trp Asp
1               5                   10                  15

Val

<210> SEQ ID NO 52
<211> LENGTH: 17
<212> TYPE: PRT
<213> ORGANISM: Artificial Sequence
<220> FEATURE:
<223> OTHER INFORMATION: Synthetic Construct

<400> SEQUENCE: 52

Ala Arg Glu Arg Val Gly Ala Asn Pro Thr Tyr Tyr Tyr Trp Trp Asp
1               5                   10                  15

Val

<210> SEQ ID NO 53
<211> LENGTH: 9
<212> TYPE: PRT
<213> ORGANISM: Artificial Sequence
<220> FEATURE:
<223> OTHER INFORMATION: Synthetic Construct

<400> SEQUENCE: 53

```
Met Asn Gly Leu Glu Val Pro Tyr Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Construct

<400> SEQUENCE: 54

Met Gln Gln Leu Glu Gln Pro Tyr Thr
1               5

<210> SEQ ID NO 55
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (14)..(15)
<223> OTHER INFORMATION: Xaa can be any naturally occurring amino acid

<400> SEQUENCE: 55

Ala Arg Glu Arg Val Gly Ala Xaa Pro Thr Tyr Tyr Tyr Xaa Xaa Asp
1               5                   10                  15
Val

<210> SEQ ID NO 56
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 56

Met Xaa Xaa Leu Xaa Xaa Pro Tyr Thr
1               5

<210> SEQ ID NO 57
<211> LENGTH: 372
<212> TYPE: DNA
<213> ORGANISM: Artificial Sequence
<220> FEATURE:
<223> OTHER INFORMATION: Synthetic Construct

<400> SEQUENCE: 57
caggtacagc tggtgcagtc tggggctgag gtgaagaagc ctggggcctc agtgaaggtc      60
tcctgcaagg cttctggata caccttcacc ggctactata tgcactgggt gcgacaggcc     120
cctggacaag gcttgagtg gatgggatgg atcaaccctaa acagtggtgg cacaaactat     180
gcacagaagt tcagggcag ggtcaccatg accagggaca cgtccatcag cacagcctac     240
```

```
atggagctga gcaggctgag atctgacgac acggccgtgt attactgtgc gagagaaaga    300
gtgggagcta ctccgaccta ctactactgg tgggacgtct ggggcaaagg gaccacggtc    360
accgtctcct ca                                                        372
```

<210> SEQ ID NO 58
<211> LENGTH: 124
<212> TYPE: PRT
<213> ORGANISM: Artificial Sequence
<220> FEATURE:
<223> OTHER INFORMATION: Synthetic Construct

<400> SEQUENCE: 58

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Val Gly Ala Thr Pro Thr Tyr Tyr Tyr Trp Trp Asp
            100                 105                 110

Val Trp Gly Lys Gly Thr Thr Val Thr Val Ser Ser
        115                 120
```

<210> SEQ ID NO 59
<211> LENGTH: 372
<212> TYPE: DNA
<213> ORGANISM: Artificial Sequence
<220> FEATURE:
<223> OTHER INFORMATION: Synthetic Construct

<400> SEQUENCE: 59

```
caggtacagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaacccta acagtggtgg cacaaactat    180
gcacagaagt tcagggcag ggtcaccatg accagggaca cgtccatcag cacagcctac    240
atggagctga gcaggctgag atctgacgac acggccgtgt attactgtgc gagagaaaga    300
gtgggagcta atccgaccta ctactactac tgggacgtct ggggcaaagg gaccacggtc    360
accgtctcct ca                                                        372
```

<210> SEQ ID NO 60
<211> LENGTH: 124
<212> TYPE: PRT
<213> ORGANISM: Artificial Sequence
<220> FEATURE:
<223> OTHER INFORMATION: Synthetic Construct

<400> SEQUENCE: 60

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30
```

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Val Gly Ala Asn Pro Thr Tyr Tyr Tyr Tyr Trp Asp
            100                 105                 110

Val Trp Gly Lys Gly Thr Thr Val Thr Val Ser Ser
            115                 120

<210> SEQ ID NO 61
<211> LENGTH: 372
<212> TYPE: DNA
<213> ORGANISM: Artificial Sequence
<220> FEATURE:
<223> OTHER INFORMATION: Synthetic Construct

<400> SEQUENCE: 61
caggtacagc tggtgcagtc tggggctgag gtgaagaagc ctggggcctc agtgaaggtc      60
tcctgcaagg cttctggata caccttcacc ggctactata tgtactgggt gcgacaggcc     120
cctggacaag ggcttgagtg gatgggatgg atcaacccta cagtggtgg cacaaactat     180 gcacagaagt tcagggcag ggtcaccatg accagggaca cgtccatcag cacagcctac     240
atggagctga gcaggctgag atctgacgac acggccgtgt attactgtgc gagagaaaga     300
gtgggagcta atccgaccta ctactactac tgggacgtct ggggcaaagg gaccacggtc     360
accgtctcct ca                                                          372

<210> SEQ ID NO 62
<211> LENGTH: 124
<212> TYPE: PRT
<213> ORGANISM: Artificial Sequence
<220> FEATURE:
<223> OTHER INFORMATION: Synthetic Construct

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Tyr Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Val Gly Ala Asn Pro Thr Tyr Tyr Tyr Tyr Trp Asp
            100                 105                 110

Val Trp Gly Lys Gly Thr Thr Val Thr Val Ser Ser
            115                 120

<210> SEQ ID NO 63

<211> LENGTH: 336
<212> TYPE: DNA
<213> ORGANISM: Artificial Sequence
<220> FEATURE:
<223> OTHER INFORMATION: Synthetic Construct

<400> SEQUENCE: 63

```
gatgttgtga tgactcagtc tccactctcc ctgcccgtca cccctggaga gtcggccacc      60
atctcctgca ggtctagtca gagcctcctg tacagtaatg gatacaacta tttggattgg     120
tacctgctga agccagggca gtctccacaa ctcctgatct atttgggttc taatcgggcc     180
tccggggtcc ctgacaggtt cagtggcagt ggatcaggca cagattttac actgaagatc     240
agcagagtgg aggctgagga tgttggcctt tattactgca tgaatggtct agaagtgccg     300
tacacttttg gccaggggac caagctggag atcaaa                               336
```

<210> SEQ ID NO 64
<211> LENGTH: 112
<212> TYPE: PRT
<213> ORGANISM: Artificial Sequence
<220> FEATURE:
<223> OTHER INFORMATION: Synthetic Construct

<400> SEQUENCE: 64

```
Asp Val Val Met Thr Gln Ser Pro Leu Ser Leu Pro Val Thr Pro Gly
1               5                   10                  15
Glu Ser Ala Thr Ile Ser Cys Arg Ser Ser Gln Ser Leu Leu Tyr Ser
            20                  25                  30
Asn Gly Tyr Asn Tyr Leu Asp Trp Tyr Leu Leu Lys Pro Gly Gln Ser
        35                  40                  45
Pro Gln Leu Leu Ile Tyr Leu Gly Ser Asn Arg Ala Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Leu Tyr Tyr Cys Met Asn Gly
                85                  90                  95
Leu Glu Val Pro Tyr Thr Phe Gly Gln Gly Thr Lys Leu Glu Ile Lys
            100                 105                 110
```

<210> SEQ ID NO 65
<211> LENGTH: 336
<212> TYPE: DNA
<213> ORGANISM: Artificial Sequence
<220> FEATURE:
<223> OTHER INFORMATION: Synthetic Construct

<400> SEQUENCE: 65

```
gatgttgtga tgactcagtc tccactctcc ctgcccgtca cccctggaga gtcggccacc      60
atctcctgca ggtctagtca gagcctcctg tacagtaatg gatacaacta tttggattgg     120
tacctgctga agccagggca gtctccacaa ctcctgatct atttgggttc taatcgggcc     180
tccggggtcc ctgacaggtt cagtggcagt ggatcaggca cagattttac actgaagatc     240
agcagagtgg aggctgagga tgttggcctt tattactgca tgcaacagct agaacagccg     300
tacacttttg gccaggggac caagctggag atcaaa                               336
```

<210> SEQ ID NO 66
<211> LENGTH: 112
<212> TYPE: PRT
<213> ORGANISM: Artificial Sequence
<220> FEATURE:

<223> OTHER INFORMATION: Synthetic Construct

<400> SEQUENCE: 66

Asp Val Val Met Thr Gln Ser Pro Leu Ser Leu Pro Val Thr Pro Gly
1               5                   10                  15

Glu Ser Ala Thr Ile Ser Cys Arg Ser Ser Gln Ser Leu Leu Tyr Ser
            20                  25                  30

Asn Gly Tyr Asn Tyr Leu Asp Trp Tyr Leu Leu Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Gln
                85                  90                  95

Leu Glu Gln Pro Tyr Thr Phe Gly Gln Gly Thr Lys Leu Glu Ile Lys
            100                 105                 110

<210> SEQ ID NO 67
<211> LENGTH: 454
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Val Gly Ala Thr Pro Thr Tyr Tyr Tyr Trp Trp Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

```
Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 68
<211> LENGTH: 219
<212> TYPE: PRT
<213> ORGANISM: Artificial Sequence
<220> FEATURE:
<223> OTHER INFORMATION: Synthetic Construct

<400> SEQUENCE: 68

Asp Val Val Met Thr Gln Ser Pro Leu Ser Leu Pro Val Thr Pro Gly
1               5                   10                  15

Glu Ser Ala Thr Ile Ser Cys Arg Ser Ser Gln Ser Leu Leu Tyr Ser
            20                  25                  30

Asn Gly Tyr Asn Tyr Leu Asp Trp Tyr Leu Leu Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Asn Gly
                85                  90                  95

Leu Glu Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 69
<211> LENGTH: 454
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Val Gly Ala Asn Pro Thr Tyr Tyr Tyr Tyr Trp Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285
```

Val Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
            435                 440                 445

Ser Leu Ser Pro Gly Lys
    450

<210> SEQ ID NO 70
<211> LENGTH: 454
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met Tyr Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Val Gly Ala Asn Pro Thr Tyr Tyr Tyr Tyr Trp Asp
            100                 105                 110

Val Trp Gly Lys Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Leu Gly Thr Gln Thr Tyr Ile Cys Asn
        195                 200                 205

Val Asn His Lys Pro Ser Asn Thr Lys Val Asp Lys Lys Val Glu Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser His Glu Asp Pro Glu Val Lys Phe Asn Trp Tyr Val Asp Gly
    275                 280                 285

Val Glu Val His Asn Ala Lys Thr Lys Pro Arg Glu Glu Gln Tyr Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
        340                 345                 350

Pro Gln Val Tyr Thr Leu Pro Pro Ser Arg Asp Glu Leu Thr Lys Asn
    355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
            405                 410                 415

Leu Thr Val Asp Lys Ser Arg Trp Gln Gln Gly Asn Val Phe Ser Cys
        420                 425                 430

Ser Val Met His Glu Ala Leu His Asn His Tyr Thr Gln Lys Ser Leu
    435                 440                 445

Ser Leu Ser Pro Gly Lys
    450

```
<210> SEQ ID NO 71
<211> LENGTH: 219
<212> TYPE: PRT
<213> ORGANISM: Artificial Sequence
<220> FEATURE:
<223> OTHER INFORMATION: Synthetic Construct

<400> SEQUENCE: 71
```

Asp Val Val Met Thr Gln Ser Pro Leu Ser Leu Pro Val Thr Pro Gly
1               5                   10                  15

Glu Ser Ala Thr Ile Ser Cys Arg Ser Ser Gln Ser Leu Leu Tyr Ser
            20                  25                  30

Asn Gly Tyr Asn Tyr Leu Asp Trp Tyr Leu Leu Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Leu Tyr Tyr Cys Met Gln Gln
            85                  90                  95

Leu Glu Gln Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 72
<211> LENGTH: 663
<212> TYPE: DNA
<213> ORGANISM: Artificial Sequence
<220> FEATURE:
<223> OTHER INFORMATION: Synthetic Construct

<400> SEQUENCE: 72
gatgttgtga tgactcagtc tccactctcc ctgcccgtca cccctggaga gtcggccacc     60
atctcctgca ggtctagtca gagcctcctg tacagtaatg gatacaacta tttggattgg    120
tacctgctga agccagggca gtctccacaa ctcctgatct atttgggttc taatcgggcc    180
tccggggtcc ctgacaggtt cagtggcagt ggatcaggca cagattttac actgaagatc    240
agcagagtgg aggctgagga tgttggcctt tattactgca tgcaaggtct atgaactccg    300 tacactttg gccaggggac caagctggag atcaaacgaa ctgtggctgc accatctgtc    360
ttcatcttcc cgccatctga tgagcagttg aaatctggaa ctgcctctgt cgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgtc ctcgcccgtc acaaagagct tcaacagggg agagtgttga    660
taa                                                                   663

<210> SEQ ID NO 73
<211> LENGTH: 693
<212> TYPE: DNA
<213> ORGANISM: Artificial Sequence
<220> FEATURE:
<223> OTHER INFORMATION: Synthetic Construct

<400> SEQUENCE: 73
caggtacagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag gcttgagtg gatgggatgg atcaacccta acagtggtgg cacaaactat    180
gcacagaagt tcagggcag ggtcaccatg accagggaca cgtccatcag cacagcctac    240
atggagctga gcaggctgag atctgacgac acggccgtgt attactgtgc gagagaaaga    300

```
gtgggagcta cttgaaccta ctactactac atggacgtct ggggcaaagg gaccacggtc    360
accgtctcct cagcctccac caagggccca tcggtcttcc ccctggcacc ctcctccaag    420
agcacctctg ggggcacagc ggccctgggc tgcctggtca aggactactt ccccgaaccg    480
gtgacggtgt cgtggaactc aggcgccctg accagcggcg tgcacacctt cccggctgtc    540
ctacagtcct caggactcta ctccctcagc agcgtggtga ctgtgccctc tagcagcttg    600
ggcacccaga cctacatctg caacgtgaat cacaagccca gcaacaccaa ggtggacaag    660
aaagttgagc ccaaatcttg tgacaaaact cac                                 693
```

<210> SEQ ID NO 74
<211> LENGTH: 746
<212> TYPE: DNA
<213> ORGANISM: Artificial Sequence
<220> FEATURE:
<223> OTHER INFORMATION: Synthetic Construct

<400> SEQUENCE: 74

```
atgaaaaaga cagctatcgc gattgcagtg gcactggctg gtttcgctac cgtggcccag     60
gcggccgagc tcgatgttgt gatgactcag tctccactct ccctgcccgt cacccctgga    120
gagtcggcca ccatctcctg caggtctagt cagagcctcc tgtacagtaa tggatacaac    180
tatttggatt ggtacctgct gaagccaggg cagtctccac aactcctgat ctatttgggt    240
tctaatcggg cctccggggt ccctgacagg ttcagtggca gtggatcagg cacagatttt    300
acactgaaga tcagcagagt ggaggctgag gatgttggcc tttattactg catgcaaggt    360
ctagaaactc cgtacacttt tggccagggg accaagctgg agatcaaacg aactgtggct    420
gcaccatctg tcttcatctt cccgccatct gatgagcagt tgaaatctgg aactgcctct    480
gtcgtgtgcc tgctgaataa cttctatccc agagaggcca agtacagtg gaaggtggat    540 aacgccctcc aatcgggtaa ctcccaggag agtgtcacag agcaggacag caaggacagc    600
acctacagcc tcagcagcac cctgacgctg agcaaagcag actacgagaa acacaaagtc    660
tacgcctgcg aagtcaccca tcagggcctg tcctcgcccg tcacaaagag cttcaacagg    720
ggagagtgat taattaatc tagata                                          746
```

<210> SEQ ID NO 75
<211> LENGTH: 746
<212> TYPE: DNA
<213> ORGANISM: Artificial Sequence
<220> FEATURE:
<223> OTHER INFORMATION: Synthetic Construct

<400> SEQUENCE: 75

```
gccgctggat tgttattact cgctgcccaa ccagccatgg ccgaggtgca gctgctcgag     60
caggtacagc tggtgcagtc tggggctgag gtgaagaagc ctggggcctc agtgaaggtc    120
tcctgcaagg cttctggata caccttcacc ggctactata tgcactgggt gcgacaggcc    180
cctggacaag gcttgagtg gatgggatgg atcaaccctca acagtggtgg cacaaactat    240
gcacagaagt ttcagggcag ggtcaccatg accagggaca cgtccatcag cacagcctac    300
atggagctga gcaggctgag atctgacgac acggccgtgt attactgtgc gagagaaaga    360
gtgggagcta ctccgaccta ctactactac atggacgtct ggggcaaagg gaccacggtc    420
accgtctcct cagcctccac caagggccca tcggtcttcc ccctggcacc ctcctccaag    480
agcacctctg ggggcacagc ggccctgggc tgcctggtca aggactactt ccccgaaccg    540
gtgacggtgt cgtggaactc aggcgccctg accagcggcg tgcacacctt cccggctgtc    600
```

```
ctacagtcct caggactcta ctccctcagc agcgtggtga ctgtgccctc tagcagcttg    660
ggcacccaga cctacatctg caacgtgaat cacaagccca gcaacaccaa ggtggacaag    720
aaagttgaca aaactagtgg ccaggc                                          746

<210> SEQ ID NO 76
<211> LENGTH: 17
<212> TYPE: PRT
<213> ORGANISM: Artificial Sequence
<220> FEATURE:
<223> OTHER INFORMATION: Synthetic Construct

<400> SEQUENCE: 76

Met Tyr Trp Val Arg Gln Ala Pro Gly Gln Gly Leu Glu Trp Met Gly
1               5                   10                  15

Trp
```